(12) United States Patent
Cook et al.

(10) Patent No.: US 6,974,865 B2
(45) Date of Patent: *Dec. 13, 2005

(54) C3'-METHYLENE HYDROGEN PHOSPHONATE OLIGOMERS AND RELATED COMPOUNDS

(75) Inventors: Phillip Dan Cook, Fallbrook, CA (US); Muthiah Manoharan, Carlsbad, CA (US); Martin Maier, Carlsbad, CA (US); Haoyun An, Carlsbad, CA (US)

(73) Assignee: ISIS Pharmaceuticals, Inc., Carlsbad, CA (US)

(*) Notice: Subject to any disclaimer, the term of this patent is extended or adjusted under 35 U.S.C. 154(b) by 40 days.

This patent is subject to a terminal disclaimer.

(21) Appl. No.: 10/322,242

(22) Filed: Dec. 18, 2002

(65) Prior Publication Data

US 2003/0139586 A1 Jul. 24, 2003

Related U.S. Application Data

(63) Continuation of application No. 09/349,033, filed on Jul. 7, 1999, now Pat. No. 6,639,061, and a continuation of application No. 10/153,320, filed on May 22, 2002, which is a continuation of application No. 09/058,470, filed on Apr. 10, 1998, now abandoned, which is a division of application No. 08/763,354, filed on Dec. 11, 1996, now Pat. No. 5,965,721, which is a continuation of application No. 08/150,079, filed on Apr. 7, 1994, now Pat. No. 5,610,289.

(51) Int. Cl.$^7$ .................. C07H 21/02; C07H 21/04
(52) U.S. Cl. .............. 536/23.1; 536/22.1; 536/24.5; 536/25.3; 536/25.31; 536/25.34; 536/25.6; 536/26.1; 435/87; 435/90; 435/91.1; 435/91.2; 435/91.5
(58) Field of Search ............... 536/22.1, 23.1, 536/24.5, 26.1, 28.1; 435/87, 90, 91.1, 91.2, 91.5

(56) References Cited

U.S. PATENT DOCUMENTS

| | | | |
|---|---|---|---|
| 3,687,808 A | 8/1972 | Merigan et al. | 195/28 |
| 4,415,732 A | 11/1983 | Caruthers et al. | 536/27 |
| 4,458,066 A | 7/1984 | Caruthers et al. | 536/27 |
| 4,500,707 A | 2/1985 | Caruthers et al. | 536/27 |
| 4,668,777 A | 5/1987 | Caruthers et al. | 536/27 |
| 4,725,677 A | 2/1988 | Köster et al. | 536/27 |
| 4,973,679 A | 11/1990 | Caruthers et al. | 536/27 |
| 5,132,418 A | 7/1992 | Caruthers et al. | 536/27 |
| RE34,069 E | 9/1992 | Köster et al. | 536/27 |
| 5,153,319 A | 10/1992 | Caruthers et al. | 536/27 |
| 5,212,295 A | 5/1993 | Cook | 536/26.7 |
| 5,334,711 A * | 8/1994 | Sproat et al. | 536/24.5 |
| 5,453,496 A | 9/1995 | Caruthers et al. | 536/24.5 |
| 5,548,076 A | 8/1996 | Froehler et al. | 536/25.34 |
| 5,610,289 A * | 3/1997 | Cook et al. | 536/25.34 |
| 5,614,621 A | 3/1997 | Ravikumar et al. | 536/25.34 |
| 5,670,633 A | 9/1997 | Cook et al. | 536/23.1 |
| 5,705,621 A | 1/1998 | Ravikumar | 536/23.1 |
| 5,705,629 A | 1/1998 | Bhongle | 536/25.34 |
| 5,760,209 A | 6/1998 | Cheruvallath et al. | 536/25.34 |
| 5,783,690 A | 7/1998 | Cheruvallath et al. | 536/55.3 |
| 6,166,197 A | 12/2000 | Cook et al. | 536/24.5 |
| 6,172,209 B1 | 1/2001 | Manoharan et al. | 536/23.1 |
| 6,271,358 B1 | 8/2001 | Manoharan et al. | 536/23.1 |

FOREIGN PATENT DOCUMENTS

| WO | WO 96/08503 A1 | 3/1996 |
|---|---|---|
| WO | WO 97/32887 | 9/1997 |

OTHER PUBLICATIONS

Agrawal et al. (eds.), "Methods of Molecular Biology", in *Protocols for Oligonucleotide Conjugates*, Agrawal, S. (ed.), Humana Press, New Jersey, 1994, vol. 26, 1–72.

Albrecht, H.P. et al., "Synthesis of Isosteric Phosphonate Analogs of Some Biologically Important Phosphodiesters", *J. Am. Chem. Soc.*, 1970, 92, 5510–5513.

Albrecht et al., "Homonucleoside Phosphonic Acids—I—A General Synthesis of Isosteric Phosphonate Analogs of Nucleoside 3'–Phosphates," *Tetrahedron*, 1984, 40(1), 79–85.

Alul, R.H. et al., "Oxalyl–CPG: a labile support for synthesis of sensitive oligonucleotide derivatives", *Nucl. Acid Res.*, 1991, 19, 1527–1532.

Beaucage, S.L. et al., "The Functionalization of Oligonucleotides Via Phosphoramidite Derivatives," *Tetrahedron*, 1993, 49(10), 1925–1963.

Beaucage, S.L. et al., "The Synthesis of Specific Ribonucleotides and Unrelated Phosphorylated Biomolecules by the Phosphoramidite Method," *Tetrahedron*, 1993, 49(46), 10441–10488.

Beaucage, S.L. et al., "Advances in the Synthesis of Oligonucleotides by the Phosphoramidite Approach", *Tetrahedron*, 1992, 48, 2223–2311.

Bhat, B. et al., "Synthesis of Novel Nucleic Acid Mimics via the Stereoselective Intermolecular Radical Coupling of 3'–Iodo Nucleosides and Formaldoximines", *J. Org. Chem.*, 1996, 61, 8186–8199.

Breaker et al., "Synthesis and Properties of Adenosine Oligonucleotide Analogues Containing Methylene Groups in Place of Phosphodiester 5'–Oxygens," *Biochem.*, 1993, 32, 9125–9128.

Brown, T. et al., "Modern machine–aided methods of oligodeoxyribonucleotide synthesis," *Oligonucleotides and Analogues: A Practical Approach*, 1991, Chapter 1, Eckstein, F. (ed.), IRL Press, New York, 1–24.

(Continued)

Primary Examiner—James O. Wilson
Assistant Examiner—Traviss C. McIntosh, III
(74) Attorney, Agent, or Firm—Isis Patent Department

(57) ABSTRACT

The present invention is directed to nucleoside monomers wherein the 3'-O atom is replaced with a methylene group. The present invention also provides oligomers comprising a plurality of such monomers which are linked by methylene phosphonate linkages. Further, methods of preparing monomers and oligomers according to the present invention are provided.

4 Claims, 15 Drawing Sheets

OTHER PUBLICATIONS

Cook, P.D., "Medicinal Chemistry of Antisense Oligonucleotides—future opportunities", *Anti–Cancer Drug Design*, 1991, 6, 585–607.

Cormier, J.F. et al., "Synthesis of hexanucleotide analogues containing diisopropylsilyl internucleotide linkages", *Nucl. Acids Res.*, 1988, 16, 4583–4594.

Crooke, S.T. et al., "Pharmacokinetic Properties of Several Novel Oligonucleotide Analogs in mice", *J. Pharmacol. Exp. Therapeutics*, 1996, 277, 923–937.

Delgado, C. et al., "The Uses and Properties of PEG–Linked Proteins", *Crit. Rev. in Therapeutic Drug Carrier Sys.*, 1992, 9, 249–304.

Derry et al., "Synthesis and biological activity of novel thymidine derivatives of podophyllotoxin and 4'–demethylepipodophyllotoxin," *Anti–Cancer Drug Design*, 1993, 8, 203–221.

Englisch, U. et al., "Chemically Modified Oligonucleotides as Probes and Inhibitors", *Angew. Chem. Int. Ed. Eng.*, 1991, 30, 613–629.

Froehler et al., "Nucleoside H–Phosphonates: Valuable Intermediates in the Synthesis of Deoxyoligonucleotides," *Tetra. Lett.*, 1986, 27(4), 469–472.

Goodchild, J., "Conjugates of Oligonucleotides and Modified Oligonucleotides: A Review of their synthesis and Properties", *Bioconjugate Chem.*, 1990, 1, 165–187.

Hamm, M. L. et al., "Incorporation of 2'–Deoxy–2'–mercaptocytidine into Oligonucleotides via Phosphoramidite Chemistry," *J. Org. Chem.*, 1997, 62, 3415–3420.

Heinemann, U. et al., "Effect of a single 3'–methylene phosphonate linkage on the conformation of an A–DNA octamer double helix", *Nucl. Acids Res.*, 1991, 19, 427–433.

Kabanov, A.V., "A new class of antivirals: antisense olgonucleotides combined with a hydrophobic substituent effectively inhibit influenza virus reproduction and synthesis of virus–specific proteins in MDCK cells", *FEBS Letts.*, 1990, 259, 327–330.

Kroschwitz, J.I., "Polynucleotides", *Concise Encyclopedia of Polymer Science and Engineering*, 1990, John Wiley & Sons, New York, 858–859.

Lebreton, J. et al., "Comparison of two Amides as Backbone Replacement of the Phosphodiester Linkage in Oligodeoxynucleotides," *Tetrahedron Letts.*, 1994, 35, 5225–5228.

Letsinger, R.L. et al.. "Cholesteryl–conjugated oligonucleotides: Synthesis, properties and activity as inhibitors of replication of human immunodeficiency virus in cell culture", *Proc. Natl. Acad. Sci.*, 1989, 86, 6553–6556.

Loke, S.L. et al., "Delivery of c–myc Antisense Phoshorothioate Oligodeoxynucleotides to Hemopoietic Cells in Culture by Liposome Fusion: Specific Reduction in c–myc Protein Expression Correlates with Inhibition of Cell Growth and DNA Synthesis", *Curr. Topics in Microbiol. & Immunol.*, 1988, 141, 282–289.

Manoharan, M. et al., "Introduction of a Lipophilic Thioether Tether in the Minor Groove of Nucleic Acids for Antisense Applications", *Bioorg. Med. Chem. Letts.*, 1993, 3, 2765–2770.

Manoharan M. et al., "Oligonucleotide Conjugates: Alteration of the Pharmacokinetic Properties of Antisense Agents", *Nucleosides and Nucleotides*, 1995, 14, 969–973.

Manoharan M. et al, "Cholic Acid–Oligonucliotide Conjugates for Antisense Applications", *Bioorganic Med. Chem. Letts.*, 1994, 4, 1053–1060.

Manoharan, M. et al., "Chemical Modifications to Improve Uptake and Bioavailability of Antisense Oligonucleotides", *Annals NY Acad. Sciences*, 1992, 660, 306–309.

Manoharan, M. et al., "Lipidic Nucleic Acids", *Tetrahedron Letts.*, 1995, 36, 3651–3654.

Marcus–Sekura, C.J. et al., "Comparative inhibition of chloramphenicol acetyltransferase gene expression by antisense oligonucleotide analogues having alkyl phosphotriester, methylphosphonate and phosphorothioate linkages", *Nucl. Acids Res.*, 1987, 15, 5749–5763.

Matteucci, M., "Deoxyoligonucleotide Analogs Based on Formacetal Linkages", *Tetrahedron Letts.*, 1990, 31, 2385–2388.

Mazur, A. et al., "Isoteres of Natural Phosphates. 11. Synthesis of a Phosphonic Acid Analogur of an Oligonucleotide", *Tetrahedron*, 1984, 40, 3949–3956.

McConnell et al., "Phosphorus–Containing Derivatives of 2,2–Dimethyl–1, 3–propanediol," *J. Org. Chem.*, 1959, 24, 630–635.

Mihkailov et al., "Ribosylation of Pyrimidine 2'–Deoxynucleosides," *Nucleosides and Nucleotides*, 1996, 15(7&8), 1323–1334.

Miller, P.S. et al., "Effects of a Trinucleotide Ethyl Phosphotriester, G'''p(Et)G'''p(Et)U, on Mammalian Cells in Culture", *Biochem.*, 1977, 16, 1988–1996.

Mishra, R.K. et al., "Improved leishmanicidal effect of phosphorotioate antisense oligonucleotides by LDL–medicated delivery", *Biochim. Et Biophysica*, 1995, 1264, 229–237.

Montchamp et al., "Double Arbuzov Reaction of in Situ Generated Bis(trimethylsiloxy)phosphine with Dielectrophiles: Methodology for the Synthesis of Cyclic Phoshinic Acids," *J. Org. Chem.*, 1995, 60, 6076–6081.

Morr et al., "2', 3'–Dideoxy–3'–C–(phosphonomethyl)adenosine, the Phosphonate Analogue of 2'–Deoxyadenosine 3'–Phosphate," *Z. Naturforsch.*, 1983, 38b, 1665–1668.

Morr et al., "Base–Hydrogenated Phosphonic Acid Derivatives of Pyrimidine Nucleosides, Side Products in the Deoxygenation of 2'–O–Phenoxythiocarbonyl Precursors," *Liebigs Ann. Chemie*, 1993, 1205–1210 (English abstract included).

Oberhauser, B. et al., "Effective incorporation of 2'–O–methyl–oligonucleotides into liposomes and enhanced cell association through modification with thiocholesterol", *Nucl. Acids Res.*, 1992, 20, 533–538.

Svinarchuk, F.P. et al., "Inhibition of HIV proliferation in MT–4 cells by antisense oligonucleotide conjugated to lipophilic groups", *Biochimie*, 1993, 79, 49–54.

Thomson, J. B. et al., "Synthesis and Properties of Diuridine Phosphate Analogues Containing Thio and Amino Modifications," *J. Org. Chem.*, 1996, 61, 6273–6281.

Wilson, D.B., "Cellular Transport Mechanisms", *Ann. Rev. Biochem.*, 1971, 47, 933–965.

Wright, P. et al., "Large Scale Synthesis of Oligonucleotides via phosphoramidite Nucleosides and a High–loaded Polystyrene Support", *Tetrahedron Letts.*, 1993, 34, 3373–3376.

* cited by examiner (DMT)

32, R = OCH₃
44, R = F
44a, R = H
66, R = OCH₂CH₂OCH₃

(MMT)

50, R = OCH₃
51, R = F
52, R = H
53, R = OCH₂CH₂OCH₃

SEQUENCE LISTING

<160> NUMBER OF SEQ ID NOS: 12

<210> SEQ ID NO 1
<211> LENGTH: 19
<212> TYPE: DNA

-continued

```
<213> ORGANISM: Artificial Sequence
<220> FEATURE:
<223> OTHER INFORMATION: Synthetic Oligonucleotide Sequence

<400> SEQUENCE: 1
tttttttttt tttttttt                                              19

<210> SEQ ID NO 2
<211> LENGTH: 13
<212> TYPE: DNA
<213> ORGANISM: Artificial Sequence
<220> FEATURE:
<223> OTHER INFORMATION: Synthetic Oligonucleotide Sequence
<220> FEATURE:
<221> NAME/KEY: misc_feature
<222> LOCATION: (1)..(1)
<223> OTHER INFORMATION: n = 5-methyluridine
<220> FEATURE:
<221> NAME/KEY: misc_feature
<222> LOCATION: (1)..(2)
<223> OTHER INFORMATION: 2'-O-methyl nucleotide
<220> FEATURE:
<221> NAME/KEY: misc_feature
<222> LOCATION: (1)..(2)
<223> OTHER INFORMATION: 3'-methylenephosphonate linkage
<220> FEATURE:
<221> NAME/KEY: misc_feature
<222> LOCATION: (2)..(13)
<223> OTHER INFORMATION: n = deoxythymidine

<400> SEQUENCE: 2
nnnnnnnnnn nnn                                                   13

<210> SEQ ID NO 3
<211> LENGTH: 19
<212> TYPE: DNA
<213> ORGANISM: Artificial Sequence
<220> FEATURE:
<223> OTHER INFORMATION: Synthetic Oligonucleotide Sequence
<220> FEATURE:
<221> NAME/KEY: misc_feature
<222> LOCATION: (1)..(15)
<223> OTHER INFORMATION: n = deoxythymidine
<220> FEATURE:
<221> NAME/KEY: misc_feature
<222> LOCATION: (16)..(19)
<223> OTHER INFORMATION: n = 5-methyluridine
<220> FEATURE:
<221> NAME/KEY: misc_feature
<222> LOCATION: (16)..(17)
<223> OTHER INFORMATION: 2'-O-methyl nucleotide
<220> FEATURE:
<221> NAME/KEY: misc_feature
<222> LOCATION: (16)..(17)
<223> OTHER INFORMATION: 3'-methylenephosphonate linkage
<220> FEATURE:
<221> NAME/KEY: misc_feature
<222> LOCATION: (17)..(18)
<223> OTHER INFORMATION: 2'-O-methyl nucleotide
<220> FEATURE:
<221> NAME/KEY: misc_feature
<222> LOCATION: (17)..(18)
<223> OTHER INFORMATION: 3'-methylenephosphonate linkage
<220> FEATURE:
<221> NAME/KEY: misc_feature
<222> LOCATION: (18)..(19)
<223> OTHER INFORMATION: 2'-O-methyl nucleotide
<220> FEATURE:
<221> NAME/KEY: misc_feature
<222> LOCATION: (18)..(19)
<223> OTHER INFORMATION: 3'-methylenephosphonate linkage
<220> FEATURE:
<221> NAME/KEY: misc_feature
<222> LOCATION: (19)..(19)
<223> OTHER INFORMATION: 2'-O-methyl nucleotide
```

-continued

```
<400> SEQUENCE: 3 nnnnnnnnn nnnnnnnn                                                  19

<210> SEQ ID NO 4
<211> LENGTH: 10
<212> TYPE: DNA
<213> ORGANISM: Artificial Sequence
<220> FEATURE:
<223> OTHER INFORMATION: Synthetic Oligonucleotide Sequence
<220> FEATURE:
<221> NAME/KEY: misc_feature
<222> LOCATION: (4)..(4)
<223> OTHER INFORMATION: n = deoxythymidine
<220> FEATURE:
<221> NAME/KEY: misc_feature
<222> LOCATION: (6)..(6)
<223> OTHER INFORMATION: n = 5-methyluridine
<220> FEATURE:
<221> NAME/KEY: misc_feature
<222> LOCATION: (6)..(7)
<223> OTHER INFORMATION: 2'-O-methyl nucleotide
<220> FEATURE:
<221> NAME/KEY: misc_feature
<222> LOCATION: (6)..(7)
<223> OTHER INFORMATION: 3' - methylenephosphonate linkage

<400> SEQUENCE: 4 gcgnanacgc                                                          10

<210> SEQ ID NO 5
<211> LENGTH: 15
<212> TYPE: DNA
<213> ORGANISM: Artificial Sequence
<220> FEATURE:
<223> OTHER INFORMATION: Synthetic Oligonucleotide Sequence
<220> FEATURE:
<221> NAME/KEY: misc_feature
<222> LOCATION: (1)..(3)
<223> OTHER INFORMATION: n = deoxythymidine
<220> FEATURE:
<221> NAME/KEY: misc_feature
<222> LOCATION: (4)..(5)
<223> OTHER INFORMATION: 3'-methylenephosphonate linkage
<220> FEATURE:
<221> NAME/KEY: misc_feature
<222> LOCATION: (4)..(5)
<223> OTHER INFORMATION: 2'-O-methyl nucleotide
<220> FEATURE:
<221> NAME/KEY: misc_feature
<222> LOCATION: (4)..(4)
<223> OTHER INFORMATION: n = 5-methyluridine
<220> FEATURE:
<221> NAME/KEY: misc_feature
<222> LOCATION: (5)..(5)
<223> OTHER INFORMATION: n = deoxythymidine
<220> FEATURE:
<221> NAME/KEY: misc_feature
<222> LOCATION: (7)..(7)
<223> OTHER INFORMATION: n = deoxythymidine
<220> FEATURE:
<221> NAME/KEY: misc_feature
<222> LOCATION: (9)..(9)
<223> OTHER INFORMATION: n = deoxythymidine
<220> FEATURE:
<221> NAME/KEY: misc_feature
<222> LOCATION: (11)..(11)
<223> OTHER INFORMATION: n = deoxythymidine
<220> FEATURE:
<221> NAME/KEY: misc_feature
<222> LOCATION: (13)..(13)
<223> OTHER INFORMATION: n = deoxythymidine
<220> FEATURE:
<221> NAME/KEY: misc_feature
<222> LOCATION: (15)..(15)
```

```
<223> OTHER INFORMATION: n = deoxythymidine

<400> SEQUENCE: 5
nnnnncncnc ncncn                                                  15

<210> SEQ ID NO 6
<211> LENGTH: 18
<212> TYPE: DNA
<213> ORGANISM: Artificial Sequence
<220> FEATURE:
<223> OTHER INFORMATION: Synthetic Oligonucleotide Sequence
<220> FEATURE:
<221> NAME/KEY: misc_feature
<222> LOCATION: (2)..(2)
<223> OTHER INFORMATION: n = deoxythymidine
<220> FEATURE:
<221> NAME/KEY: misc_feature
<222> LOCATION: (5)..(5)
<223> OTHER INFORMATION: n = deoxythymidine
<220> FEATURE:
<221> NAME/KEY: misc_feature
<222> LOCATION: (8)..(11)
<223> OTHER INFORMATION: n = 5-methyluridine
<220> FEATURE:
<221> NAME/KEY: misc_feature
<222> LOCATION: (16)..(16)
<223> OTHER INFORMATION: n = deoxythymidine
<220> FEATURE:
<221> NAME/KEY: misc_feature
<222> LOCATION: (8)..(9)
<223> OTHER INFORMATION: 2'-O-methyl
<220> FEATURE:
<221> NAME/KEY: misc_feature
<222> LOCATION: (8)..(9)
<223> OTHER INFORMATION: 3'-methylenephosphonate linkage
<220> FEATURE:
<221> NAME/KEY: misc_feature
<222> LOCATION: (9)..(10)
<223> OTHER INFORMATION: 2'-O-methyl
<220> FEATURE:
<221> NAME/KEY: misc_feature
<222> LOCATION: (9)..(10)
<223> OTHER INFORMATION: 3'-methylenephosphonate linkage
<220> FEATURE:
<221> NAME/KEY: misc_feature
<222> LOCATION: (10)..(11)
<223> OTHER INFORMATION: 2'-O-methyl
<220> FEATURE:
<221> NAME/KEY: misc_feature
<222> LOCATION: (10)..(11)
<223> OTHER INFORMATION: 3'-methylenephosphonate linkage
<220> FEATURE:
<221> NAME/KEY: misc_feature
<222> LOCATION: (11)..(12)
<223> OTHER INFORMATION: 2'-O-methyl
<220> FEATURE:
<221> NAME/KEY: misc_feature
<222> LOCATION: (11)..(12)
<223> OTHER INFORMATION: 3'-methylenephosphonate linkage

<400> SEQUENCE: 6
cncgnacnnn nccggncc                                               18

<210> SEQ ID NO 7
<211> LENGTH: 16
<212> TYPE: DNA
<213> ORGANISM: Artificial Sequence
<220> FEATURE:
<223> OTHER INFORMATION: Synthetic Oligonucleotide Sequence
<220> FEATURE:
<221> NAME/KEY: misc_feature
<222> LOCATION: (1)..(1)
<223> OTHER INFORMATION: n = 5-methyluridine
<220> FEATURE:
<221> NAME/KEY: misc_feature
```

```
<222> LOCATION: (1)..(2)
<223> OTHER INFORMATION: 2'-O-methyl
<220> FEATURE:
<221> NAME/KEY: misc_feature
<222> LOCATION: (1)..(2)
<223> OTHER INFORMATION: 3'-methylenephosphonate linkage
<220> FEATURE:
<221> NAME/KEY: misc_feature
<222> LOCATION: (7)..(7)
<223> OTHER INFORMATION: n = 5-methyluridine
<220> FEATURE:
<221> NAME/KEY: misc_feature
<222> LOCATION: (7)..(8)
<223> OTHER INFORMATION: 2'-O-methyl
<220> FEATURE:
<221> NAME/KEY: misc_feature
<222> LOCATION: (7)..(8)
<223> OTHER INFORMATION: 3'-methylenephosphonate linkagel
<220> FEATURE:
<221> NAME/KEY: misc_feature
<222> LOCATION: (9)..(9)
<223> OTHER INFORMATION: n = 5-methyluridine
<220> FEATURE:
<221> NAME/KEY: misc_feature
<222> LOCATION: (9)..(10)
<223> OTHER INFORMATION: 2'-O-methyl
<220> FEATURE:
<221> NAME/KEY: misc_feature
<222> LOCATION: (9)..(10)
<223> OTHER INFORMATION: 3'-methylenephosphonate linkage
<220> FEATURE:
<221> NAME/KEY: misc_feature
<222> LOCATION: (15)..(15)
<223> OTHER INFORMATION: n = 5-methyluridine
<220> FEATURE:
<221> NAME/KEY: misc_feature
<222> LOCATION: (15)..(16)
<223> OTHER INFORMATION: 2'-O-methyl
<220> FEATURE:
<221> NAME/KEY: misc_feature
<222> LOCATION: (15)..(16)
<223> OTHER INFORMATION: 3'-methylenephosphonate linkage

<400> SEQUENCE: 7
nccaggngnc cgcanc                                                   16

<210> SEQ ID NO 8
<211> LENGTH: 13
<212> TYPE: DNA
<213> ORGANISM: Artificial Sequence
<220> FEATURE:
<223> OTHER INFORMATION: Synthetic Oligonucleotide Sequence
<220> FEATURE:
<221> NAME/KEY: misc_feature
<222> LOCATION: (1)..(1)
<223> OTHER INFORMATION: n = deoxythymidine
<220> FEATURE:
<221> NAME/KEY: misc_feature
<222> LOCATION: (2)..(2)
<223> OTHER INFORMATION: n = 5-methyluridine
<220> FEATURE:
<221> NAME/KEY: misc_feature
<222> LOCATION: (2)..(3)
<223> OTHER INFORMATION: 2'-O-methyl nucleotide
<220> FEATURE:
<221> NAME/KEY: misc_feature
<222> LOCATION: (2)..(3)
<223> OTHER INFORMATION: 3'-methylenethiophosphonate linkage
<220> FEATURE:
<221> NAME/KEY: misc_feature
<222> LOCATION: (3)..(13)
<223> OTHER INFORMATION: n = deoxythymidine

<400> SEQUENCE: 8
nnnnnnnnnn nnn                                                      13
```

```
<210> SEQ ID NO 9
<211> LENGTH: 10
<212> TYPE: DNA
<213> ORGANISM: Artificial Sequence
<220> FEATURE:
<223> OTHER INFORMATION: Synthetic Oligonucleotide Sequence
<220> FEATURE:
<221> NAME/KEY: misc_feature
<222> LOCATION: (4)..(4)
<223> OTHER INFORMATION: n = deoxythymidine
<220> FEATURE:
<221> NAME/KEY: misc_feature
<222> LOCATION: (6)..(6)
<223> OTHER INFORMATION: n = 5-methyluridine
<220> FEATURE:
<221> NAME/KEY: misc_feature
<222> LOCATION: (6)..(7)
<223> OTHER INFORMATION: 3'-methylenephosphonate linkage
<220> FEATURE:
<221> NAME/KEY: misc_feature
<222> LOCATION: (6)..(7)
<223> OTHER INFORMATION: 2'-fluoro

<400> SEQUENCE: 9 gcgnanacgc                                                          10

<210> SEQ ID NO 10
<211> LENGTH: 16
<212> TYPE: DNA
<213> ORGANISM: Artificial Sequence
<220> FEATURE:
<223> OTHER INFORMATION: Synthetic Oligonucleotide Sequence
<220> FEATURE:
<221> NAME/KEY: misc_feature
<222> LOCATION: (1)..(1)
<223> OTHER INFORMATION: n = 5-methyluridine
<220> FEATURE:
<221> NAME/KEY: misc_feature
<222> LOCATION: (1)..(2)
<223> OTHER INFORMATION: 2'-fluoro
<220> FEATURE:
<221> NAME/KEY: misc_feature
<222> LOCATION: (1)..(2)
<223> OTHER INFORMATION: 3'-methylenephosphonate linkage
<220> FEATURE:
<221> NAME/KEY: misc_feature
<222> LOCATION: (7)..(7)
<223> OTHER INFORMATION: n = 5-methyluridine
<220> FEATURE:
<221> NAME/KEY: misc_feature
<222> LOCATION: (7)..(8)
<223> OTHER INFORMATION: 2'-fluoro
<220> FEATURE:
<221> NAME/KEY: misc_feature
<222> LOCATION: (7)..(8)
<223> OTHER INFORMATION: 3'-methylenephosphonate linkage
<220> FEATURE:
<221> NAME/KEY: misc_feature
<222> LOCATION: (9)..(9)
<223> OTHER INFORMATION: n = 5-methyluridine
<220> FEATURE:
<221> NAME/KEY: misc_feature
<222> LOCATION: (9)..(10)
<223> OTHER INFORMATION: 2'-fluoro
<220> FEATURE:
<221> NAME/KEY: misc_feature
<222> LOCATION: (9)..(10)
<223> OTHER INFORMATION: 3'-methylenephosphonate linkage
<220> FEATURE:
<221> NAME/KEY: misc_feature
<222> LOCATION: (15)..(15)
<223> OTHER INFORMATION: n = 5-methyluridine
<220> FEATURE:
<221> NAME/KEY: misc_feature
<222> LOCATION: (15)..(16)
<223> OTHER INFORMATION: 2'-fluoro
```

```
<220> FEATURE:
<221> NAME/KEY: misc_feature
<222> LOCATION: (15)..(16)
<223> OTHER INFORMATION: 3'-methylenephosphonate linkage

<400> SEQUENCE: 10
nccaggngnc cgcanc                                                        16

<210> SEQ ID NO 11
<211> LENGTH: 18
<212> TYPE: DNA
<213> ORGANISM: Artificial Sequence
<220> FEATURE:
<223> OTHER INFORMATION: Synthetic Oligonucleotide Sequence
<220> FEATURE:
<221> NAME/KEY: misc_feature
<222> LOCATION: (2)..(2)
<223> OTHER INFORMATION: n = deoxythymidine
<220> FEATURE:
<221> NAME/KEY: misc_feature
<222> LOCATION: (8)..(9)
<223> OTHER INFORMATION: 2'-fluoro
<220> FEATURE:
<221> NAME/KEY: misc_feature
<222> LOCATION: (8)..(9)
<223> OTHER INFORMATION: 3'-methylenephosphonate linkage
<220> FEATURE:
<221> NAME/KEY: misc_feature
<222> LOCATION: (9)..(10)
<223> OTHER INFORMATION: 2'-fluoro
<220> FEATURE:
<221> NAME/KEY: misc_feature
<222> LOCATION: (9)..(10)
<223> OTHER INFORMATION: 3'-methylenephosphonate linkage
<220> FEATURE:
<221> NAME/KEY: misc_feature
<222> LOCATION: (10)..(11)
<223> OTHER INFORMATION: 2'-fluoro
<220> FEATURE:
<221> NAME/KEY: misc_feature
<222> LOCATION: (10)..(11)
<223> OTHER INFORMATION: 3'-methylenephosphonate linkage
<220> FEATURE:
<221> NAME/KEY: misc_feature
<222> LOCATION: (11)..(12)
<223> OTHER INFORMATION: 2'-fluoro
<220> FEATURE:
<221> NAME/KEY: misc_feature
<222> LOCATION: (11)..(12)
<223> OTHER INFORMATION: 3'-methylenephosphonate linkage
<220> FEATURE:
<221> NAME/KEY: misc_feature
<222> LOCATION: (5)..(5)
<223> OTHER INFORMATION: n = deoxythymidine
<220> FEATURE:
<221> NAME/KEY: misc_feature
<222> LOCATION: (8)..(11)
<223> OTHER INFORMATION: n = 5-methyluridine
<220> FEATURE:
<221> NAME/KEY: misc_feature
<222> LOCATION: (16)..(16)
<223> OTHER INFORMATION: n = deoxythymidine

<400> SEQUENCE: 11
cncgnacnnn nccggncc                                                      18

<210> SEQ ID NO 12
<211> LENGTH: 16
<212> TYPE: DNA
<213> ORGANISM: Artificial Sequence
<220> FEATURE:
<223> OTHER INFORMATION: Synthetic Oligonucleotide Sequence
<220> FEATURE:
<221> NAME/KEY: misc_feature
<222> LOCATION: (4)..(13)
```

```
<223> OTHER INFORMATION: n = 5-methyluridine
<220> FEATURE:
<221> NAME/KEY: misc_feature
<222> LOCATION: (4)..(5)
<223> OTHER INFORMATION: 2'-fluoro
<220> FEATURE:
<221> NAME/KEY: misc_feature
<222> LOCATION: (4)..(5)
<223> OTHER INFORMATION: 3'-methylene-phosphonate linkage
<220> FEATURE:
<221> NAME/KEY: misc_feature
<222> LOCATION: (5)..(6)
<223> OTHER INFORMATION: 2'-fluoro
<220> FEATURE:
<221> NAME/KEY: misc_feature
<222> LOCATION: (5)..(6)
<223> OTHER INFORMATION: 3'-methylene-phosphonate linkage
<220> FEATURE:
<221> NAME/KEY: misc_feature
<222> LOCATION: (6)..(7)
<223> OTHER INFORMATION: 2'-fluoro
<220> FEATURE:
<221> NAME/KEY: misc_feature
<222> LOCATION: (6)..(7)
<223> OTHER INFORMATION: 3'-methylene-phosphonate linkage
<220> FEATURE:
<221> NAME/KEY: misc_feature
<222> LOCATION: (7)..(8)
<223> OTHER INFORMATION: 2'-fluoro
<220> FEATURE:
<221> NAME/KEY: misc_feature
<222> LOCATION: (7)..(8)
<223> OTHER INFORMATION: 3'-methylene-phosphonate linkage
<220> FEATURE:
<221> NAME/KEY: misc_feature
<222> LOCATION: (8)..(9)
<223> OTHER INFORMATION: 2'-fluoro
<220> FEATURE:
<221> NAME/KEY: misc_feature
<222> LOCATION: (8)..(9)
<223> OTHER INFORMATION: 3'-methylene-phosphonate linkage
<220> FEATURE:
<221> NAME/KEY: misc_feature
<222> LOCATION: (9)..(10)
<223> OTHER INFORMATION: 2'-fluoro
<220> FEATURE:
<221> NAME/KEY: misc_feature
<222> LOCATION: (9)..(10)
<223> OTHER INFORMATION: 3'-methylene-phosphonate linkage
<220> FEATURE:
<221> NAME/KEY: misc_feature
<222> LOCATION: (10)..(11)
<223> OTHER INFORMATION: 2'-fluoro
<220> FEATURE:
<221> NAME/KEY: misc_feature
<222> LOCATION: (10)..(11)
<223> OTHER INFORMATION: 3'-methylene-phosphonate linkage
<220> FEATURE:
<221> NAME/KEY: misc_feature
<222> LOCATION: (11)..(12)
<223> OTHER INFORMATION: 2'-fluoro
<220> FEATURE:
<221> NAME/KEY: misc_feature
<222> LOCATION: (11)..(12)
<223> OTHER INFORMATION: 3'-methylene-phosphonate linkage
<220> FEATURE:
<221> NAME/KEY: misc_feature
<222> LOCATION: (12)..(13)
<223> OTHER INFORMATION: 2'-fluoro
<220> FEATURE:
<221> NAME/KEY: misc_feature
<222> LOCATION: (12)..(13)
<223> OTHER INFORMATION: 3'-methylene-phosphonate linkage
<220> FEATURE:
<221> NAME/KEY: misc_feature
<222> LOCATION: (13)..(14)
<223> OTHER INFORMATION: 2'-fluoro
<220> FEATURE:
<221> NAME/KEY: misc_feature
```

```
-continued

<222> LOCATION: (13)..(14)
<223> OTHER INFORMATION: 3'-methylene-phosphonate linkage

<400> SEQUENCE: 12
gcgnnnnnnn nnngcg                                              16
```

US 6,974,865 B2

C3'-METHYLENE HYDROGEN PHOSPHONATE OLIGOMERS AND RELATED COMPOUNDS

This application is a continuation of application Ser. No. 09/349,033, filed Jul. 7 1999, now U.S. Pat. No. 6,639,061, issued Oct. 28, 2003, the entirety of which is incorporated herein by reference. This application is also a continuation-in-part of application Ser. No. 10/153,320, filed May 22, 2002, which is a continuation of application Ser. No. 09/058,470, filed Apr. 10 1998, which has been abandoned, which in turn is a divisional of application Ser. No. 08/763,354, filed Dec. 11, 1996, issued on Oct. 12, 1999 as U.S. Pat. No. 5,965,721, which is a divisional of application Ser. No. 08/150,079, filed Apr. 7, 1994, issued Mar. 11, 1997 as U.S. Pat. No. 5,610,289.

FIELD OF THE INVENTION

The present invention is directed to oligonucleotides containing C3'-methylene hydrogen phosphonate monomers and methods for the preparation of such monomers and oligonucleotides.

BACKGROUND OF THE INVENTION

It is well known that most of the bodily states in mammals, including most disease states, are effected by proteins. Proteins, either acting directly or through their enzymatic functions, contribute in major proportion to many diseases in animals and man.

Classical therapeutics generally has focused upon interactions with proteins in an effort to moderate their disease-causing or disease-potentiating functions. Recently, however, attempts have been made to moderate the production of proteins by interactions with the molecules (i.e., intracellular RNA) that direct their synthesis. These interactions have involved hybridization of complementary "antisense" oligonucleotides or certain analogs thereof to RNA. Hybridization is the sequence-specific hydrogen bonding of oligonucleotides or oligonucleotide analogs to RNA or to single stranded DNA. By interfering with the production of proteins, it has been hoped to effect therapeutic results with maximum effect and minimal side effects.

Oligonucleotides and their analogs have been developed and used in molecular biology in a variety of procedures as probes, primers, linkers, adapters, and gene fragments. The pharmacological activity of antisense oligonucleotides and oligonucleotide analogs, like other therapeutics, depends on a number of factors that influence the effective concentration of these agents at specific intracellular targets. One important factor for oligonucleotides is the stability of the species in the presence of nucleases. It is unlikely that unmodified oligonucleotides will be useful therapeutic agents because they are rapidly degraded by nucleases. Modification of oligonucleotides to render them resistant to nucleases therefore is greatly desired.

Modification of oligonucleotides to enhance nuclease resistance generally has taken place on the phosphorus atom of the sugar-phosphate backbone. Examples of such modifications include methyl phosphonate, phosphorothioate, phosphorodithioate, phosphoramidate and phosphotriester linkages, and 2'-O-methyl ribose sugar units. Phosphate-modified oligonucleotides, however, generally have suffered from inferior hybridization properties. See, e.g., Cohen, J. S., ed. *Oligonucleotides: Antisense Inhibitors of Gene Expression*, (CRC Press, Inc., Boca Raton, Fla., 1989). Other modifications to oligonucleotides include labeling with nonisotopic labels, e.g. fluorescein, biotin, digoxigenin, alkaline phosphatase, or other reporter molecules.

Another key factor is the ability of antisense compounds to traverse the plasma membrane of specific cells involved in the disease process. Cellular membranes consist of lipid-protein bilayers that are freely permeable to small, nonionic, lipophilic compounds and are inherently impermeable to most natural metabolites and therapeutic agents. See, e.g., Wilson, *Ann. Rev. Biochem.* 1978, 47, 933. The biological and antiviral effects of natural and modified oligonucleotides in cultured mammalian cells have been well documented. It appears that these agents can penetrate membranes to reach their intracellular targets. Uptake of antisense compounds into a variety of mammalian cells, including HL-60, Syrian Hamster fibroblast, U937, L929, CV-1 and ATH8 cells has been studied using natural oligonucleotides and certain nuclease resistant analogs, such as alkyl triesters and methyl phosphonates. See, e.g., Miller et al., *Biochemistry* 1977, 16, 1988; Marcus-Sekura et al., *Nuc. Acids Res.* 1987, 15, 5749; and Loke et al., *Top. Microbiol. Immunol.* 1988, 141, 282.

Often, modified oligonucleotides and oligonucleotide analogs are internalized less readily than their natural counterparts. As a result, the activity of many previously available antisense oligonucleotides has not been sufficient for practical therapeutic, research or diagnostic purposes. Two other serious deficiencies of prior art compounds designed for antisense therapeutics are inferior hybridization to intracellular RNA and the lack of a defined chemical or enzyme-mediated event to terminate essential RNA functions.

Modifications to enhance the effectiveness of the antisense oligonucleotides and overcome these problems have taken many forms. These modifications include base ring modifications, sugar moiety modifications and sugar-phosphate backbone modifications. Prior sugar-phosphate backbone modifications, particularly on the phosphorus atom, have effected various levels of resistance to nucleases. However, while the ability of an antisense oligonucleotide to bind to specific DNA or RNA with fidelity is fundamental to antisense methodology, modified phosphorus oligonucleotides have generally suffered from inferior hybridization properties.

Replacement of the phosphorus atom has been an alternative approach in attempting to avoid the problems associated with modification on the pro-chiral phosphate moiety. For example, Matteucci, *Tetrahedron Letters* 1990, 31, 2385 discloses the replacement of the phosphorus atom with a methylene group. However, this replacement yielded unstable compounds with nonuniform insertion of formacetal linkages throughout their backbones. Cormier et al., *Nucleic Acids Research* 1988, 16, 4583, discloses replacement of phosphorus with a diisopropylsilyl moiety to yield homopolymers having poor solubility and hybridization properties. Stirchak et al., *Journal of Organic Chemistry* 1987, 52, 4202 discloses replacement of phosphorus linkages by short homopolymers containing carbamate or morpholino linkages to yield compounds having poor solubility and hybridization properties. Mazur et al., *Tetrahedron* 1984, 40, 3949, discloses replacement of a phosphorus linkage with a phosphonic linkage yielding a homotrimer. Goodchild, *Bioconjugate Chemistry* 1990, 1, 165, discloses ester linkages that are enzymatically degraded by esterases and, therefore, are not suitable for antisense applications.

Phosphonates are known in the literature but very few 3'-hydrogen phosphonates of nucleosides are known. Synthesis and use of 3'-methylene phosphonic acids and their esters as isosteres of nucleoside-3'-phosphates and phosphodiesters have been reported. Albrecht et al., *Tetrahedron*, 1984, 40, 79; Jones et al., *J. Am. Chem. Soc.,* 1970, 5510; Albrecht et al., *J. Am. Chem. Soc.,* 1970, 5511. All of these phosphonic acids and phosphonates bear 2'-hydroxy groups. Related 2'-hydroxy-3'-phosphonate analogs of nucleoside phosphates have been synthesized through a multistep synthetic procedure. Morr et al., *Z. Naturforsch.,* 1983, 38b, 1665; Morr and Ernst, *Liebigs Ann. Chemie,* 1993, 1205. 2'-Deoxy-thymidine-3'-methylene-hydrogen phosphonates have also been reported in WO97/32887 (Sep. 12, 1997).

Thus far only thymidine-3'-methylene hydrogen phosphonates have been reported. Furthermore, these phosphonates bear t-butyldiphenylsilyl protecting groups on the 5'-position which makes use of such phosphonates in conventional oligonucleotide synthesis cumbersome. There exists a need to provide isosteric 3'-methylene hydrogen phosphonate nucleosides that can bear a variety of substitutents at the 2'- and 5'-positions.

Phosphonates have been investigated because of their isosteric relationship with the natural phosphodiester linkage of oligonucleotides. Methyl phosphonates, in which one of the non-nucleosidic oxygen atoms of the natural phosphodiester linkage is replaced with a methyl group, have been studied widely. Related isosteres, where either the 3'- or the 5'-oxygen atom of the phosphodiester linkage is replaced with a methylene group, have also been investigated. Mazur et al. have reported the synthesis of a 3'-methylenephosphonate isostere of UpUpU (*Tetrahedron,* 1984, 40, 3949). This oligonucleotide is limited by the presence of 2'-hydroxy groups on all residues and by the tedious synthesis of the sugar-methylenephosphonate prior to attachment of a nucleosidic base. More recently, Heinemann et al. have reported the synthesis of 2'-deoxy-3'-methylenephosponate oligonucleotides and the effects of such a structural change on the conformation of an A-DNA octamer double helix (*Nucleic Acids Research,* 19, 427). 2'-Deoxy-thymidine-3'-methylene-hydrogen phosphonates have also been reported in WO97/32887 (published Sep. 12, 1997). Isosteric 5'-methylenephosphonate oligonucleotides have also been synthesized and reported to bind to complementary nucleic acids and be resistant to phosphodiesterases (Breaker et al., *Biochemistry,* 1993, 32, 9125).

Early attempts to synthesize phosphonate isosteres of nucleoside phosphates commenced with conversion of diacetone-D-glucose, through a series of ten reactions, into uridine-3'-methylene phosphonate protected at the 2-' and 5'-positions with hydroxyl groups (Mazur et al., *Tetrahedron,* 1984, 40, 3949). The key transformations entailed an Arbuzov reaction using triisopropyl phosphite to generate a ribofuranose-3'-methylenephosphonate, which was subsequently reacted with 1,2-bis(trimethylsiloxy) uracil and stannous chloride to afford the protected uridine-3'-methylene phosphonate.

More recently, Novartis has reported a multi-step procedure for the synthesis of 2'-deoxy-thymidine-3'-methylene hydrogen phosphonates (WO97/32887, published Sep. 12, 1997). Synthesis commences with 5'-protected thymidine (Derry et al., *Anti-Cancer Drug Design,* 1993, 8, 203; Mihkailov et al., *Nucleosides and Nucleotides,* 1996, 15, 1323), which is thiocarbonylated to afford the 5'-O-TBDPS-T-3'-thiocarbonate, using 3-t-butylphenoxy chlorothionoformate (Sanghvi et al., *Synthesis,* 1994, 1163). This thiocarbonate is reacted with tributylstannylstyrene (PhCH=CHSnBu₃) in the presence of AIBN, followed by oxidation of the 3'-alkenyl intermediate so generated using osmium tetroxide and sodium periodate, to afford 5'-O-TBDPS-T-3'-aldehyde (Lebreton et al., *Tetrahedron Letters,* 1994, 35, 5225; Sanghvi et al., *Synthesis,* 1994, 1163). Reduction of the 3'-aldehyde to the 3'-methanol derivative, followed by iodination using a phosphonium iodide afforded the key 5'-O-TBDPS-T-3'-methyl iodide intermediate (WO97/32887, published Sep. 12, 1997). This iodide was then subjected to a six-step sequence of reactions to convert the 3'-methyl iodide into the 3'-methylene hydrogen phosphonate group. The sequence consisted of sequential reactions with potassium hexamethyldisilazide and a H-phosphinate reagent, trimethylsilyl chloride for three days, titanium tetraisopropoxide, acetic acid and TBAF to deprotect the TBDPS group, tritylation using DMT-chloride, and finally hydrolysis using methanol/sodium methoxide or DBU. However, this monomer synthesis is lengthy and cumbersome, and has been proven effective for the synthesis of only 2'-deoxy-thymidine nucleosides.

Antisense therapy needs modified oligomers and oligonucleotides that bear a variety of nucleoside residues and diversity of modifications. A method for the convenient and efficient synthesis of a variety of nucleoside-3'-methylene hydrogen phosphonates is therefore needed. Further, these monomers need to be readily adaptable in oligonucleotide synthesis protocols.

Despite interest in isosteric oligonucleotides and methylenephosphonate oligomers, there has been no report of the successful synthesis and use of 2'-modified-3'-methylenephosphonate oligonucleotides capable of enhanced binding to complementary nucleic acids and exhibiting increased resistance to phosphodiesterases.

The limitations of available methods for modification of the phosphorus backbone have led to a continuing and long-felt need for other modifications which provide resistance to nucleases and satisfactory hybridization properties for antisense oligonucleotide diagnostics and therapeutics.

SUMMARY OF THE INVENTION

The present invention provides monomers having formula I:

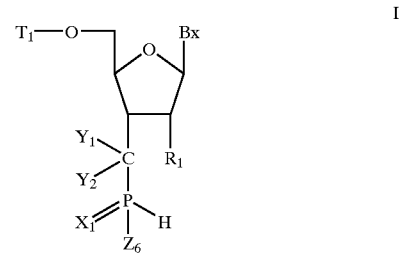

wherein:

$B_x$ is a protected or unprotected heterocyclic base moiety;

$T_1$ is an oligonucleotide, oligonucleoside, nucleoside, nucleotide, H or a hydroxyl protecting group;

$X_1$ is O, S or NH;

$R_1$ is $Z_0$—($C_2$–$C_{20}$ alkynyl);

$R_2$ is H, F, Cl, Br, I, alkyl, substituted alkyl, $(CH_2)_n$—$OCH_3$, $(CH_2)_n NH_2$ or $(CH_2)_a(Q_1)_b(Q_2)_c$;

or $R_1$ has one of formulas XI or XII:

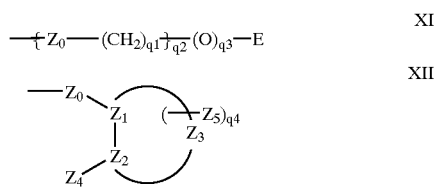

wherein:

$Z_0$ is O, S or NH;

E is $C_1$–$C_{10}$ alkyl, $N(Q_1)(Q_2)$ or $N=C(Q_1)(Q_2)$;

each $Q_1$ and $Q_2$ is, independently, H, $C_1$–$C_{10}$ alkyl, substituted alkyl, dialkylaminoalkyl, a nitrogen protecting group, a tethered or untethered conjugate group, a linker to a solid support;

or $Q_1$ and $Q_2$, together, are joined in a nitrogen protecting group or a ring structure that can include at least one additional heteroatom selected from N and O;

$q^1$ is from 1 to 10;

$q^2$ is from 1 to 10;

$q^3$ is zero or 1;

$q^4$ is zero, 1 or 2;

$q^5$ is 1 to 10;

each $M_1$ is, independently, H, $C_1$–$C_8$ alkyl, $C_1$–$C_8$ haloalkyl, $C(=NH)N(H)M_2$, $C(=O)N(H)M_2$ or $OC(=O)N(H)M_2$;

$M_2$ is H or $C_1$–$C_8$ alkyl;

$Z_1$, $Z_2$ and $Z_3$ comprise a ring system having from about 4 to about 7 carbon atoms or having from about 3 to about 6 carbon atoms and 1 or 2 heteroatoms wherein said heteroatoms are selected from oxygen, nitrogen and sulfur and wherein said ring system is aliphatic, unsaturated aliphatic, aromatic, or saturated or unsaturated heterocyclic; and $Z_4$ is $OM_1$, $SM_1$, or $N(M_1)_2$;

$Z_5$ is alkyl or haloalkyl having 1 to about 10 carbon atoms, alkenyl having 2 to about 10 carbon atoms, alkynyl having 2 to about 10 carbon atoms, aryl having 6 to about 14 carbon atoms, $N(Q_1)(Q_2)$, $OQ_1$, halo, $SQ_1$ or CN;

$Z_6$ is OH, $OCH_2CH_2CN$, $N(i\text{-}Pr)_2$, dialkylamino, disubstituted alkylalmino or $O^-HB_y^+$;

$B_y$ is an organic base moiety;

each of $Y_1$ and $Y_2$ is, independently, H, alkyl, substituted alkyl, aryl, substituted aryl, heterocyclyl, substituted heterocyclyl, cyano, carboxyl, ester or a cyclic moiety; and m is 0 or 1.

The present invention also provides oligomers of formula II:

wherein:

$B_x$ is a protected or unprotected heterocyclic base moiety;

$T_1$ is an oligonucleotide, oligonucleoside, nucleoside, nucleotide, H or a hydroxyl protecting group;

each of $X_1$, $X_2$ and $X_3$ is, independently, O, S or NH;

L is $C(Y_1)(Y_2)$ or O, provided that at least one L is $C(Y_1)(Y_2)$;

$R_1$ is $Z_0$—($C_2$–$C_{20}$ alkynyl);

or $R_1$ has one of formulas XI or XII:

$$\text{—}[Z_0\text{—}(CH_2)_{q1}]_{q2}(O)_{q3}\text{—}E \quad \text{XI}$$

XII wherein:

$Z_0$ is O, S or NH;

E is $C_1$–$C_{10}$ alkyl, $N(Q_1)(Q_2)$ or $N=C(Q_1)(Q_2)$;

each $Q_1$ and $Q_2$ is, independently, H, $C_1$–$C_{10}$ alkyl, substituted alkyl, dialkylaminoalkyl, a nitrogen protecting group, a tethered or untethered conjugate group, a linker to a support;

or $Q_1$ and $Q_2$, together, are joined in a nitrogen protecting group or a ring structure that can include at least one additional heteroatom selected from N and O;

$q^1$ is from 1 to 10;

$q^2$ is from 1 to 10;

$q^3$ is zero or 1;

$q^4$ is zero, 1 or 2;

$q^5$ is 1 to 10;

each $M_1$ is, independently, H, $C_1$–$C_8$ alkyl, $C_1$–$C_8$ haloalkyl, $C(=NH)N(H)M_2$, $C(=O)N(H)M_2$ or $OC(=O)N(H)M_2$;

$M_2$ is H or $C_1$–$C_8$ alkyl;

$Z_1$, $Z_2$ and $Z_3$ comprise a ring system having from about 4 to about 7 carbon atoms or having from about 3 to about 6 carbon atoms and 1 or 2 heteroatoms wherein said heteroatoms are selected from oxygen, nitrogen and sulfur and wherein said ring system is aliphatic, unsaturated aliphatic, aromatic, or saturated or unsaturated heterocyclic; and $Z_4$ is $OM_1$, $SM_1$, or $N(M_1)_2$;

$Z_5$ is alkyl or haloalkyl having 1 to about 10 carbon atoms, alkenyl having 2 to about 10 carbon atoms, alkynyl having 2 to about 10 carbon atoms, aryl having 6 to about 14 carbon atoms, $N(Q_1)(Q_2)$, $OQ_1$, halo, $SQ_1$ or CN;

m is 0 or 1;

p is 0 or an integer from 1 to 50; and each of $Y_1$ and $Y_2$ is, independently, H, alkyl, substituted alkyl, aryl, substituted aryl, heterocyclyl, substituted heterocyclyl, cyano, carboxyl, ester or a cyclic moiety.

The present invention further provides methods of preparing monomers of formula I:

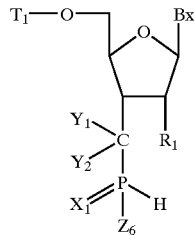

wherein:
- $B_x$ is a protected or unprotected heterocyclic base moiety;
- $T_1$ is an oligonucleotide, oligonucleoside, nucleoside, nucleotide, H or a hydroxyl protecting group;
- $X_1$ is O, S or NH;
- $R_1$ is $Z_0$—($C_2$–$C_{20}$ alkynyl);
- or $R_1$ has one of formulas XI or XII:

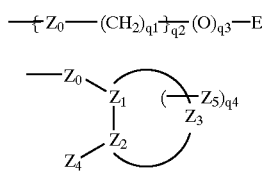

wherein:
- $Z_0$ is O, S or NH;
- E is $C_1$–$C_{10}$ alkyl, $N(Q_1)(Q_2)$ or $N{=}C(Q_1)(Q_2)$;
- each $Q_1$ and $Q_2$ is, independently, H, $C_1$–$C_{10}$ alkyl, substituted alkyl, dialkylaminoalkyl, a nitrogen protecting group, a tethered or untethered conjugate group, a linker to a solid support;
- or $Q_1$ and $Q_2$, together, are joined in a nitrogen proctecting group or a ring structure that can include at least one additional heteroatom selected from N and O;
- $q^1$ is from 1 to 10;
- $q^2$ is from 1 to 10;
- $q^3$ is zero or 1;
- $q^4$ is zero, 1 or 2;
- $q^5$ is 1 to 10;
- each $M_1$ is, independently, H, $C_1$–$C_8$ alkyl, $C_1$–$C_8$ haloalkyl, $C({=}NH)N(H)M_2$, $C({=}O)N(H)M_2$ or $OC({=}O)N(H)M_2$;
- $M_2$ is H or $C_1$–$C_8$ alkyl;
- $Z_1$, $Z_2$ and $Z_3$ comprise a ring system having from about 4 to about 7 carbon atoms or having from about 3 to about 6 carbon atoms and 1 or 2 heteroatoms wherein said heteroatoms are selected from oxygen, nitrogen and sulfur and wherein said ring system is aliphatic, unsaturated aliphatic, aromatic, or saturated or unsaturated heterocyclic; and
- $Z_4$ is $OM_1$, $SM_1$, or $N(M_1)_2$;
- $Z_5$ is alkyl or haloalkyl having 1 to about 10 carbon atoms, alkenyl having 2 to about 10 carbon atoms, alkynyl having 2 to about 10 carbon atoms, aryl having 6 to about 14 carbon atoms, $N(Q_1)(Q_2)$, $OQ_1$, halo, $SQ_1$ or CN;
- $Z_6$ is OH, $OCH_2CH_2CN$, $N(i\text{-}Pr)_2$, dialkylamino, disubstituted alkylamino or $O^-HB_y^+$;
- m is 0 or 1;

each of $Y_1$ and $Y_2$ is, independently, H, alkyl, substituted alkyl, aryl, substituted aryl, heterocyclyl, substituted heterocyclyl, cyano, carboxyl, ester or a cyclic moiety; and $B_y$ is an organic base moiety; comprising the steps of:
(a) providing a 5'-protected-3'-substituted alkyl nucleoside of formula III:

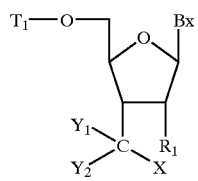

wherein X is a leaving group;
(b) reacting the nucleoside of formula III with bis(trimethylsilyl)phosphonite;
(c) concentrating the product of step (b);
(d) adding methanolic solvent to the product of step (c) to form a solution; and
(e) concentrating said solution.

The present invention further provides methods of preparing monomers of formula I:

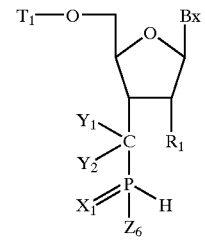

wherein:
- $B_x$ is a protected or unprotected heterocyclic base moiety;
- $T_1$ is an oligonucleotide, oligonucleoside, nucleoside, nucleotide, H or a hydroxyl protecting group;
- $X_1$ is O, S or NH;
- $R_1$ is $Z_0$—($C_2$–$C_{20}$ alkynyl);
- or $R_1$ has one of formulas XI or XII:

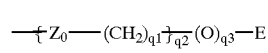

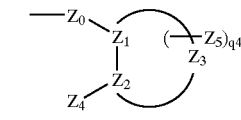

wherein:
- $Z_0$ is O, S or NH;
- E is $C_1$–$C_{10}$ alkyl, $N(Q_1)(Q_2)$ or $N{=}C(Q_1)(Q_2)$;
- each $Q_1$ and $Q_2$ is, independently, H, $C_1$–$C_{10}$ alkyl, substituted alkyl, dialkylaminoalkyl, a nitrogen protecting group, a tethered or untethered conjugate group, a linker to a solid support;
- or $Q_1$ and $Q_2$, together, are joined in a nitrogen protecting group or a ring structure that can include at least one additional heteroatom selected from N and O;
- $q^1$ is from 1 to 10;

$q^2$ is from 1 to 10;
$q^3$ is zero or 1;
$q^4$ is zero, 1 or 2;
$q^5$ is 1 to 10;
each $M_1$ is, independently, H, $C_1$–$C_8$ alkyl, $C_1$–$C_8$ haloalkyl, $C(=NH)N(H)M_2$, $C(=O)N(H)M_2$ or $OC(=O)N(H)M_2$;
$M_2$ is H or $C_1$–$C_8$ alkyl;
$Z_1$, $Z_2$ and $Z_3$ comprise a ring system having from about 4 to about 7 carbon atoms or having from about 3 to about 6 carbon atoms and 1 or 2 heteroatoms wherein said heteroatoms are selected from oxygen, nitrogen and sulfur and wherein said ring system is aliphatic, unsaturated aliphatic, aromatic, or saturated or unsaturated heterocyclic; and
$Z_4$ is $OM_1$, $SM_1$, or $N(M_1)_2$;
$Z_5$ is alkyl or haloalkyl having 1 to about 10 carbon atoms, alkenyl having 2 to about 10 carbon atoms, alkynyl having 2 to about 10 carbon atoms, aryl having 6 to about 14 carbon atoms, $N(Q_1)(Q_2)$, $OQ_1$, halo, $SQ_1$ or CN;
$Z_6$ is OH, $OCH_2CH_2CN$, $N(i-Pr)_2$, dialkylamino, disubstituted alkylamino or $O^-HB_y^+$;
m is 0 or 1;
each of $Y_1$ and $Y_2$ is, independently, H, alkyl, substituted alkyl, aryl, substituted aryl, heterocyclyl, substituted heterocyclyl, cyano, carboxyl, ester or a cyclic moiety; and
$B_y$ is an organic base moiety; comprising the steps of:
(a) providing a 5'-protected-3'-hydroxy alkyl nucleoside of formula IV:

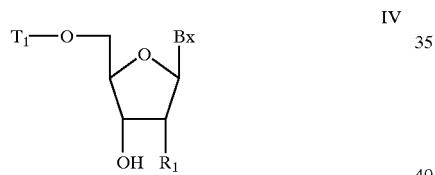

IV (b) oxidizing said nucleoside to form an oxidized nucleoside;
(c) alkenylating said oxidized nucleoside with a Wittig reagent to form a 3'-substituted nucleoside;
(d) phosphonylating said 3'-substituted nucleoside; and
(e) protecting the 5'-hydroxy group of said 3'-substituted nucleoside.

Also provided are methods for preparing oligomers of formula II:

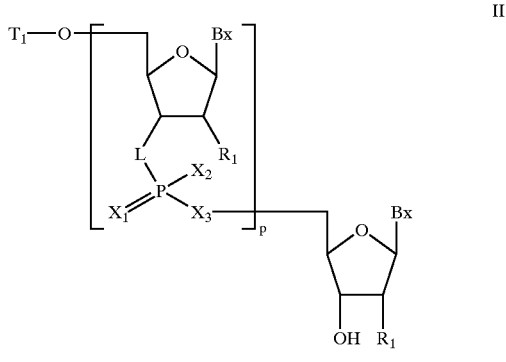

II wherein:
$B_x$ is a protected or unprotected heterocyclic base moiety;
$T_1$ is an oligonucleotide, oligonucleoside, nucleoside, nucleotide, H or a hydroxyl protecting group;
each of $X_1$, $X_2$ and $X_3$ is, independently, O, S or NH;
L is $C(Y_1)(Y_2)$ or O, provided that at least one L is $C(Y_1)(Y_2)$;
$R_1$ is $Z_0$—($C_2$–$C_{20}$ alkynyl)
or $R_1$ has one of formulas XI or XII:

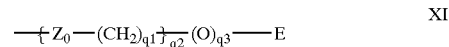

XI

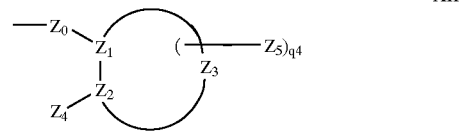

XII wherein:
$Z_0$ is O, S or NH;
E is $C_1$–$C_{10}$ alkyl, $N(Q_1)(Q_2)$ or $N=C(Q_1)(Q_2)$;
each $Q_1$ and $Q_2$ is, independently, H, $C_1$–$C_{10}$ alkyl, substituted alkyl, dialkylaminoalkyl, a nitrogen protecting group, a tethered or untethered conjugate group, a linker to a solid support;
or $Q_1$ and $Q_2$, together, are joined in a nitrogen protecting group or a ring structure that can include at least one additional heteroatom selected from N and O;
$q^1$ is from 1 to 10;
$q^2$ is from 1 to 10;
$q^3$ is zero or 1;
$q^4$ is zero, 1 or 2;
$q^5$ is 1 to 10;
each $M_1$ is, independently, H, $C_1$–$C_8$ alkyl, $C_1$–$C_8$ haloalkyl, $C(=NH)N(H)M_2$, $C(=O)N(H)M_2$ or $OC(=O)N(H)M_2$;
$M_2$ is H or $C_1$–$C_8$ alkyl;
$Z_1$, $Z_2$ and $Z_3$ comprise a ring system having from about 4 to about 7 carbon atoms or having from about 3 to about 6 carbon atoms and 1 or 2 heteroatoms wherein said heteroatoms are selected from oxygen, nitrogen and sulfur and wherein said ring system is aliphatic, unsaturated aliphatic, aromatic, or saturated or unsaturated heterocyclic; and
$Z_4$ is $OM_1$, $SM_1$, or $N(M_1)_2$;
$Z_5$ is alkyl or haloalkyl having 1 to about 10 carbon atoms, alkenyl having 2 to about 10 carbon atoms, alkynyl having 2 to about 10 carbon atoms, aryl having 6 to about 14 carbon atoms, $N(Q_1)(Q_2)$, $OQ_1$, halo, $SQ_1$ or CN;
m is 0 or 1;
p is 0 or an integer from 1 to 50; and
each of $Y_1$ and $Y_2$ is, independently, H, alkyl, substituted alkyl, aryl, substituted aryl, heterocyclyl, substituted heterocyclyl, cyano, carboxyl, ester or a cyclic moiety; comprising the steps of:
(a) providing a 5'-protected nucleoside attached to a solid support;
(b) cleaving the 5'-protecting group in the presence of an acid solution to form a 5'-deprotected nucleoside;

(c) coupling said 5'-deprotected nucleoside with a monomer of formula I:

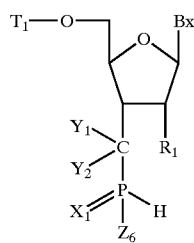

wherein:

$Z_6$ is OH, $OCH_2CH_2CN$, $N(i-Pr)_2$, dialkylamino, disubstituted alkylamino or $O^-HB_y^+$;

each of $Y_1$ and $Y_2$ is, independently, H, alkyl, substituted alkyl, aryl, substituted aryl, heterocyclyl, substituted heterocyclyl, cyano, carboxyl, ester or a cyclic moiety; and $B_y$ is an organic base moiety;

in the presence of a condensing agent to form a compound having an H-phosphonate linkage;

(d) optionally capping unreacted 5'-hydroxy groups using isopropyl phosphite and pivaloyl chloride in acetonitrile and pyridine;

(e) repeating steps (b) to (d) to form an oligomer of desired length and composition;

(f) oxidizing said H-phosphonate linkage with an oxidizing reagent to form an oxidized methylenephosphonate linkage;

(g) repeating steps (b) to (f) to form an oligomer of desired length and composition; and (h) cleaving said oligomer with aqueous ammonia.

In a preferred embodiment the condensing reagent is a solution of 2-chloro-5,5-dimethyl-2-oxo-1,3,2-dioxaphosphinane in an organic solvent and the oxidizing reagent is a mixture of camphorsulfonyloxaziridine (CSO) and N, O-bis(trimethylsilyl)acetamide in an organic solvent.

DETAILED DESCRIPTION OF PREFERRED EMBODIMENTS

Figure 1:
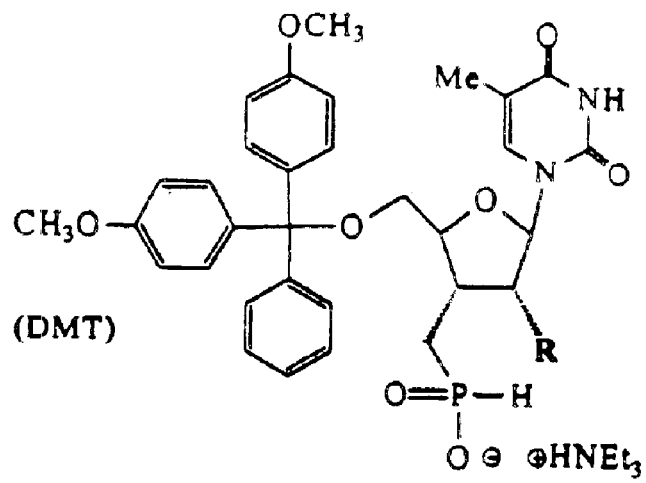
FIG. 1 shows the structure of compounds 32, 44, 44a, 66 and 50–53.
Figure 1:
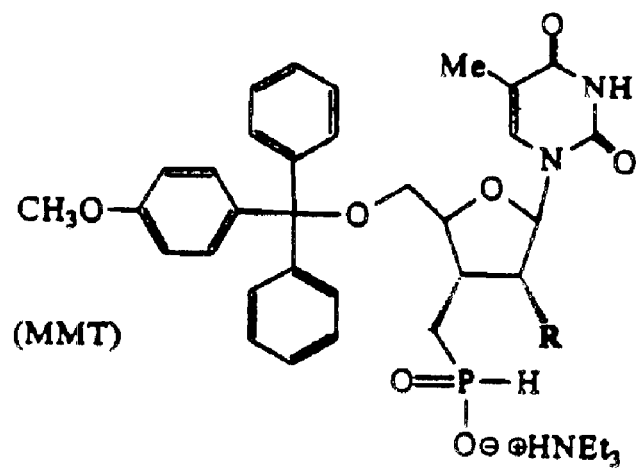
Figure 2:
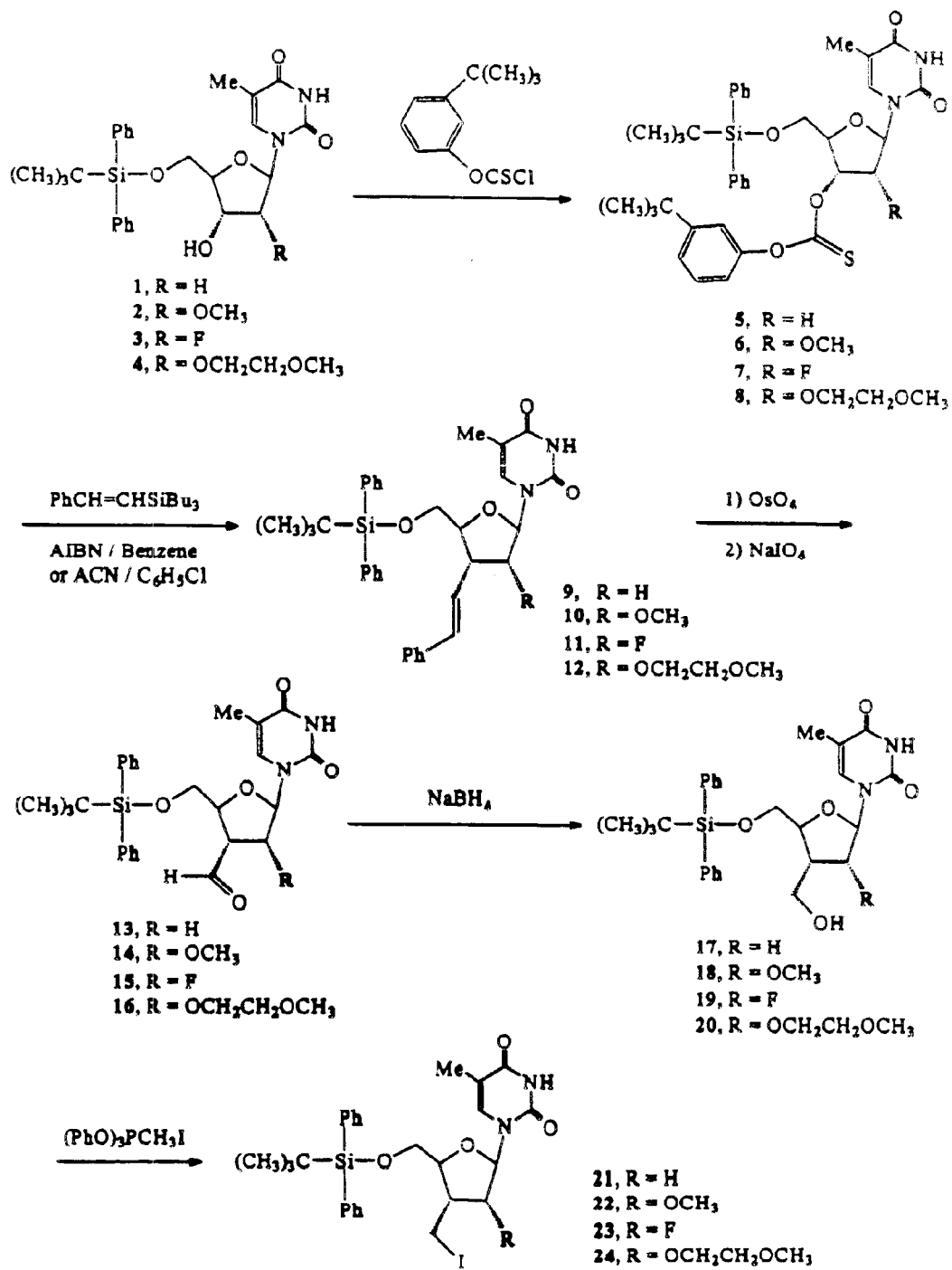
FIG. 2 is a schematic showing the synthesis of compounds 21–24.
Figure 3:
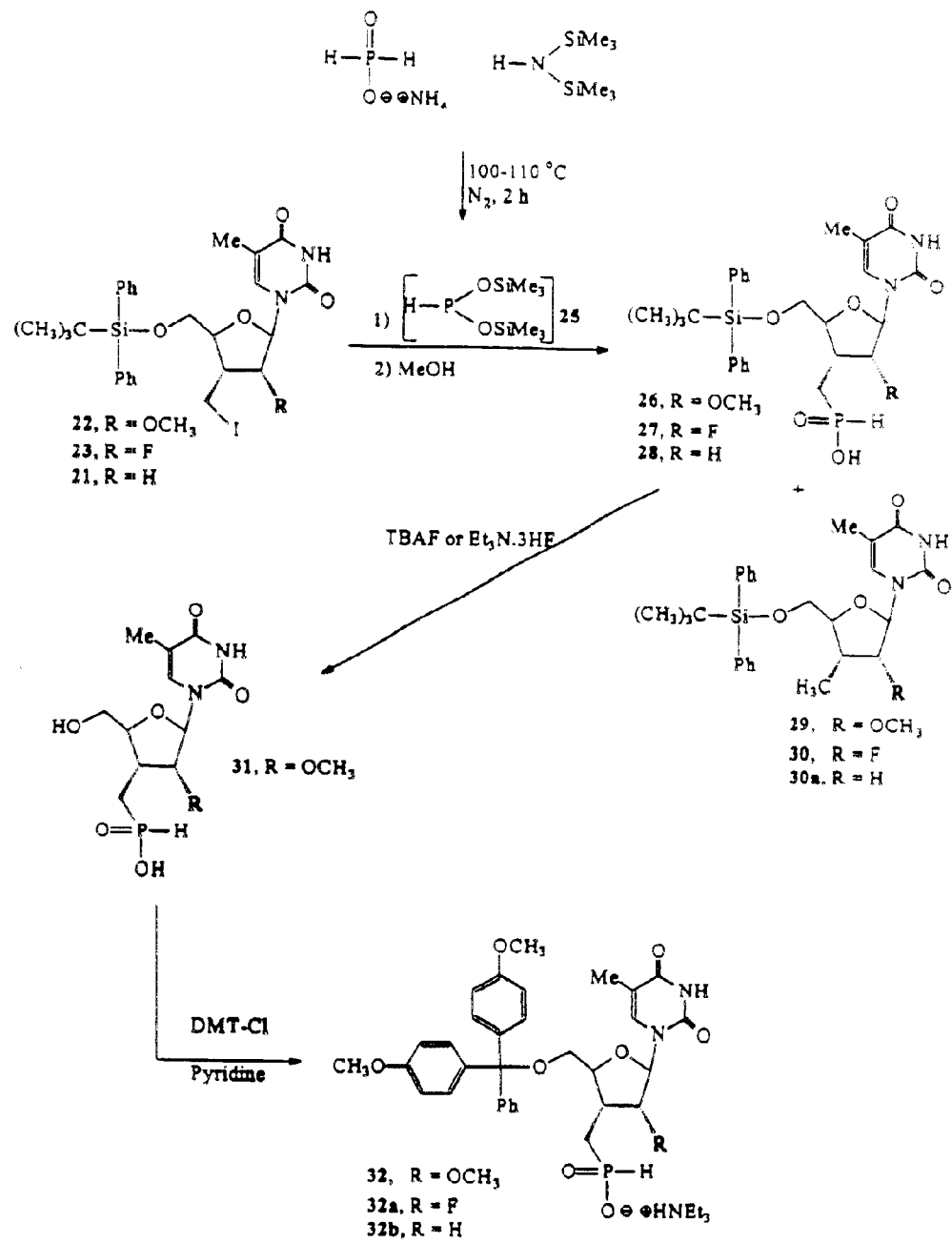
FIG. 3 is a schematic showing the synthesis of compounds 32, 32a and 32b.
Figure 4:
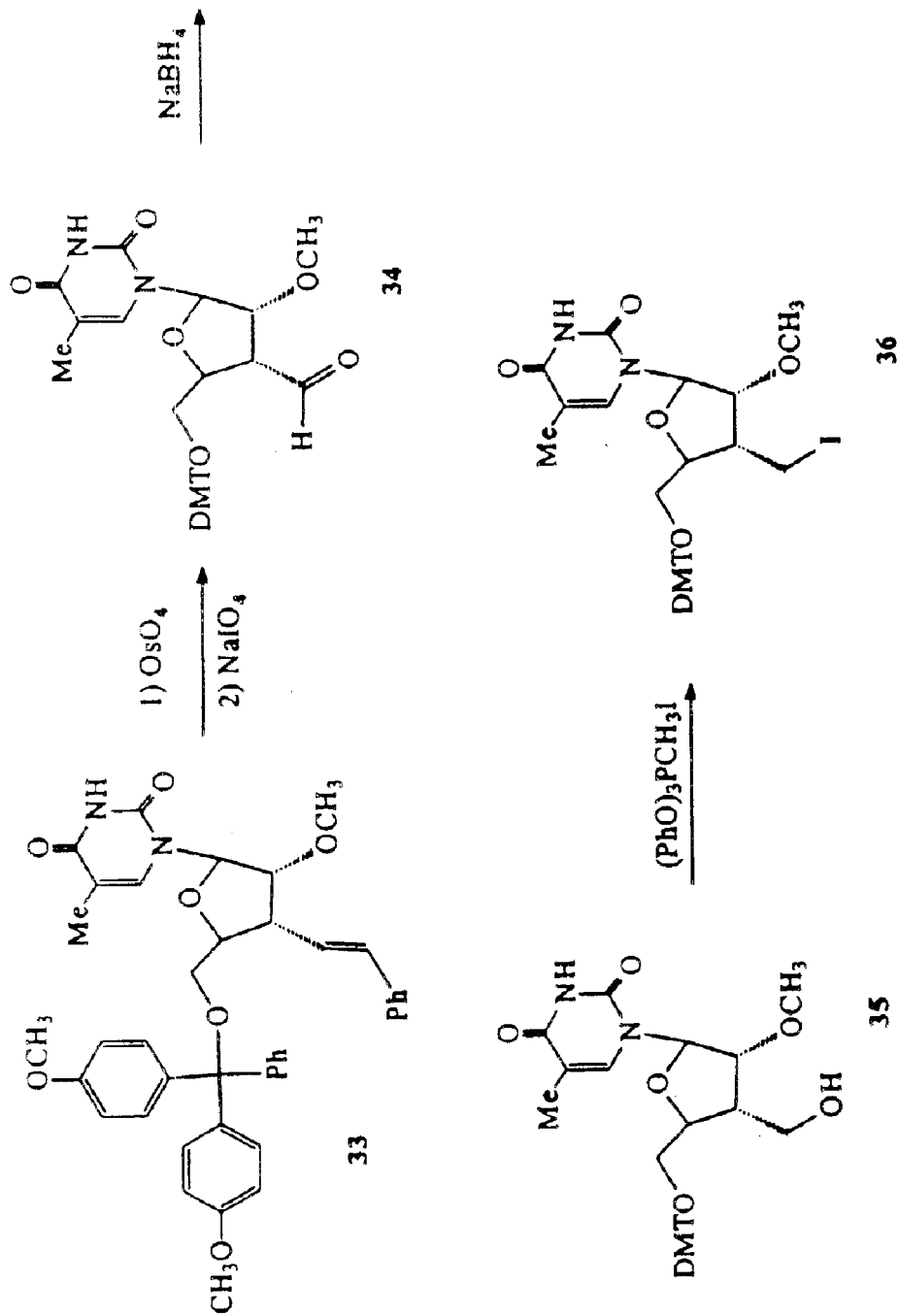
FIG. 4 is a schematic showing the synthesis of compounds 36.
Figure 5:
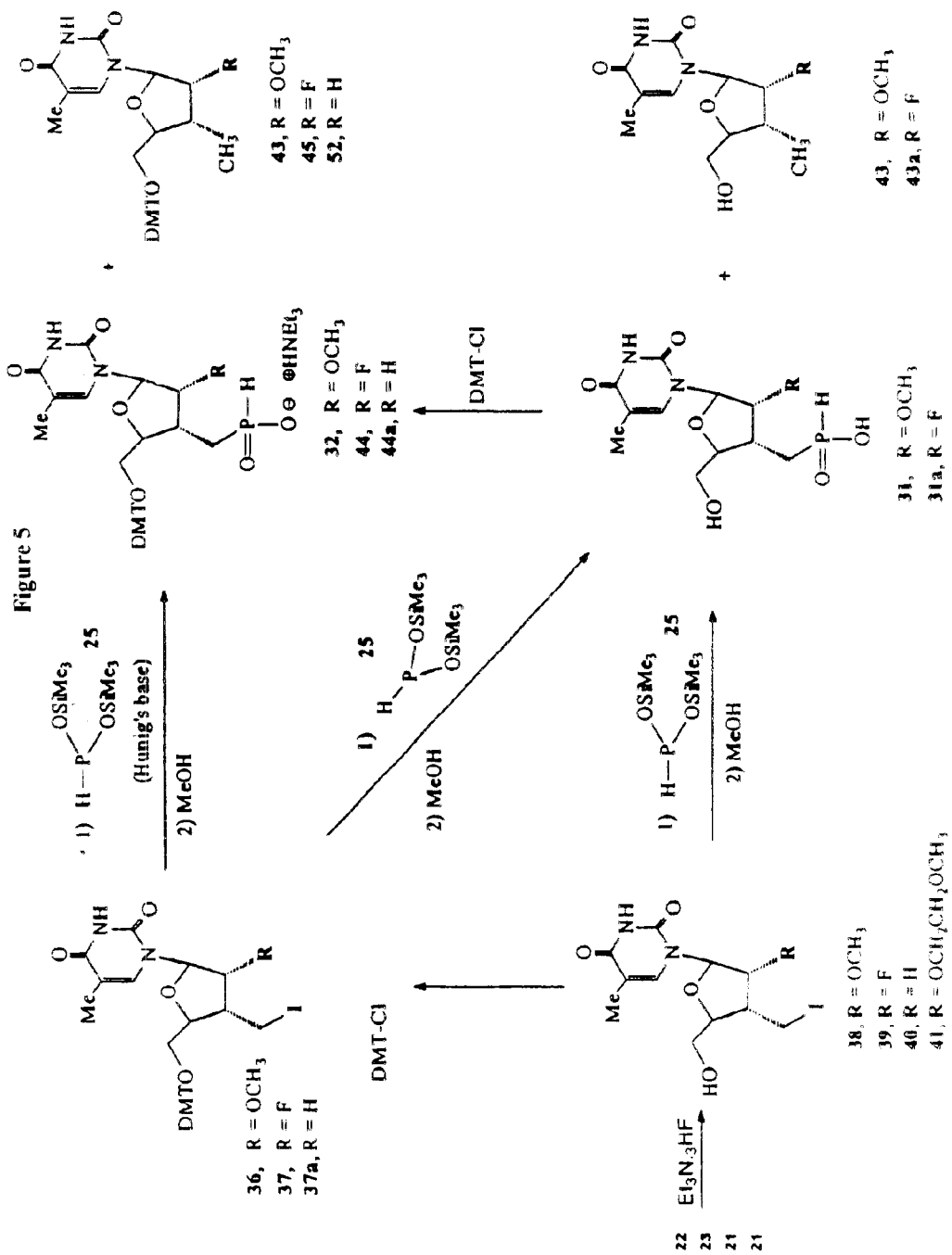
FIG. 5 is a schematic showing the synthesis of compounds 32, 44a and 44b.
Figure 6:
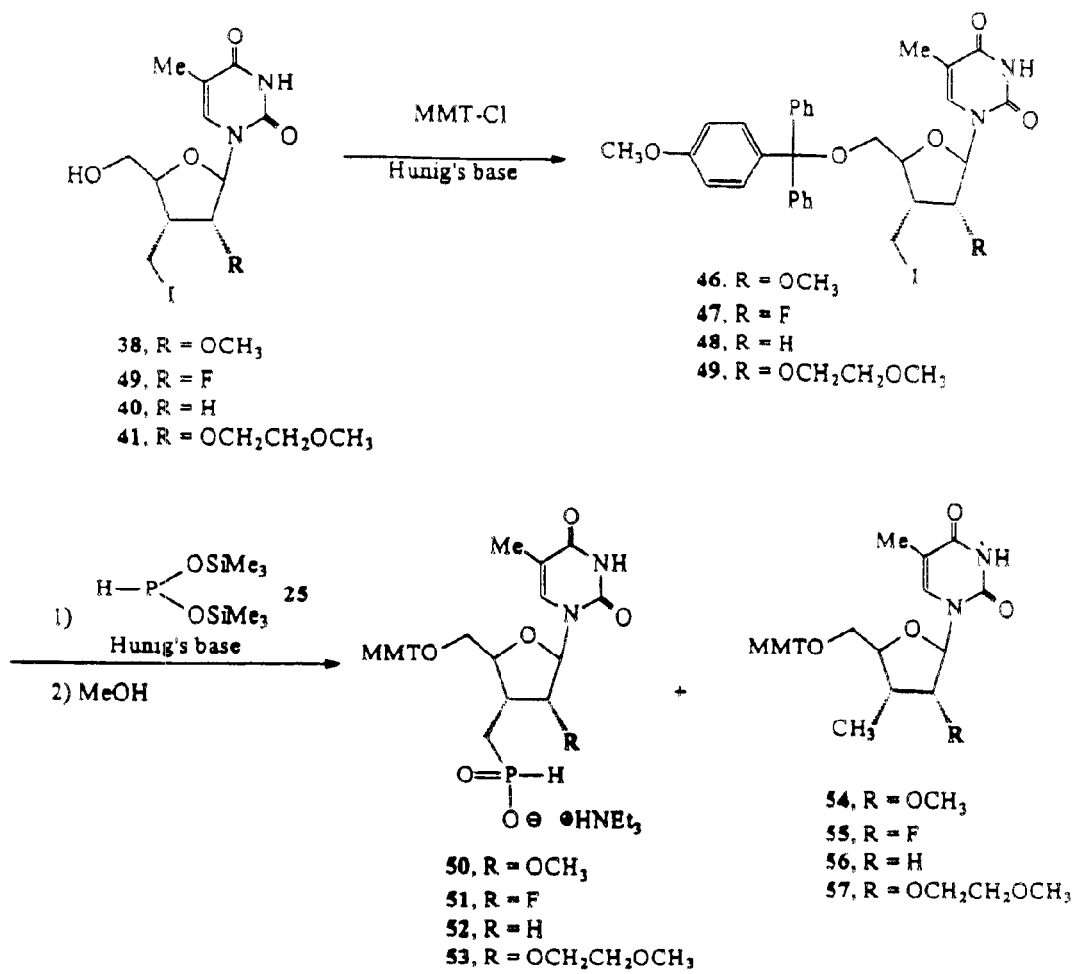
FIG. 6 is a schematic showing the synthesis of compounds 50–57.
Figure 7:
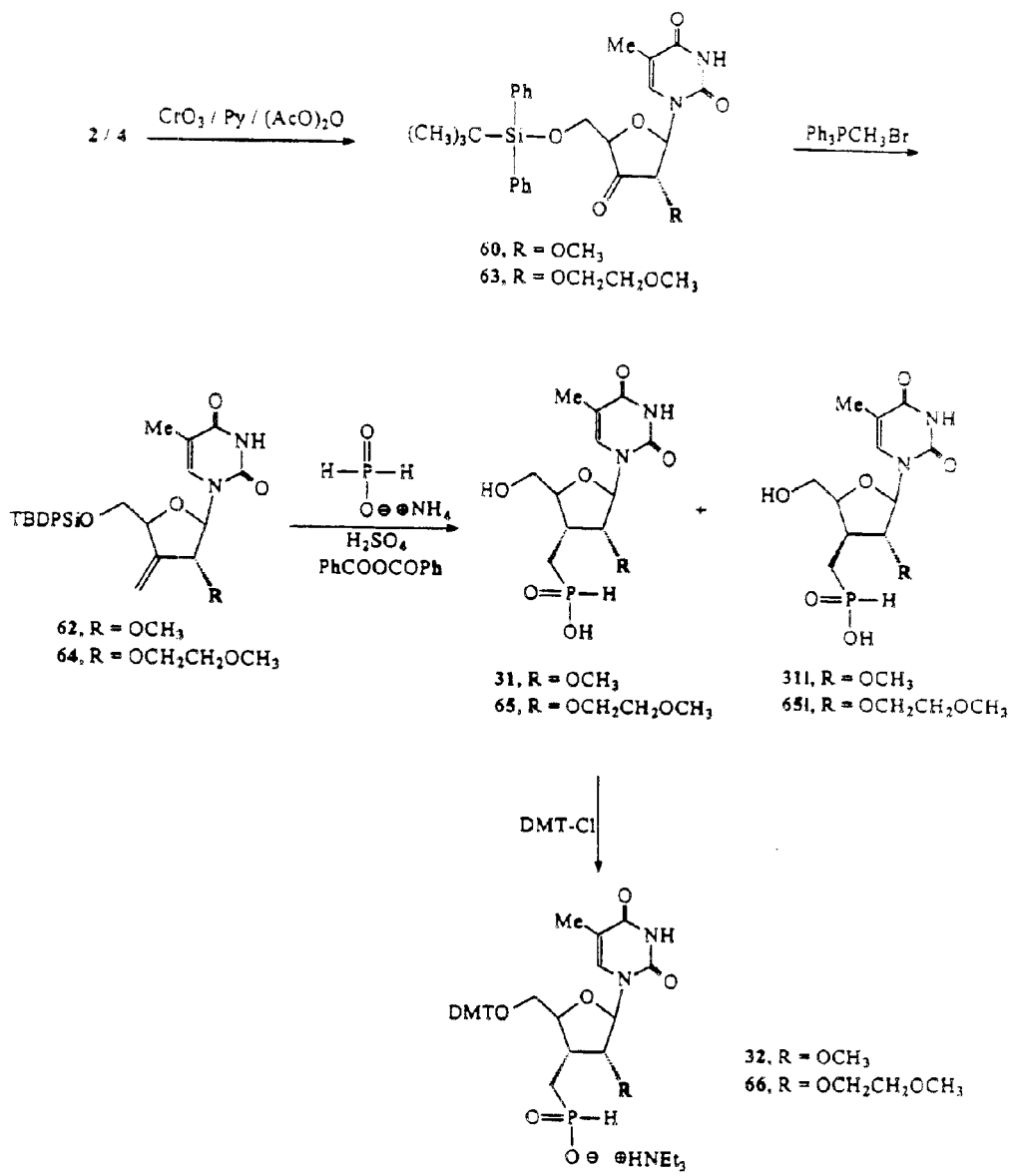
FIG. 7 is a schematic showing the synthesis of compounds 32 and 66.
Figure 8:
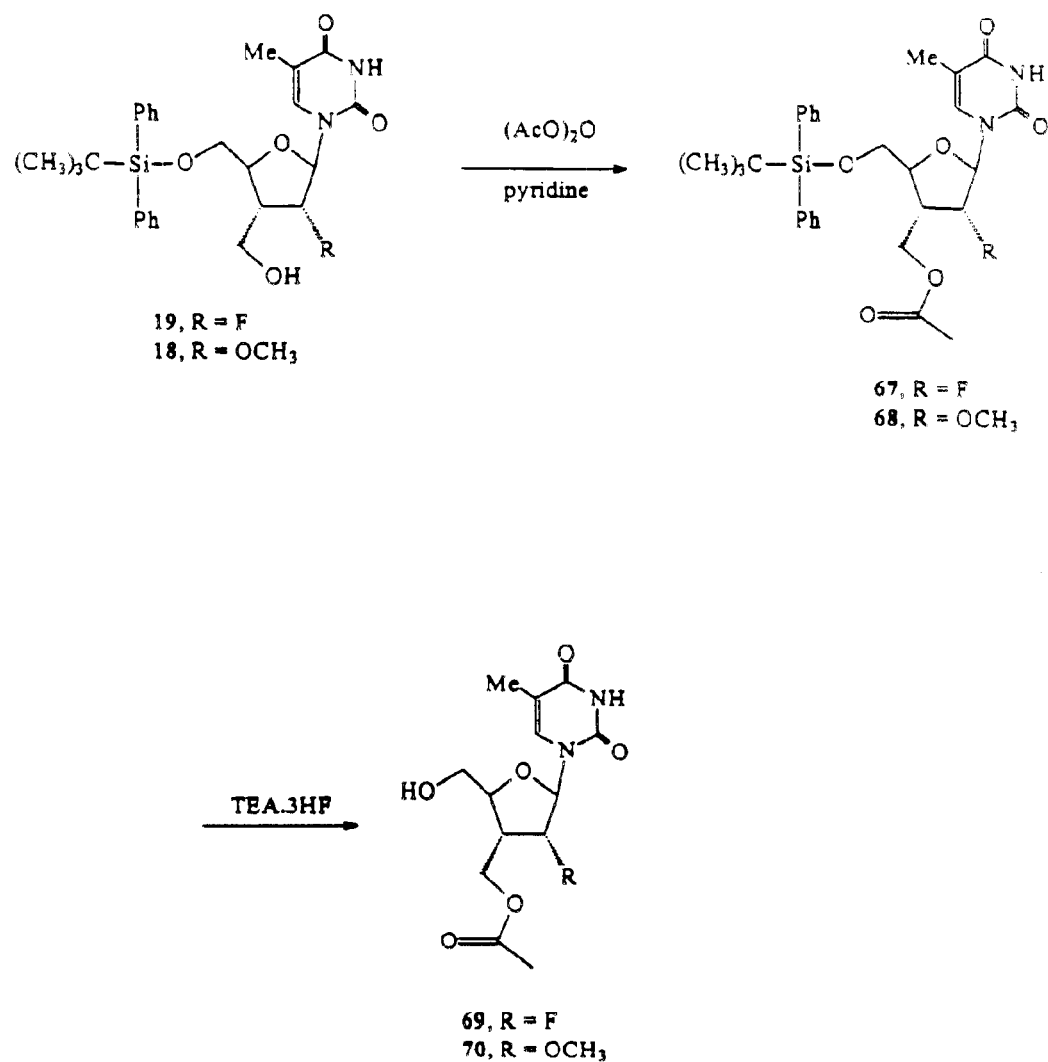
FIG. 8 is a schematic showing the synthesis of compounds 69 and 70.

The monomers of the present invention are modified nucleosides that bear a hydrogen phosphonate or related moiety attached via a methylene or substituted methylene group to the 3'-position of the nucleoside. These monomers include modified nucleosides having a natural or non-natural heterocyclic base moiety which may optionally be protected. These monomers may be substituted at the 5'-position where they may bear one of a variety of substituents including, but not limited to, hydroxyl, silyl or trityl hydroxyl protecting groups, oligonucleosides, and oligonucleotides. The monomers of the invention may also be substituted at the 2'-position where they may bear one of a variety of substituents including, but not limited to, substituted or unsubstituted alkyl, alkoxy, alkoxyalkoxy, alkylamimino or halo groups.

The oligomers of the present invention are modified oligonucleotides that bear 3'-methylene phosphonate or phosphodiester linkages between constituent monomer nucleoside units. The monomers comprising the oligomers of the present invention may be natural or non-natural, substituted or unsubstituted, modified or unmodified, protected or unprotected, and isomers. Modified methylene phosphonate monomer nucleoside units of the oligomers of the present invention include structural modifications to the base or sugar moieties of the nucleoside. Sugar modifications include alterations in the size and substitution of the natural ribose sugar including, but not limited to, hexose, 2'-deoxy, 2'-halo, 2'-alkyl, 2'-alkoxy, 3'-thio, 3'methylene, 5'-thio, 5'-methylene, 5'-deoxy groups. Preferably, oligomers of the present invention bear 3'-methylene substitutions on the modified nucleoside. Preferably, such modified nucleosides in the oligomers of the present invention also bear 2'-modifications including, but not limited to, 2'-deoxy, 2'-halo, and 2'-substituted or unsubstituted alkoxy groups. The oligomers of the present invention comprise at least one 3'-methylene phosphonate linkage. The oligomers of the present invention may also comprise only 3'-methylene phosphonate linkages. Methylene phosphonate linkages in the oligomers of the present invention may be located in a block of nucleoside monomer units (gapmers or blockmers), at one or both ends of an oligomer (wingmers) or be randomly dispersed within the oligomer.

Monomer compounds of formula I are synthesized from nucleoside compounds of formula III. The 5'-protected-3-substituted alkyl-nucleoside of formula III is added to a vessel containing bis(trimethylsilyl)phosphonite (BTSP) at −5 to 0° C. and allowed to react at room temperature for several hours. The reaction is facile in phosphonylating at the 3'-position while also reducing the 3'-position. The reaction product is subsequently hydrolyzed using an alcoholic solution or water to afford the desired 3'-methylene hydrogen phosphonic acid which may be readily isolated by chromatography. Ion-exchange chromatography may be used to isolate the product as the 3'-methylene hydrogen phosphonate salt.

Typically the Arbuzov reaction used in the method of the present invention affords a mixture of the nucleoside-3'-methylene hydrogen phosphonate derivative and the 3'-methyl-nucleoside. Phosphonylation in the presence of a base such as, but not limited to, diisopropylethylamine, improves the yield of the desired 3'-methylene hydrogen phosphonate, and is preferred. The Arbuzov reaction using BTSP may be carried out with a variety of groups present at the 2'-, 3'- or 5'-positions of natural and non-natural nucleoside whose heterocyclic bases moieties may or may not be protected.

BPTS used in the method of the present invention may be prepared via either of two procedures: reaction of bis(trimethylsilyl) amine with ammonium phosphinate (Montchamp, *J. Org. Chem.*, 1995, 60, 6076), or by reaction of trimethylsilyl chloride with triethylammonium phosphinate. The present invention also provides an alternate method for the synthesis of the monomers of the present invention from a 5'-protected-3'-hydroxy nucleoside of formula IV. Oxidation of the 3'-hydroxyl functional group is accomplished using chromium trioxide in pyridine and acetic anhydride to afford the 5'-protected-3'-oxo-nucleoside derivative. The 3'-carbonyl group is next reacted with a Wittig reagent such as, but not limited to, methyl triphenylphosphonium bromide, to generate an exocyclic double bond at the 3'-position, which is subsequently phosphonylated using sodium hypophosphite in a mixture with sulfuric acid and benzoyl peroxide, to afford the 3'-methylene hydrogen phosphonate. However, the acidic conditions of the reaction cleave any acid labile protecting group, if present, on the 5'-hydroxyl group of the nucleoside. Therefore, the phosphonate product is finally reacted with a hydroxyl protecting group to afford the monomer nucleoside-3'-methylene hydrogen phosphonate of the present invention. This method is versatile in that it can tolerate a wide variety of heterocyclic bases and substituents at the 2'- and 5'-positions of the nucleoside. This method of synthesis is also short and efficient.

Synthesis of oligomers of the present invention begins with selection of a nucleoside bound to a solid support. This nucleoside is chosen to be the 3'-terminus of the oligomer. Oligonucleotide synthesis proceeds along the following general scheme: deprotecting the 5'-protecting group, coupling with an activated nucleotide building block, optionally capping any unreacted monomer, repeating the steps of deprotecting, coupling and capping to generate the oligomer of desired length and sequence, oxidizing the resulting internucleoside linkages, in the case of segmental synthesis of the oligomer having different backbone modifications repeating the steps of deprotecting, coupling, capping and oxidizing to generate the full length oligomer, cleaving (which also includes deprotecting, i.e., removal of protecting groups present), and purifying and isolating the oligomer.

Solid phase synthesis of oligomers of the present invention follows conventional oligonucleotide synthesis protocol used for the preparation of phosphodiester oligonucleotides using H-phosphonate chemistry. Three significant improvements are made in this process. First, coupling of nucleoside-3'-methylene hydrogen phosphonate monomers has been improved by using 2-chloro-5,5-dimethyl-2-oxo-1,3,2-dioxaphosphinane (NEP-Cl) as the condensing agent. This is a superior procedure to the conventionally used pivaloyl chloride. Analysis of the activation and reaction kinetics, and coupling yields of thymidine-3'-methylene hydrogen phosphonate using a panel of activators that included pivaloyl chloride (Piv-Cl), bromo-trispyrrolidinophosphonium hexafluorophosphate (PyBroP), bis(2-oxo-3-oxazolidinyl)phosphinic chloride (BOP-Cl), and NEP-Cl in the presence and absence of dimethylamino pyridine (DMAP), revealed NEP-Cl to be the preferred condensing reagent. Preferably, 60–80 equivalents of NEP-Cl are used with 15–20 equivalents of nucleoside hydrogen phosphonate monomer in a coupling reaction having a duration of 10 minutes.

Second, oxidation of the hydrogen phosphonate linkage formed via coupling has been improved by using an oxidizing reagent comprising a 0.2 M solution of camphorsulfonyl oxaziridine (CSO) and 0.5 M N,O-bis(trimethylsilyl) acetamide (BSA) in acetonitrile. The oxidation reaction has a duration of approximately 2 hours. This is followed by conventional oxidation using 0.2M iodine in a mixture of pyridine and water (98:2) for 30 minutes. This modified oxidation procedure affords superior oxidation of the methylene phosphonate internucleoside linkages of the oligomers of the present invention.

Third, introduction of methylene thiophqsphonate linkages via sulfurization of the hydrogen phosphonate linkages has been achieved by using an oxidizing reagent comprising a solution of 3H-1,2-benzodithiol-3-one-1,1-dioxide and N,O-bis(trimethylsilyl)acetamide in pyridine/acetonitrile. The duration of the oxidation reaction is about 12 hours. Alternatively, a solution of 10% elemental sulfur in carbondisulfide/pyridine/triethylamine (35/35/1) can be used for sulfurization of 3'-methylene-H-phosphonate linkages.

As used herein, "C3'-methylene phosphonate linkage" or "methylene phosphonate linkage" means a phosphorus-containing linkage between two nucleosides wherein the 3'-O atom of the ribofuranosyl moiety is replaced with a methylene or a substituted methylene group. This linkage is an alkyl phosphomonoester linkage wherein the oxygen atom connecting the phosphorus atom of the linkage to C3' of the sugar moiety is replaced with a methylene or a substituted methylene group. The term "oligomer" includes oligonucleotides and oligonucleotide analogs. The term "oligonucleotide" refers to a plurality of nucleoside monomers joined together in a specific sequence from naturally and non-naturally occurring heterocyclic base moieties. As used herein, the term "oligonucleotide analog" means compounds that can contain both naturally-occurring (i.e., "natural") and non-naturally-occurring (i.e.,"synthetic") moieties, such as nucleosidic subunits containing modified sugar and/or nucleobase portions. Such oligonucleotide analogs are typically structurally distinguishable from, yet functionally interchangeable with, naturally-occurring or synthetic wild-type oligonucleotides. Thus, oligonucleotide analogs include all such structures which function effectively to mimic the structure and/or function of a desired RNA or DNA strand, for example, by hybridizing to a target.

In the context of the present invention, the term "synthetic nucleoside" refers to a modified nucleoside. Representative modifications include modification of a heterocyclic base portion of a nucleoside to give a non-naturally-occurring nucleobase, a sugar portion of a nucleoside, or both simultaneously.

In the context of this invention, "heterocyclyl" or "heterocyclic ring system" is a cyclic compound containing at least one heteroatom such as N, O, or S. A "mixed heterocycle" is a cyclic compound containing at least two heteroatoms such as N, O, or S. A "heteroaryl" compound is a heterocycle containing at least one heteroatom such as N, O or S and is not fully saturated, e.g., is in a state of partial or complete saturation. "Heteroaryl" is also meant to include fused systems including systems where one or more of the fused rings contain no heteroatoms.

Preferred heterocycles amenable to the present invention include, but are not limited to, imidazole, pyrrole, pyrazole, indole, 1H-indazole, α-carboline, carbazole, phenothiazine, phenoxazine, tetrazole, triazole, pyrrolidine, piperidine, piperazine and morpholine. A more preferred group of nitrogen heterocycles includes imidazole, pyrrole and carbazole.

Representative heterocyclic base moieties useful in the compounds and methods described herein include adenine, guanine, cytosine, uridine, and thymine, as well as other non-naturally-occurring and natural nucleobases such as xanthine, hypoxanthine, 2-aminoadenine, 6-methyl and other alkyl derivatives of adenine and guanine, 2-propyl and other alkyl derivatives of adenine and guanine, 5-halo uracil and cytosine, 6-azo uracil, cytosine and thymine, 5-uracil (pseudo uracil), 4-thiouracil, 8-halo, oxa, amino, thiol, thioalkyl, hydroxyl and other 8-substituted adenines and guanines, 7-methylguanine, and 5-methyl, 5-trifluoromethyl and other 5-substituted uracils and cytosines.

Preferred heterocyclic base moieties include adenine, $N^6$-benzoyladenine, cytosine, $N^4$-benzoylcytosine, 5-methylcytosine, $N^4$-benzoyl-5-methylcytosine, thymine, uracil, guanine, $N^2$-isobutyrylguanine and 2-aminoadenine.

Further naturally- and non-naturally-occurring heterocyclic base moieties include those disclosed in U.S. Pat. No. 3,687,808 (Merigan et al.), in chapter 15 by Sanghvi, in *Antisense Research and Application,* Ed. S. T. Crooke and B. Lebleu, CRC Press, 1993, in Englisch et al., *Angewandte Chemie,* International Edition, 1991, 30, 613–722 (see, especially pages 622 and 623, and in the Concise *Encyclopedia of Polymer Science* and *Engineering,* J. I. Kroschwitz Ed., John Wiley & Sons, 1990, pages 858–859, Cook, P. D., *Anti-Cancer Drug Design,* 1991, 6, 585–607, each of which is hereby incorporated by reference in its entirety. The term "heterocyclic base moiety" is further intended to include heterocyclic ring systems that can serve as nucleosidic bases including certain 'universal bases' that are not nucleosidic bases in the most classical sense but serve as nucleosidic bases. Especially mentioned as a universal base is 3-nitropyrrole.

As used herein, the term "phosphorus protecting group" refers to a group that is initially bound to the phosphorus atom of a phosphoramidite. The phosphorus protecting group functions to protect the phosphorus containing internucleotide linkage or linkages during, for example, solid phase oligo-nucleotide synthetic regimes. Treatment of the internucleotide linkage or linkages that have a phosphorus protecting group thereon with a deprotecting agent, such as aqueous ammonium hydroxide, will result in the removal of the phosphorus protecting group and leave a hydroxyl or thiol group in its place.

There are many phosphorus protecting groups known in the art which are useful in the present invention including, but not limited, to β-cyanoethyl, diphenylsilylethyl, δ-cyanobutenyl, cyano p-xylyl (CPX), methyl-N-trifluoroacetyl ethyl (META) and acetoxy phenoxy ethyl (APOE) groups. Phosphorus protecting groups are further described in Beaucage, S. L. and Iyer, R. P., *Tetrahedron,* 1993, 49, 1925–1963; Beaucage, S. L. and Iyer, R. P., *Tetrahedron,* 1993, 49, 10441–10488; and Beaucage, S. L. and Iyer, R. P., *Tetrahedron,* 1992, 48, 2223–2311. Representative United States patents that teach the preparation of phosphorus protecting groups and their incorporation into phosphoramidite compounds include, but are not limited to, U.S. Pat. Nos. 5,783,690; 5,760,209; 5,705,621; 5,614,621; 5,453,496; 5,153,319; 5,132,418; 4,973,679; 4,725,677; 4,668,777; 4,500,707; 4,458,066; 4,415,732; and Re. 34,069, the entire contents of each of which are herein incorporated by reference.

Functional groups including those located on heterocyclic base moieties and 2'-sugar substituent groups are routinely blocked with protecting (blocking groups) during synthesis and subsequently deblocked. In general, a blocking group renders a chemical functionality of a molecule inert to specific reaction conditions and can later be removed from such functionality in a molecule without substantially damaging the remainder of the molecule. See, Green and Wuts, Protective Groups in Organic Synthesis, 2d edition, John Wiley & Sons, New York, 1991. For example, amino groups can be blocked with nitrogen protecting groups such as phthalimido, 9-fluorenyl-methoxycarbonyl (FMOC), triphenylmethylsulfenyl, t-BOC or benzyl groups. Carboxyl groups can be protected as acetyl groups. Representative hydroxyl protecting groups are described by Beaucage et al., *Tetrahedron* 1992, 48, 2223. Preferred hydroxyl protecting groups are acid-labile groups, such as the trityl, monomethoxytrityl, dimethoxytrityl, trimethoxytrityl, 9-phenylxanthin-9-yl (Pixyl) and 9-(p-methoxyphenyl) xanthin-9-yl (MOX). Chemical functional groups can also be "blocked" by including them in a precursor form. Thus an azido group can be considered a "blocked" form of an amine as the azido group is easily converted to the amine. Further representative protecting groups utilized in oligonucleotide synthesis are discussed in Agrawal et al., Protocols for Oligonucleotide Conjugates, Eds., Humana Press, New Jersey, 1994, Vol. 26, pp. 1–72.

As used herein, the term "oligonucleoside" includes oligomers or polymers containing two or more nucleoside subunits having a non-phosphorous linking moiety. Oligonucleosides according to the invention have a ribofuranose moiety attached to a nucleobase through a glycosyl bond. An oligonucleotide/nucleoside for the purposes of the present invention is a mixed backbone oligomer having at least two nucleosides covalently bound by a non-phosphate linkage and at least one phosphorous containing covalent bond with a nucleotide, wherein at least one of the monomeric nucleotide or nucleoside units is a 2'-O-substituted compound prepared using the process of the present invention. An oligonucleotide/nucleoside can additionally have a plurality of nucleotides and nucleosides coupled through phosphorous containing and/or non-phosphorous containing linkages.

As used herein, the term "sugar substituent group" or "2'-substituent group" includes groups attached to the 2'-position of the ribofuranosyl moiety with or without an oxygen atom. Sugar substituent groups amenable to the present invention include, but are not limited to, fluoro, O-alkyl, O-alkylamino, O-alkylalkoxy, protected O-alkylamino, O-alkylaminoalkyl, O-alkyl imidazole and polyethers of the formula $(O-alkyl)_m$, wherein m is 1 to about 10. Preferred among these polyethers are linear and cyclic polyethylene glycols (PEGs), and (PEG)-containing groups, such as crown ethers and those which are disclosed by Ouchi et al., *Drug Design and Discovery* 1992, 9, 93;

Ravasio et al., *J. Org. Chem.* 1991, 56, 4329; and Delgardo et. al., *Critical Reviews in Therapeutic Drug Carrier Systems* 1992, 9, 249, each of which is hereby incorporated by reference in its entirety. Further sugar modifications are disclosed in Cook, P. D., *Anti-Cancer Drug Design,* 1991, 6, 585–607. Fluoro, O-alkyl, O-alkylamino, O-alkyl imidazole, O-alkylaminoalkyl, and alkyl amino substitution is described in U.S. patent application Ser. No. 08/398,901, filed Mar. 6, 1995, entitled "Oligomeric Compounds having Pyrimidine Nucleotide(s) with 2' and 5' Substitutions," hereby incorporated by reference in its entirety.

Additional sugar substituent groups amenable to the present invention include 2'-SR and 2'-$NR_2$ groups, wherein each R is, independently, hydrogen, a protecting group or substituted or unsubstituted alkyl, alkenyl, or alkynyl. 2'-SR nucleosides are disclosed in U.S. Pat. No. 5,670,633, issued Sep. 23, 1997, hereby incorporated by reference in its entirety. The incorporation of 2'-SR monomer synthons is disclosed by Hamm et al., *J. Org. Chem.,* 1997, 62, 3415–3420. 2'-NR nucleosides are disclosed by Goettingen, M., *J. Org. Chem.,* 1996, 61, 6273–6281; and Polushin et al., *Tetrahedron Lett.,* 1996, 37, 3227–3230. Further representative sugar substituent groups amenable to the present invention include those having one of formula XI or XII:

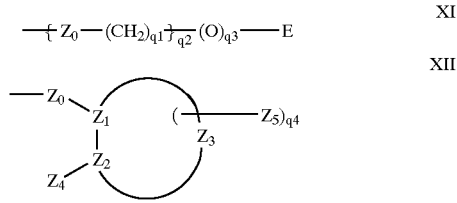

wherein:

$Z_0$ is O, S or NH;

E is $C_1-C_{10}$ alkyl, $N(Q_3)(Q_4)$ or $N=C(Q_3)(Q_4)$;

each $Q_3$ and $Q_4$ is, independently, H, $C_1-C_{10}$ alkyl, dialkylaminoalkyl, a nitrogen protecting group, a tethered or untethered conjugate group, a linker to a solid support;

or $Q_3$ and $Q_4$ together, form a nitrogen protecting group or a ring structure optionally including at least one additional heteroatom selected from N and O;

$q^1$ is an integer from 1 to 10;

$q^2$ is an integer from 1 to 10;

$q^3$ is 0 or 1;

$q^4$ is 0, 1 or 2;

each $Z_1$, $Z_2$ and $Z_3$ is, independently, $C_4-C_7$ cycloalkyl, $C_5-C_{14}$ aryl or $C_3-C_{15}$ heterocyclyl, wherein the heteroatom in said heterocyclyl group is selected from oxygen, nitrogen and sulfur;

$Z_4$ is $OM_1$, $SM_1$, or $N(M_1)_2$;

each $M_1$ is, independently, H, $C_1-C_8$ alkyl, $C_1-C_8$ haloalkyl, $C(=NH)N(H)M_2$, $C(=O)N(H)M_2$ or $OC(=O)N(H)M_2$;

$M_2$ is H or $C_1-C_8$ alkyl; and $Z_5$ is $C_1-C_{10}$ alkyl, $C_1-C_{10}$ haloalkyl, $C_2-C_{10}$ alkenyl, $C_2-C_{10}$ alkynyl, $C_6-C_{14}$ aryl, $N(Q_3)(Q_4)$, $OQ_3$, halo, $SQ_3$ or CN.

Representative 2'-O-sugar substituent groups of formula XI are disclosed in U.S. Pat. No. 6,172,209,, issued Jan. 9, 2001, entitled "Aminooxy-modified Oligonucleotides and Methods for Making Same".

Representative cyclic 2'-O-sugar substituent groups of formula XII are disclosed in U.S. patent application Ser. No. 09/123,108, filed Jul. 27, 1998, entitled "RNA Targeted 2'-Modified Oligonucleotides that are Conformationally Preorganized," hereby incorporated by reference in its entirety.

Sugars having O-substitutions on the ribosyl ring are also amenable to the present invention. Representative substitutions for ring O include, but are not limited to, S, $CH_2$, CHF, and $CF_2$. See, e.g., Secrist et al., *Abstract* 21, *Program & Abstracts, Tenth International Roundtable, Nucleosides, Nucleotides and their Biological Applications,* Park City, Utah, Sep. 16–20, 1992, hereby incorporated by reference in its entirety.

Additional modifications may also be made at other positions on the oligonucleotide, particularly the 3' position of the sugar on the 3' terminal nucleotide and the 5'-position of 5' terminal nucleotide. For example, one additional modification of the oligonucleotides of the present invention involves chemically linking to the oligonucleotide one or more moieties or conjugates which enhance the activity, cellular distribution or cellular uptake of the oligonucleotide. Such moieties include, but are not limited to, lipid moieties such as a cholesterol moiety (Letsinger et al., *Proc. Natl. Acad. Sci. USA,* 1989, 86, 6553), cholic acid (Manoharan et al., *Bioorg. Med. Chem. Lett.,* 1994, 4, 1053), a thioether, e.g., hexyl-S-tritylthiol (Manoharan et al., *Ann. N. Y. Acad. Sci.,* 1992, 660, 306; Manoharan et al., *Bioorg. Med. Chem. Let.,* 1993, 3, 2765), a thiocholesterol (Oberhauser et al., *Nucl. Acids Res.,* 1992, 20, 533), an aliphatic chain, e.g., dodecandiol or undecyl residues (Saison-Behmoaras et al., *EMBO J.,* 1991, 10, 111; Kabanov et al., *FEBS Lett.,* 1990, 259, 327; Svinarchuk et al., *Biochimie,* 1993, 75, 49), a phospholipid, e.g., di-hexadecyl-rac-glycerol or triethylammonium-1,2-di-O-hexadecyl-rac-glycero-3-H-phosphonate (Manoharan et al., *Tetrahedron Lett.,* 1995, 36, 3651; Shea et al., *Nucl. Acids Res.,* 1990, 18, 3777), a polyamine or a polyethylene glycol chain (Manoharan et al., *Nucleosides & Nucleotides,* 1995, 14, 969), adamantane acetic acid (Manoharan et al., *Tetrahedron Lett.,* 1995, 36, 3651), a palmityl moiety (Mishra et al., *Biochim. Biophys. Acta,* 1995, 1264, 229), or an octadecylamine or hexylamino-carbonyl-oxycholesterol moiety (Crooke et al., *J. Pharmacol. Exp. Ther.,* 1996, 277, 923).

As used herein, the term "phosphorus protecting group" refers to a group that is initially bound to the phosphorus atom of a phosphoramidite. The phosphorus protecting group functions to protect the phosphorus containing internucleotide linkage or linkages during, for example, solid phase oligonucleotide synthetic regimes. Treatment of the internucleotide linkage or linkages that have a phosphorus protecting group thereon with a deprotecting agent such as aqueous ammonium hydroxide will result in the removal of the phosphorus protecting group and leave a hydroxyl or thiol group in its place.

There are many phosphorus protecting groups known in the art which are useful in the present invention including, but not limited, to β-cyanoethyl, diphenylsilylethyl, δ-cyanobutenyl, cyano p-xylyl (CPX), methyl-N-trifluoroacetyl ethyl (META), acetoxy phenoxy ethyl (APE) and butene-4-yl groups. Phosphorus protecting groups are further described in: Beaucage, S. L. and Iyer, R. P., *Tetrahedron,* 1993, 49, 1925–1963; Beaucage, S. L. and Iyer, R. P., *Tetrahedron,* 1993, 49, 10441–10488; Beaucage, S. L. and Iyer, R. P., *Tetrahedron,* 1992, 48, 2223–2311. Representative U.S. patents that teach the preparation of phosphorus protecting groups and their incorporation into phosphoramidite compounds include, but are not limited to, U.S. Pat. Nos. 5,783,690; 5,760,209; 5,705,621; 5,614,621; 5,453,496; 5,153,319; 5,132,418; 4,973,679; 4,725,677; 4,668,777; 4,500,707; 4,458,066; 4,415,732; and Re. 34,069, the entire contents of each of which are herein incorporated by reference.

As used herein, the term "organic base moiety" includes, but is not limited to, N(Me)$_3$, N(Et)$_3$, N(n-Bu)$_3$, NEt(i-Pr)$_2$, N(alkyl)$_3$ or N(substituted alkyl)$_3$. According to the present invention, "leaving group" means a group susceptible to cleavage in a nucleophilic displacement reaction and includes, but is not limited to, chloro, bromo, iodo, mesylate, tosylate and triflate.

As used herein, the term "alkyl" includes, but is not limited to, straight chain, branched chain and alicyclic hydrocarbon groups. Alkyl groups of the present invention may be substituted. Representative alkyl substituents are disclosed in U.S. Pat. No. 5,212,295, at column 12, lines 41–50, hereby incorporated by reference in its entirety. Substituent groups include, but are not limited to, alkyl, alkenyl, alkynyl, aryl, hydroxyl, alkoxy, alcohol, benzyl, phenyl, nitro, thiol, thioalkoxy, thioalkyl, trifluoromethyl, halo, nitrile, trifluoromethoxy and azido. As used herein, the term "lower alkyl" is intended to mean an alkyl group having 6 or fewer carbons.

As used herein, the term "alkenyl" denotes a group having at least one double bond between two carbon atoms. The term "alkynyl" denotes a group having at least one triple bond between two carbon atoms.

As used herein, the term "aralkyl" denotes alkyl groups which bear aryl groups, for example, benzyl groups. The term "alkaryl" denotes aryl groups which bear alkyl groups, for example, methylphenyl groups. As used herein, the term "aryl" denotes aromatic cyclic groups including, but not limited to, phenyl, naphthyl, anthracyl, phenanthryl and pyrenyl. Preferred aryl and aralkyl groups include, but are not limited to, phenyl, benzyl, xylyl, naphthyl, toluyl, pyrenyl, anthracyl, azulyl, phenethyl, cinnamyl, benzhydryl, and mesityl. Typical substituents for substitution include, but are not limited to, hydroxyl, alkoxy, alcohol, benzyl, phenyl, nitro, thiol, thioalkoxy, halogen, or alkyl, aryl, alkenyl, or alkynyl groups.

As used herein, the term "alkanoyl" has its accustomed meaning as a group of formula —C(=O)-alkyl. A preferred alkanoyl group is the acetyl group.

In general, the term "heteroatom" denotes an atom other than carbon, preferably, but not exclusively, N, O, or S. Accordingly, the term "heterocycloalkyl" denotes an alkyl ring system having one or more heteroatoms (i.e., non-carbon atoms). Preferred heterocycloalkyl groups include, for example, morpholino groups. As used herein, the term "heterocycloalkenyl" denotes a ring system having one or more double bonds and one or more heteroatoms. Preferred heterocycloalkenyl groups include, for example, pyrrolidino groups.

In some preferred embodiments of the present invention, a first nucleoside or oligomer is attached to a solid support using an optional linker. Solid supports are substrates which are capable of serving as the solid phase in solid phase synthetic methodologies, such as those described in U.S. Pat. Nos. 4,415,732; 4,458,066; 4,500,707; 4,668,777; 4,973,679; and 5,132,418 (Caruthers); and U.S. Pat. Nos. 4,725,677 and Re. 34,069 (Koster). Linkers are known in the art as short molecules which serve to connect a solid support to functional groups (e.g., hydroxyl groups) of initial synthon molecules in solid phase synthetic techniques. Suitable linkers are disclosed in, for example, *Oligonucleotides And Analogues A Practical Approach,* Eckstein, F. Ed., IRL Press, N.Y., 1991, Chapter 1, pages 1–23.

Solid supports according to the present invention include those generally known in the art to be suitable for use in solid phase methodologies, including, for example, controlled pore glass (CPG), oxalyl-controlled pore glass. See, e.g., Alul et al., *Nucleic Acids Research* 1991, 19, 1527, hereby incorporated by reference in its entirety. Solid supports further include TentaGel Support, which is an aminopolyethyleneglycol derivatized support (Wright et al., *Tetrahedron Letters* 1993, 34, 3373, hereby incorporated by reference in its entirety) and Poros, which is a copolymer of polystyrene/divinylbenzene.

Hydroxyl protecting groups according to the present invention include a wide variety of groups. Preferably, the protecting group is stable under basic conditions but can be removed under acidic conditions. In general, protecting groups render chemical functionalities inert to specific reaction conditions, and can be appended to and removed from such functionalities in a molecule without substantially damaging the remainder of the molecule. Representative hydroxyl protecting groups are disclosed by Beaucage et al., *Tetrahedron* 1992, 48, 2223–2311, and Greene and Wuts, *Protective Groups in Organic Synthesis*, Chapter 2, 2d ed, John Wiley & Sons, New York, 1991, each of which is hereby incorporated by reference in its entirety. Preferred hydroxyl protecting groups include, but are not limited to, trityl, monomethoxytrityl, dimethoxytrityl (DMT), 9-phenylxanthen-9-yl (Pixyl), 9-(p-methoxyphenyl) xanthen-9-yl (Mox), t-butyldiphenylsilyl (TBDPS) and t-butyldimethylsilyl (TBDMS). Hydroxyl protecting groups can be removed from oligomers of the invention by techniques well known in the art to form the free hydroxyl. For example, dimethoxytrityl protecting groups can be removed by protic acids such as formic acid, dichloroacetic acid, trichloroacetic acid, p-toluene sulphonic acid or with Lewis acids such as for example zinc bromide. See, e.g., Greene and Wuts, supra.

In some preferred embodiments of the present invention, amino groups are appended to alkyl or to other groups such as, for example, 2'-alkoxy groups. Such amino groups are also commonly present in naturally-occurring and non-naturally-occurring nucleobases. It is generally preferred that these amino groups be in protected form during the synthesis of oligomers of the invention. Representative amino protecting groups suitable for these purposes are discussed in Greene and Wuts, *Protective Groups in Organic Synthesis,* Chapter 7, 2d ed, John Wiley & Sons, New York, 1991. Generally, as used herein, the term "protected," when used in connection with a molecular moiety such as "nucleobase," indicates that the molecular moiety contains one or more functionalities protected by protecting groups.

"Conjugate groups" according to the present invention include intercalators, reporter molecules, polyamines, polyamides, poly ethers including polyethylene glycols and other moieties known in the art for enhancing the pharmacodynamic properties or the pharmacokinetic properties of compounds. Typical conjugate groups include, but are not-limited to, PEG groups, cholesterols, phospholipids, biotin, phenanthroline, phenazine, phenanthridine, anthraquinone, acridine, fluoresceins, rhodamines, coumarins, pyrene, retinol and dyes.

The oligomeric compounds of the present invention can be used in diagnostics, therapeutics and as research reagents and kits. The oligomeric compounds of the present invention can also be used in pharmaceutical compositions by including a suitable pharmaceutically acceptable diluent or carrier.

These compounds can further be used for treating organisms having a disease characterized by the undesired production of a protein. For this purpose, the organism is contacted with an oligonucleotide having a sequence that is capable of specifically hybridizing with a strand of nucleic acid encoding the undesirable protein.

The formulation of therapeutic compositions and their subsequent administration is believed to be within the skill of those in the art. In general, for therapeutics, a patient in need of such therapy is administered an oligomer in accordance with the invention, commonly in a pharmaceutically acceptable carrier, in doses ranging from 0.01 µg to 100 g per kg of body weight depending on the age of the patient and the severity of the disease state being treated. Further, the treatment may be a single dose or may be a regimen that may last for a period of time which will vary depending upon the nature of the particular disease, its severity and the overall condition of the patient, and may extend from once daily to once every 20 years. Following treatment, the patient is monitored for changes in his/her condition and for alleviation of the symptoms of the disease state. The dosage of the oligomer may either be increased in the event the patient does not respond significantly to current dosage levels, or the dose may be decreased if an alleviation of the symptoms of the disease state is observed, or if the disease state has been ablated.

In some cases it may be more effective to treat a patient with an oligomer of the invention in conjunction with other traditional therapeutic modalities. For example, a patient being treated for AIDS may be administered an oligomer in conjunction with AZT, or a patient with atherosclerosis may be treated with an oligomer of the invention following angioplasty to prevent reocclusion of the treated arteries.

Dosing is dependent on severity and responsiveness of the disease condition to be treated, with the course of treatment lasting from several days to several months, or until a cure is effected or a diminution of disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligomers, and can generally be estimated based on $EC_{50}$s found to be effective in in vitro and in vivo animal models. In general, dosage is from 0.01 µg to 100 g per kg of body weight, and may be given once or more daily, weekly, monthly or yearly, or even once every 2 to several years.

Following successful treatment, it may be desirable to have the patient undergo maintenance therapy to prevent the recurrence of the disease state, wherein the oligomer is administered in maintenance doses, ranging from 0.01 µg to 100 g per kg of body weight, once or more daily, to once every several years.

The pharmaceutical compositions of the present invention may be administered in a number of ways depending upon whether local or systemic treatment is desired and upon the area to be treated. Administration may be topical (including ophthalmic, vaginal, rectal, intranasal, transdermal), oral or parenteral. Parenteral administration includes intravenous drip, subcutaneous, intraperitoneal or intramuscular injection, or intrathecal or intraventricular administration.

Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Compositions for oral administration include powders or granules, suspensions or solutions in water or non-aqueous media, capsules, sachets or tablets. Thickeners, flavoring agents, diluents, emulsifiers, dispersing aids or binders may be desirable.

Compositions for intrathecal or intraventricular administration may include sterile aqueous solutions which may also contain buffers, diluents and other suitable additives.

Formulations for parenteral administration may include sterile aqueous solutions which may also contain buffers, diluents and other suitable additives.

Treatments of this type can be practiced on a variety of organisms, ranging from unicellular prokaryotic and eukaryotic organisms to multicellular eukaryotic organisms. Any organism that utilizes DNA-RNA transcription or RNA-protein translation as a fundamental part of its hereditary, metabolic or cellular control is susceptible to therapeutic and/or prophylactic treatment in accordance with the present invention. Seemingly diverse organisms such as bacteria, yeast, protozoa, algae, all plants and all higher animal forms, including warm-blooded animals, can be treated. Further, each cell of multicellular eukaryotes can be treated, as they include both DNA-RNA transcription and RNA-protein translation as integral parts of their cellular activity. Furthermore, many of the organelles (e.g., mitochondria and chloroplasts) of eukaryotic cells also include transcription and translation mechanisms. Thus, single cells, cellular populations or organelles can also be included within the definition of organisms that can be treated with therapeutic or diagnostic oligonucleotides.

Those skilled in the art will appreciate that numerous changes and modifications may be made to the preferred embodiments of the invention and that such changes and modifications may be made without departing from the spirit of the invention. It is, therefore, intended that the appended claims cover all such equivalent variations as fall within the true spirit and scope of the invention.

EXAMPLES

Solvents used for the preparation of the condensing reagent or solid phase oligonucleotide synthesis were purchased from Aldrich or J. T. Baker in the highest grade available. Phosphorus oxychloride, 2,2 dimethyl-1,3-propanediol, 3'-O-acetylthymidine and N,O-bis (trimethylsilyl) acetamide (BSA) were purchased from Sigma-Aldrich. Pivaloyl chloride (Piv-Cl), bis(2-oxo-3-oxazolidinyl)phosphinic chloride (BOP-Cl), 4-dimethylaminopyridine (DMAP), 4-methoxypyridine-N-oxide (PyrO) and triethylamine were obtained from Fluka. Pivaloyl chloride was freshly distilled prior to its use for solid phase synthesis. Bromo-tris-pyrrolidino-phosphonium hexafluoro-phosphate (PyBroP) was purchased from Novabiochem. 3'-Methylene-H-phosphonate mononucleotides and (1S)-(+)-(camphorylsulfonyl)oxaziridine (CSO) were prepared at Isis Pharmaceuticals. 2-Chloro-5,5-dimethyl-2-oxo-1,3,2-dioxaphosphinane (NEP-Cl) was prepared according to a previously published procedure (McConnell and Coover, J. Org. Chem. 1958, 24, 630–635). Unmodified H-phosphonate mononucleotides and CPG supports loaded with standard 5'-DMT-2'-deoxynucleoside-3'-succinates were purchased from Glen Research and Perseptive Biosystems, respectively.

Compounds 1, 9, 13, and 17 were synthesized using a literature procedure. Sanghvi et al., *Synthesis,* 1994, 1163. Compound 1 may also be synthesized according to other literature procedures. Derry et al., *Anti-cancer Drug Design,* 1993, 8, 203; Mihkailov et al., *Nucleosides Nucleotides,*

1996, 15, 1323. Compounds 9 and 13 may also be synthesized according to the procedure described by Lebreton et al., *Tet. Lett.,* 1994, 35, 5225. Compound 2 may be synthesized as reported by Bhat et al. (*J. Org. Chem.,* 1996, 61, 8186).

New compounds 3 and 4 were prepared using procedures described for the preparation of compound 1. 3'-t-Butylphenoxythiocarbonyl compounds 5–8 were synthesized by reaction of the corresponding alcohols 1–4 with 3'-t-butylphenoxy chlorothionoformate following the procedure for the preparation of the 3'-phenoxythiocarbonyl-2'-deoxy derivative (*Synthesis,* 1994, 1163). Ammonium phosphinate was prepared based on a reported procedure (Montchamp et al., *J. Org. Chem.,* 1995, 60, 6076);

Example 1
Synthesis of Compound 11

To a solution of compound 7 (13.0 g, 18.8 mmol) in 150 mL of benzene was added PhCH=CHSnBu$_3$ (17.5 g, 47 mmol, 2.5 eq). The resulting solution was degassed three times with argon at room temperature and at 45° C. After AIBN (1.0 g, 6.1 mmol) was added, the resulting solution was refluxed for 2 h. Another part of AIBN (1.0 g, 6.1 mmol) was added after cooling to about 40° C. and refluxed for 2 h. This procedure was repeated until the starting material disappeared. The solvent was evaporated and the residue was purified by flash chromatography on a silica gel column using 10:1 and 5:1 hexanes-EtOAc as eluents to give 6.31 g (57%) of compound 11 as a white foam. $^1$H NMR (CDCl$_3$) d 1.29 (s, 9H), 1.43 (s, 3H), 3.19–3.50 (m, 1H), 3.81 (d, 0.5 H, J=2.6 Hz), 3.87 (d, 0.5 H, J=2.6 Hz), 4.22–4.30 (m, 2 H), 5.00 (d, 0.5 H, J=4.0 Hz), 5.26 (d, 0.5 H, J=4.0 Hz), 6.06 (d, 1 H, J=18.6 Hz), 6.08–6.20 (m, 1H), 6.67 (d, 1H, J=17.8 Hz), 7.24–7.68 (m, 16 H), 8.12 (s, 1H, ex D$_2$O); $^{13}$C NMR (CDCl$_3$) d 12.1, 19.6, 27.3, 31.3, 45.4, 45.8, 61.9, 84.0, 89.8, 90.6, 96.5, 100.2, 111.0, 120.0, 120.1, 125.6, 127.7, 128.1, 129.8, 130.2, 132.7, 133.2, 135.4, 135.5, 136.2, 136.4, 150.6; HRMS (FAB) m/z 585.2602 (M+H)$^+$ (C$_{34}$H$_{38}$N$_2$O$_4$SiF requires 585.2585).

Example 2
Synthesis of Compound 12

Compound 12 was prepared by the procedure described in Example 1, from compound 8 (15 g, 20 mmol), AIBN and PhCH=CHSnBu$_3$ (18.7 g, 50 mmol, 2.5 eq). The compound was purified by flash chromatography on a silica gel column using 10:1 and 5:1 hexanes-EtOAc as eluents to give 1.74 g (14%) of compound 12 as a white foam. $^1$H NMR (CDCl$_3$) d 1.13, (s, 9H), 1.43 (s, 3H), 3.18–3.30 (m, 1H), 3.37 (s, 3H), 3.58–3.62 (m, 2H), 3.79–3.80 (m, 2H), 4.06–4.37 (m, 4H), 4.95 (s, 1H), 6.25–6.40 (m, 1H), 6.62 (d, 1H, J=16 Hz), 7.27–7.71 (m, 16 H), 9.21 (s, 1H, ex D$_2$O); $^{13}$C NMR (CDCl$_3$) d 11.9, 19.6, 27.2, 45.3, 59.0, 62.1, 70.2, 72.0, 84.6, 87.1, 90.2, 110.4, 122.8, 126.4, 127.8, 128.0, 128.3, 128.6, 130.0, 132.7, 133.5, 134.7, 135.3, 135.4, 136.9, 150.3, 154.1; HRMS (FAB) m/z 641.3029 (M+H)$^+$ (C$_{37}$H$_{45}$N$_2$O$_6$Si requires 641.3047).

Example 3
Synthesis of Compound 10

Compound 10 was synthesized by the procedure described in Example 1, from compound 6.

Example 4
Synthesis of Compound 18

To a solution of 5'-O-TBDPS-2'-O-methyl-3'-styryl-1'-thymine (10, 30.0 g, 50.0 mmol) and N-methyl morpholine N-oxide (NMMO)(8.83 g, 75.0 mmol, 1.5 eq) in 900 mL of dioxane was added a catalytic amount of osmium tetraoxide (4% aqueous solution, 12.75 mL, 0.51 g, 2.0 mmol, 0.04 eq). The flask was covered by aluminum foil and the reaction mixture was stirred at room temperature overnight. A solution of NaIO$_4$ (32.1 g, 150.0 mmol, 3.0 eq), in 30 mL of water, was added to the above stirred reaction mixture. The resulting reaction mixture was stirred for 1 h at 0° C. and 2 h at room temperature, followed by addition of 60 mL of ethyl acetate. The mixture was filtered through a celite pad and washed with ethyl acetate. The filtrate was washed 3 times with 10% aqueous Na$_2$S$_2$O$_3$ solution until the color of aqueous phase disappeared. The organic phase was further washed with water and brine, dried (Na$_2$SO$_4$) and concentrated. Thus obtained aldehyde 14 was dissolved in 800 mL of ethanol-water (4:1, v/v). Sodium borohydride (NaBH$_4$) (9.5 g, 0.25 mol, 5.0 eq) was added in portions at 0° C. The resulting reaction mixture was stirred at room temperature for 2 h and then treated with 1000 g of ice water. The mixture was extracted with ethyl acetate. The organic phase was washed with water and brine, dried (Na$_2$SO$_4$) and concentrated. The resulting residue was purified by flash chromatography on a silica gel column using 50:1 to 20:1 CH$_2$Cl$_2$-MeOH as gradient eluents to give 17.8 g (68% from 10 for 3 steps) of alcohol product 18 as a white foam: silica gel TLC R$_f$ 0.40 (15:1 CH$_2$Cl$_2$-MeOH); $^1$H NMR (CDCl$_3$) d 1.11 (s, 9H), 1.50 (s, 3H), 2.45–2.60 (m, 1H), 2.62–2.72 (m, 1H), 3.60 (s, 3H), 3.65–3.95 (m, 3H, 1 OH), 4.00–4.40 (m, 3H), 5.94 (s, 1H), 7.30–7.50 (m, 6H), 7.52 (s, 1H), 7.60–7.74 (m, 4H), 9.75 (s, 1H); $^{13}$C NMR (CDCl$_3$) d 12.1, 19.5, 21.1, 42.9, 59.6, 63.2, 81.7, 87.7, 88.5, 110.8, 127.9, 130.1, 130.2, 132.5, 133.2, 135.1, 135.3, 135.5, 150.5, 161.4; HRMS (FAB) m/z 657.137 (M+Cs)$^+$ (C$_{28}$H$_{36}$N$_2$SiO$_6$Cs requires 657.139). Anal. Calcd for C$_{28}$H$_{36}$N$_2$SiO$_6$·½H$_2$O: C, 63.05; H, 6.99; N, 5.25. Found: C, 63.07; H, 7.16; N, 5.11.

Example 5
Synthesis of Compound 19

Compound 19 was prepared by the procedure described in Example 4 for compound 18, from 5'-O-TBDPS-2'-fluoro-3'-styryl-1'-thymine (11)(4.12 g, 7.05 mmol). The compound was purified by flash chromatography on a silica gel column using 200:1 and 50:1 CH$_2$Cl$_2$-MeOH as eluents to give 1.77 g (49%) of compound 19 as a white foam. $^1$H NMR (CDCl$_3$) d 1.09 (s, 9H), 1.57 (s, 3H), 2.56–2.88 (m, 1H), 2.92 (br, 1H, ex D$_2$O), 3.62–3.71 (m, 1H), 3.78–3.86 (m, 2H), 4.12–4.18 (m, 2H), 5.19 (d, 0.5H, J=4.5 Hz), 5.45 (d, 0.5H, J=4.5 Hz), 5.97 (d, 1H, J=18.0 Hz), 7.36–7.69 (m, 11H), 9.80 (br, 1H, ex D$_2$O); $^{13}$C NMR (CDCl$_3$) d 12.2, 19.1, 27.1, 44.2, 44.6, 57.4, 57.6, 63.4, 82.5, 89.6, 90.3, 95.1, 98.7, 110.18, 127.7, 128.0, 130.1, 132.5, 133.0, 135.4, 135.6, 150.4, 164.2; $^{19}$F NMR (CDCl3) d −63.77 (sep, J$_1$=19.8 Hz, J$_2$=35.5 Hz, J$_3$=55.2 Hz); HRMS (FAB) m/z 535.2018 (M+Na)$^+$ (C$_{27}$H$_{33}$N$_2$O$_5$FSiNa requires 535.2040).

Example 6
Synthesis of Compound 20

Compound 20 was prepared by the procedure described in Example 4 for compound 18, from 5'-O-TBDPS-2'-OCH$_2$CH$_2$OCH$_{3-3}$'-styryl-1'-thymine (12)(5.0 g, 7.8 mmol). The compound was purified by flash chromatography on a silica gel column using 2:1, 1:1 and 1:2 hexanes-EtOAc as eluents to give 1.6 g (36%) of compound 20 as a white foam. $^1$H NMR (CDCl$_3$) d 1.09 (s, 9H), 1.50 (s, 3H), 2.25 (br, 1H, ex D$_2$O), 2.52–2.78 (m, 1H), 3.38 (s, 3H), 3.52–4.25 (m, 10 H), 5.86 (s, 1H), 7.38–7.70 (m, 11H), 9.95 (br, 1H, ex D$_2$O); $^{13}$C NMR (CDCl$_3$) d 12.1, 19.5, 27.1, 43.1, 58.2, 58.8, 63.1, 69.5, 71.6, 82.3, 86.1, 89.8, 110.5, 128.0, 130.2, 132.5, 133.2, 135.1, 135.3, 136.5, 150.5, 164.4; HRMS (FAB) m/z 569.2688 (M+H)$^+$ (C$_{30}$H$_{41}$N$_2$O$_7$Si requires 569.2683).

Example 7
Synthesis of Compound 22

To a solution of compound 18 (23.3 g, 44.2 mmol) in 400 mL of anhydrous DMF under stirring was added sequentially at 0° C. 2,6-lutidine (10 mL, 9.2 g, 8.85 mmol, 1.95 eq) and methyl triphenoxyphosphonium iodide (24.3 g, 53.7 mmol, 1.2 eq). The resulting reaction mixture was stirred at 0° C. for 1 h and at room temperature for 2 h. The reaction mixture was diluted with 100 mL of ethyl acetate and washed twice with 0.1 N Na$_2$S$_2$O$_3$ aqueous solution to remove iodine. The organic phase was further washed with dilute NaHCO$_3$ solution, water, and brine. The aqueous phases were back extracted with ethyl acetate. The combined organic phase was dried (Na$_2$SO$_4$) and concentrated. The resulting residue was purified by flash chromatography on a silica gel column using 200:1 to 30:1 CH$_2$Cl$_2$-MeOH as gradient eluents to give 22.8 g (81%) of the iodo product 22 as a white foam: silica gel TLC R$_f$ 0.54 (20:1 CH$_2$Cl$_2$-MeOH), R$_f$ 0.63 (1:1 hexanes-EtOAc); $^1$H NMR (CDCl$_3$) d 1.13 (s, 9H), 1.61 (s, 3H), 2.60–2.84 (m, 2H), 3.18 (t, 3H, J=9.0 Hz), 3.64 (s, 3H), 3.67–3.80 (m, 1H), 3.84–3.98 (m, 2H), 4.05–4.21 (m, 1H), 5.91 (s, 1H), 7.32–7.49 (m, 6H), 7.54–7.74 (m, 5H), 8.90 (s, 1H); $^{13}$C NMR (CDCl$_3$) d 12.3, 19.4, 27.2, 44.9, 59.0, 62.5, 83.2, 86.8, 88.3, 110.6, 127.7, 128.0, 128.2, 130.2, 130.3, 132.4, 132.9, 134.9, 135.4, 135.6, 150.4, 164.3; HRMS (FAB) m/z 635.144 (M+H)$^+$ (C$_{28}$H$_{36}$N$_2$SiIO$_5$ requires 635.143). Anal. Calcd for C$_{28}$H$_{35}$N$_2$SiIO$_5$: C, 53.00; H, 5.55; N, 4.41. Found: C, 53.20; H, 5.53; N, 4.39.

Example 8
Synthesis of Compound 23

Compound 23 was prepared according to the procedure described above for compound 22, from compound 19 (1.3 g, 2.54 mmol), methyl triphenoxy phosphonium iodide (1.7 g, 3.8 mmol, 1.5 eq) and 2,6-lutidine (0.59 mL, 0.54 g, 5.08 mmol). The product was purified by flash chromatography on a silica gel column using 200:1 CH$_2$Cl$_2$-MeOH as an eluent to give 1.45 g (92%) of compound 23 as a white foam. $^1$H NMR (CDCl$_3$) d 1.11 (s, 9H), 1.63 (s, 3H), 2.76–3.18 (m, 3H), 3.73 (d, 0.5 H, J=2.8 Hz), 3.79 (d, 0.5 H, J=2.8 Hz), 3.95 (s, 0.5H), 3.99 (s, 0.5H), 4.14 (d, 0.5 H, J=2.0 Hz), 4.20 (d, 0.5 H, J=2.0 Hz), 5.08 (d, 0.5 H, J=3.8 Hz), 5.34 (d, 0.5 H, J=3.8 Hz), 5.98 (d, 1H, J=19.4 Hz), 7.39–7.71 (m, 11H), 8.46 (br, 1H, ex D$_2$O); HRMS (FAB) m/z 645.1030 (M+Na)$^+$ (C$_{27}$H$_{32}$N$_2$O$_4$FSiNa requires 645.1058).

Example 9
Synthesis of Compound 24

The iodide compound 24 was synthesized according to the procedure described above for compound 22, from compound 20 (1.34 g, 2.35 mmol), 2,6-lutidine (547 mL, 503 mg, 4.69 mmol, 2.0 eq) and methyl triphenoxyphosphonium iodide (1.28 g, 2.83 mmol, 1.2 eq) in 25 mL of DMF. The crude product was purified by flash chromatography on a silica gel column. Gradient elution with 5:1, 3:1 and then 1:1 hexanes-EtOAc provided 1.24 g (78%) of compound 24 as a white foam: silica gel TLC R$_f$ 0.39 (1:1 hexanes–EtOAc); $^1$H NMR (CDCl$_3$) d 1.13 (s, 9H), 1.62 (s, 3H), 2.64–2.85 (m, 2H), 3.20–3.35 (m, 1H), 3.38 (s, 3H), 3.50–4.25 (m, 8H), 5.91 (s, 1H), 7.32–7.50 (m, 6H), 7.60 (s, 1H), 7.62–7.78 (m, 4H), 10.46 (s, 1H); $^{13}$C NMR (CDCl$_3$) d 12.4, 19.5, 27.2, 45.0, 58.0, 62.5, 70.3, 71.9, 83.3, 85.6, 88.9, 110.5, 128.1, 128.2, 130.1, 130.3, 132.4, 132.9, 135.0, 135.4, 135.6, 150.7, 164.7; HRMS (FAB) m/z 679.172 (M+H)$^+$ (C$_{30}$H$_{40}$N$_2$SiIO$_6$ requires 679.170).

Example 10
Synthesis of Compound 26

A mixture of ammonium phosphinate (0.41 g, 5.0 mmol. 1.0 eq) and 1,1,1,3,3,3-hexamethyldisilazane (1.07 mL, 0.82 g, 5.05 mmol, 5.05 eq) was heated at 100–110° C. for 2 h under nitrogen atmosphere with a condenser. The resulting intermediate bis(trimethylsilyl)phosphonite (TBSP)(25) was cooled to –5 to 0° C. Anhydrous dichloromethane (5 mL) was added, followed by a solution of iodo compound 22 (0.64 g, 1.0 mmol) in 8 mL of dichloromethane. The resulting reaction mixture was stirred at room temperature overnight, filtered and concentrated. The clear oily residue was dissolved in 5 mL of dichloromethane and 5 mL of methanol. The solution was stirred at room temperature for 2 h. After evaporation of the solvent, the residue was dissolved in ethyl acetate. The solution was washed with water and brine. The organic phase was dried and concentrated. The crude product was purified by flash chromatography on a silica gel column using 10:1, 2:1 and then 1:1 EtOAc-MeOH as eluents to provide 105 mg (31%) of the desired hydrogen phosphinic acid 26 and 150 mg (59%) of the reduced product 29 as white foams.

Compound 26: silica gel TLC R$_f$ 0.30 (50:10:1 CHCl$_3$–MeOH–NEt$_3$); $^1$H NMR (CD$_3$OD) d 1.10 (s, 9H), 1.33 (s, 3H), 1.30–1.51 (m, 1H), 1.74–1.98 (m, 1H), 2.47–2.68 (m, 1H), 3.53 (s, 3H), 3.87–4.08 (m, 3H), 4.19 (d, 1H, J=11.6 Hz), 5.82, 8.32 (d, 1H, J=500 Hz, P–H), 5.91 (s, 1H), 7.35–7.50 (m, 6H), 7.59 (s, 1H), 7.65–6.80 (m, 4H); $^{13}$C NMR (DMSO$_d$) d 11.7, 18.9, 26.8, 36.1, 48.6, 57.3, 63.1, 84.8, 88.3, 108.9, 128.0, 129.9, 132.5, 133.1, 134.9, 135.0, 150.1, 163.7; $^{31}$P NMR (CD$_3$OD) d 27.1; MS (ES) m/z 571 (M – H)$^-$; HRMS (FAB) m/z 595.200 (M+Na)$^+$ (C$_{28}$H$_{37}$N$_2$PSiO$_7$Na requires 595.200).

Reduced product 29: silica gel TLC R$_f$ 0.30 (2:1 hexanes–EtOAc); $^1$H NMR (CDCl$_3$) d 0.98 (d, 3H, J=6.8 Hz), 1.12 (s, 9H), 1.49 (s, 3H), 2.28–2.45 (m, 1H), 3.59 (s, 3H), 3.71–3.85 (m, 2H), 3.95 (d, 1H, J=10.2 Hz), 4.19 (d, 1H, J=11.6 Hz), 5.91 (s, 1H), 7.30–7.50 (m, 6H), 7.58–7.75 (m, 5H), 10.00 (s, 1H); $^{13}$C NMR (CDCl$_3$) d 8.7, 12.1, 19.6, 27.2, 35.3, 58.4, 62.6, 86.2, 87.5, 88.8, 110.3, 128.0, 130.1, 132.7, 133.3, 135.3, 135.6, 150.5, 164.5; HRMS (FAB) m/z 509.247 (M+H)$^+$ (C$_{28}$H$_{37}$N$_2$SiO$_5$ requires 509.247). Anal. Calcd for C$_{28}$H$_{36}$N$_2$SiO$_5$: C, 66.11; H, 7.12; N, 5.50. Found: C, 65.96; H, 7.38; N, 5.43.

Example 11
Synthesis of Compounds 27 and 30

Compounds 27 and 30 were prepared by the procedure described in Example 10 for compounds 26 and 29, from 1,1,1,3,3,3-hexamethyldisilazane (18.0 g, 50 mmol), ammonium phosphinate (1.0 g, 12 mmol) and compound 23 (0.75 g, 1.2 mmol). The product was purified by flash chromatography on a silica gel column using 20:1 and 5:1 CH$_2$Cl$_2$-MeOH as eluents to give 0.10 g (15%) of compound 27 as a white powder and 0.3 g (50%) of compound 30 as a white foam.

Compound 27: $^1$H NMR (CD$_3$OD) d 1.10 (s, 9H), 1.42 (s, 3H), 1.35–1.91 (m, 2H), 2.56–2.86 (m, 1H), 3.85–4.31(m, 3H), 5.25 (d, 0.5H, J=4.2 Hz), 5.51 (d, 0.5H, J=4.2 Hz), 5.88, 8.39 (d, 1H, J=502 Hz), 6.01 (d, 1H, J=20 Hz), 7.32–7.78 (m, 11H); $^{31}$P NMR (CD$_3$OD) d 25.01; $^{19}$F NMR (CD$_3$OD) d −62.62 (sep, J$_1$=20.1 Hz, J$_2$=34.1 Hz, J$_3$=54.8 Hz); HRMS (FAB) m/z 583.1801 (M+Na)$^+$ (C$_{27}$H$_{34}$N$_2$O$_6$FPSiNa requires 583.1806).

Compound 30: $^1$H NMR (CDCl$_3$) d 1.03 (d, 3H, J=6.8 Hz), 1.10 (s, 9H), 1.56 (s, 3H), 1.32–1.65 (m, 1H), 3.77 (d, 0.5 H, J=2.8 Hz), 3.83 (d, 0.5 H, J=2.8 Hz), 3.95–4.00 (m, 1 H), 4.18–4.24 (m, 1H), 4.90 (d, 0.5H, J=4.2 Hz), 5.16 (d, 0.5H, J=4.2 Hz), 5.99 (d, 1H, J=18.0 Hz), 7.37–7.71 (m, 11H), 9.83 (s, 1H, ex D$_2$O); $^{13}$C NMR (CDCl$_3$) d 7.9, 8.1, 12.1, 19.5, 27.1, 35.6, 37.0, 62.1, 85.7, 89.3, 90.1, 96.5, 100.1, 110.7, 12,8.0, 130.1, 132.6, 133.1, 135.2, 135.4, 136.6, 150.3, 164.3; $^{19}$F NMR (CDCl$_3$) d −62.77 (sep, J$_1$=19.5 Hz, J$_2$=35.5 Hz, J$_3$=55.5 Hz); MS (ES) m/z 519 (M+Na)$^+$ (C$_{27}$H$_{34}$N$_2$O$_6$FPNa requires 519).

Example 12
Synthesis of Compound 31 as the TBAF Salt

To a solution of 5'-TBDPS protected hydrogen phosphinic acid 26 (140 mg, 0.20 mmol) in 1 mL of DMF and 8 mL of THF was added tetrabutylammonium fluoride (TBAF, 1.0 M in THF, 0.31 mL, 0.31 mmol, 1.5 eq) at 0° C. The reaction mixture was stirred at room temperature for 4 h and concentrated. The residue was purified by flash chromatography on a silica gel column using 20:1, 2:1, and then 1:1 EtOAc-MeOH as eluents to give 108 mg (94%) of sticky oily product 31 as its t-butyl ammonium salt: silica gel TLC R$_f$ 0.39 (1:1 EtOAc-MeOH); $^1$H NMR (CD$_3$OD) d 1.02 (t, 12H, J=7.0 Hz), 1.30–1.55 (m, 8H), 1.57–1.78 (m, 8H), 1.85 (s, 3H), 1.80–2.00 (m, 1H), 2.34–2.65 (m, 1H), 3.18–3.45 (m, 9H), 3.55 (s, 3H), 3.70–4.06 (m, 4H), 5.81, 8.31 (d, 1H, J=500 Hz, P—H), 5.87 (s, 1H), 8.25 (s, 1H); $^{13}$C NMR (CD$_3$OD) d 12.6, 14.0, 20.7, 24.8, 27.2, 28.9, 36.1, 58.3, 59.5, 60.4, 87.3, 87.7, 88.0, 89.7, 110.2, 138.3, 152.1, 166.7; $^{31}$P NMR (CD$_3$OD) d 26.9. MS (ES) m/z 333 (M−H)$^-$.

Example 13
Synthesis of Compound 31 (Salt Free)

A mixture of 26 (500 mg, 0.87 mmol) and triethylamine trifluoride (1.15 mL, 1.14 g, 7.07 mmol, 8.1 eq) in 10 mL of DMF and 15 mL of THF was stirred at room temperature for 48 h. The solvent was evaporated and the residue was purified by flash chromatography on a silica gel column using 10:1, 2:1 and then 1:1 EtOAc-MeOH as eluents to give 370 mg (97%) of product 31 as its white foam: silica gel TLC R$_f$ 0.39 (1:1 EtOAc-MeOH); $^1$H NMR (CD$_3$OD) d 1.30–1.80 (m, 2H), 1.86 (s, 3H), 2.24–2.55 (m, 1H), 3.55 (s, 3H), 3.74–4.06 (m, 4H), 5.81, 8.31 (d, 1H, J=500 Hz, P—H), 5.87 (s, 1H), 8.25 (s, 1H); $^{13}$C NMR (CD$_3$OD) d 12.6, 27.2, 28.9, 36.1, 58.3, 60.4, 87.3, 87.7, 88.0, 89.8, 110.2, 138.3, 152.1, 166.7; $^{31}$P NMR (CD$_3$OD) d 27.0; $^{13}$P NMR (CD$_3$OD+HCl) d 36.9; MS (ES) m/z 333 (M−H)$^-$; HRMS (FAB) m/z 357.083 (M+Na)$^+$ (C$_{12}$H$_{19}$N$_2$PO$_7$Na requires 357.082). Anal. Calcd for C$_{12}$H$_{19}$N$_2$PO$_7$: C, 43.12; H, 5.72; N, 8.38. Found: C, 43.37; H, 5.87; N, 8.25.

Example 14
Synthesis of Compound 32

Phosphinic acid 31 (70 mg, 0.2 mmol) was co-evaporated twice with anhydrous pyridine and then dissolved in 3 mL of pyridine. To this solution was added dimethyl trityl chloride (203 mg, 0.6 mmol, 3.0 eq) at 0° C. The reaction mixture was stirred at room temperature for 24 h and concentrated. The residue was purified by flash chromatography on a silica gel column. Elution with 100:10:1 to 100:30:1 CHCl$_3$-MeOH-TEA provided 95 mg (65%) of triethylamine salt product 32 as a white foam: silica gel TLC R$_f$ 0.39 (50:10:1 CHCl$_3$-MeOH-TEA); $^1$H NMR (CD$_3$OD) d 1.21 (t, 9H, J=7.2 Hz), 1.55–1.95 (m, 2H), 2.60–2.85 (m, 1H), 3.16 (q, 6H, J=7.2 Hz), 3.57 (s, 3H), 3.76 (s, 6H), 3.90–4.15 (m, 3H), 5.81 (s, 1H), 5.83, 8.31 (d, 1H, J=496 Hz, P—H), 6.84 (s, 2H), 6.89 (s, 2H), 7.20–7.53 (m, 9H), 7.91 (s, 1H); $^{13}$C NMR (CD$_3$OD) d 9.3, 12.3, 27.3, 29.1, 37.5, 47.7, 55.8, 58.2, 62.5, 86.1, 86.5, 86.7, 87.9, 90.4, 110.6, 114.3, 128.2, 129.0, 129.6, 131.5, 136.7, 136.8, 137.5, 145.9, 151.9, 160.3, 166.2; $^{31}$P NMR (CD$_3$OD) d 27.2. HRMS (FAB) m/z 659.212 (M+Na)$^+$ (C$_{33}$H$_{37}$N$_2$PO$_9$Na requires 659.213).

Example 15
Synthesis of Compound 35

Compound 35 was synthesized by the procedure described in Example 4 for compound 18, from 5'-DMT-2'-O-methyl-3'-C-styryl-1'-thymine (33, 8.0 g, 12.1 mmol), N-methylmorpholine N-oxide (2.13 g, 18.2 mmol, 1.5 eq), OsO$_4$ (4% aqueous solution, 3.07 mL, 122 mg, 0.48 mmol, 0.04 eq), NaIO$_4$ (7.77 g, 36.3 mmol, 3.0 eq), and NaBH$_4$ (1.84 g, 48.6 mmol, 4.0 eq). Chromatographic purification of the crude product using 50:1 to 10:1 CH$_2$Cl$_2$-MeOH as gradient eluents provided 5.48 g (77%) of product 35 as a white foam: silica gel TLC R$_f$ 0.39 (10:1 CH$_2$Cl$_2$-MeOH); $^1$H NMR (CDCl$_3$) d 1.37 (s, 3H), 2.41–2.51 (m, 1H), 2.53–2.70 (m, 1H), 3.23–3.42 (m, 2H), 3.62 (s, 3H), 3.60–3.90 (m, 2H), 3.78 (s, 6H), 4.06 (d, 1H, J=5.4 Hz), 4.40–4.51 (m, 1H), 5.92 (s, 1H), 6.81 (d, 2H, J=2.0 Hz), 6.86 (d, 2H, J=2.0 Hz), 7.20–7.48 (m, 9H), 7.81 (s, 1H), 8.70 (s, 1H); $^{13}$C NMR (CDCl$_3$) d 11.9, 42.9, 55.3, 58.5, 62.0, 80.9, 86.7, 87.9, 88.7, 110.6, 113.3, 127.2, 128.0, 128.2, 130.1, 135.4, 144.3, 150.5, 158.8, 164.4.

Example 16
Synthesis of Compound 36

Compound 36 was synthesized according to the procedure described in Example 7 for compound 22, from 35 (0.98 g, 1.66 mmol), 2,6-lutidine (390 mL, 358 mg, 3.34 mmol, 2.0 eq) and methyl triphenoxyphosphonium iodide (905 mg, 2.0 mmol, 1.2 eq). Flash chromatographic purification using 80:1 and 20:1 CH$_2$Cl$_2$-MeOH as eluents gave 0.84 g (72.5%) of iodo compound 36 as a white foam: silica gel TLC R$_f$ 0.35 (30:1 CH$_2$Cl$_2$-MeOH); $^1$H NMR (CDCl$_3$) d 1.44 (s, 3H), 2.70–2.86 (m, 2H), 3.09–3.30 (m, 2H), 3.66 (s, 3H), 3.68–3.71 (m, 1H), 3.80 (s, 6H), 3.91 (d, 1H, J=4.4 Hz), 3.99 (d, 1H, J=9.8 Hz), 5.91 (s, 1H), 6.84 (s, 2H), 6.88 (s, 2H), 7.20–7.45 (m, 9H), 7.80 (s, 1H), 9.10 (s, 1H); $^{13}$C NMR (CDCl$_3$) d 12.2, 45.1, 55.3, 59.0, 61.5, 82.5, 86.8, 88.4, 110.6, 113.4, 127.3, 128.2, 130.2, 135.2, 135.3, 144.2, 150.6, 158.8, 164.6. HRMS (FAB) m/z 721.139 (M+Na)$^+$ (C$_{33}$H$_{35}$N$_2$IO$_7$Na requires 721.138). Anal. Calcd for C$_{33}$H$_{35}$N$_2$IO$_7$.H$_2$O: C, 55.31; H, 5.20; N, 3.91. Found: C, 55.44; H, 5.19; N, 3.87.

Example 17
Synthesis of Compound 38

A solution of compound 22 (6.35 g, 10.0 mmol) and triethylamine trifluoride (6.52 mL, 6.45 g, 40.0 mmol, 4.0 eq) in 100 mL of THF was stirred at room temperature for 24 h. The reaction mixture was diluted with 200 mL of ethyl acetate and washed with water and brine. The organic phase was dried (Na$_2$SO$_4$) and concentrated. The residue was purified by flash chromatography on a silica gel column. Elution with 3:1, 1:1 and then 1:2 hexanes-EtOAc provided 3.76 g (95%) of product 38 as a white foam: silica gel TLC R$_f$ 0.40 (1:2 hexanes-EtOAc); $^1$H NMR (CDCl$_3$) d 1.87 (s, 3H), 2.56–2.74 (m, 1H), 3.17–3.30 (m, 2H), 3.61 (s, 3H), 3.70–4.04 (m, 4H), 5.88 (s, 1H), 8.18 (s, 1H); $^{13}$C NMR (CDCl$_3$) d 12.6, 45.1, 59.2, 60.8, 85.2, 88.7, 89.1, 110.6, 138.0, 152.1, 166.6; HRMS (FAB) m/z 397.026 (M+H)$^+$ ($C_{12}H_{18}N_2O_5I$ requires 397.026). Anal. Calcd for $C_{12}H_{17}N_2IO_5$: C, 36.37; H, 4.32; N, 7.07. Found: C, 35.97; H, 4.17; N, 7.01.

Example 18
Synthesis of Compound 39

Compound 39 was prepared by the procedure described in Example 17 for compound 38, from compound 23 (0.62 g, 3.25 mmol) and triethylamine trifluoride (2.65 ml, 16.2 mmol, 5 eq). The product was purified by flash chromatography on a silica gel column using 20:1 $CH_2Cl_2$-MeOH as an eluent to give 1.15 g (92%) of compound 39 as a white foam. $^1H$ NMR ($CDCl_3$) d 1.90 (s, 3H), 2.60 (t, 1H, J=4.8 Hz, ex $D_2O$), 2.82–3.30 (m, 3H),3.82–4.16 (m, 3H), 5.13 (d, 0.5H, J=4.4 Hz), 5.39 (d, 0.5H, J=4.4 Hz), 5.88 (d, 1H, J=19.6 Hz), 7.59 (s, 1H), 9.08 (br, 1H, ex $D_2O$), $^{19}F$ NMR ($CDCl_3$) d −63.23 (sep, $J_1$=20.2 Hz, $J_2$=35.2 Hz, $J_3$=55.4 Hz); HRMS (FAB) m/z 385.0064 (M+H)$^+$ ($C_{11}H_{15}N_2O_4FI$ requires 385.0061).

Example 19
Synthesis of Compound 41

The deprotected iodo compound 41 was synthesized as described in Example 17, from compound 24 (1.12 g, 1.65 mmol) and triethylamine trifluoride (1.1 mL, 1.08 g, 6.7 mmol, 4.0 eq) in 20 mL of THF. The crude product was purified by flash chromatography on a silica gel column. Gradient elution with 2:1, 1:2 and then 1:3 hexanes-EtOAc provided 504 mg (69%) of the deprotected iodo product 41 as a white foam; silica gel TLC $R_f$ 0.27 (1:3 hexanes-EtOAc); $^1H$ NMR ($CD_3OD$) d 1.87 (s, 3H), 2.47–2.75 (m, 1H), 3.18–3.37 (m, 2H), 3.40 (s, 3H), 3.59–3.70 (m, 2H), 3.71–3.90 (m, 2H), 3.92–4.17 (m, 4H), 5.87 (s, 1H), 8.17 (s, 1H); $^{13}C$ NMR ($CD_3OD$) d 12.5, 45.2, 59.2, 60.9, 71.0, 72.9, 85.4, 87.3, 89.7, 110.5, 138.0, 152.1, 166.6; HRMS (FAB) m/z 441.053 (M+H)$^+$ ($C_{14}H_{22}N_2IO_6$ requires 441.052).

Example 20
Synthesis of Compound 36 (from 38)

A mixture of compound 38 (3.17 g, 8.0 mmol), diisopropylethylamine (4.2 mL, 3.11 g, 24 mmol, 3.0 eq), and 4',4'-dimethoxytrityl chloride (5.42 g, 16.0 mmol, 2.0 eq) in 80 mL of ethyl acetate was stirred at 0° C. to room temperature for 7 h. The resulting reaction mixture was diluted with ethyl acetate, and washed with water and then brine. The organic phase was dried ($Na_2SO_4$) and concentrated. The residue was purified by flash chromatography on a silica gel column using 3:1 to 1:1 hexanes-EtOAc as gradient eluents to give 5.53 g (99%) of product 36 as a white foam. Compound 36 obtained by this method shows identical chromatographic and spectroscopic properties as the compound synthesized from compound 35.

Example 21
Synthesis of Compound 37

Compound 37 was prepared by the procedure described in Example 20 for compound 36, from compound 39 (1.15 g, 3 mmol), diisopropylethylamine (1.16 g, 9 mmol, 3 eq) and 4',4'-dimethoxytrityl chloride (2.03 g, 6 mmol, 2 eq). The product was purified by flash chromatography on a silica gel column using 10:1, 5:1 and 2:1 hexanes-EtOAc as eluents to give 1.82 g (88%) of compound 37 as a white foam. $^1H$ NMR ($CDCl_3$) d 1.53 (s, 3H), 2.73–2.95 (m, 1H), 2.94–3.18 (m, 2H), 3.26–3.43 (m, 1H), 3.67–3.80 (m, 1H), 3.80 (s, 6H), 3.98–4.13 (m, 1H), 5.13 (d, 0.5H, J=4.4 Hz), 5.39 (d, 0.5H, J=4.4 Hz), 6.01 (d, 1H, J=18 Hz), 6.85–7.44 (m, 13H), 7.69 (s, 1H), 9.67(br, 1H, ex $D_2O$); $^{13}C$ NMR ($CDCl_3$) d 12.2, 45.4, 45.8, 55.3, 61.3, 82.3, 87.0, 88.9, 89.6, 95.6, 99.3, 111.1, 113.4, 127.3, 128.1, 130.1, 135.1, 135.2, 144.1, 150.2, 158.8, 164.2; HRMS (FAB) m/z 687.1351 (M+H)$^+$ ($C_{32}H_{33}N_2O_6FI$ requires 687.1367).

Example 22
Synthesis of Compound 31 (from 36) and Compound 42

A mixture of ammonium phosphinate (1.66 g, 20 mmol, 10 eq) and 1,1,1,3,3,3-hexamethyldisilazane (4.64 mL, 3.55 g, 22.0 mmol, 11.0 eq) was heated at 100–110° C. for 2 h under nitrogen atmosphere with condenser. The crude intermediate compound 25 was cooled to 0° C. and 8 mL of anhydrous dichloromethane was added, followed by injecting a solution of iodo compound 36 (1.40 g, 2.0 mmol) in 10 mL of dichloromethane. The reaction mixture was stirred at room temperature overnight, concentrated, and dissolved in 20 mL of THF-MeOH (2:1). The mixture was stirred at room temperature for 1 h, concentrated and treated with water-ethyl acetate. The mixture was filtered through a celite pad and washed with water and ethyl acetate. The layers were separated and the organic phase was washed with water. The combined aqueous phase was concentrated and purified on a silica gel column using 100:10:1, 100:20:1, and then 100:30:1 $CHCl_3$-MeOH-TEA as eluents. The crude product obtained was further purified on a reverse phase column eluting with water to remove all possible inorganic salts, and then with 25:1 and 5:1 water-MeOH. The phosphinic acid product 31 was obtained as a white foam, yield 160 mg (24%): silica gel TLC $R_f$ 0.40–0.50 (1:1 EtOAc-MeOH), $R_f$ 0.38 (50:10:1 $CHCl_3$-MeOH-TEA). Compound 31 obtained by this method from 36 shows identical chromatographic and spectroscopic properties as the compound obtained from compound 26. The organic phase obtained from above reaction mixture was dried ($Na_2SO_4$) and concentrated. The foam residue was purified by flash chromatography on a silica gel column. Elution with 2:1 to 1:1 hexanes-EtOAc provided 290 mg (53%) of the reduced product 42 as white needles: silica gel TLC $R_f$ 0.30 (1:1 hexanes-EtOAc); $^1H$ NMR ($CD_3OD$) d 1.03 (d, 3H, J=6.6 Hz), 1.86 (s, 3H), 2.18–2.38 (m, 1H), 3.53 (s, 3H), 3.65–3.78 (m, 2H), 3.81–3.90 (m, 1H), 3.92–4.05 (m, 1H), 5.84 (s, 1H), 8.19 (s, 1H); $^{13}C$ NMR ($CD_3OD$) d 9.1, 12.5, 35.8, 58.4, 60.8, 88.0, 89.1, 89.7, 110.3, 138.3, 152.1, 166.6; HRMS (FAB) m/z 271.129 (M+H)$^+$ ($C_{12}H_{19}N_2O_5$ requires 271.129). Anal. Calcd for $C_{12}H_{18}N_2O_5$: C, 53.32; H, 6.70; N, 10.36. Found: C, 53.50; H, 6.60; N, 10.52.

Example 23
Synthesis of Compound 32 (from 38) and Compound 43

Compound 38 (594 mg, 1.5 mmol) was reacted with BTSP 25 according to the procedure described in Example 22. Chromatographic purification provided 118 mg (23% %) of product 32 as a white foam and 256 mg (63%) of the reduced by-product 43 as white needles. Compounds 32 and 43 obtained in this way from compound 38 show identical chromatographic and spectroscopic properties as the compounds obtained from compound 36.

Example 24
Synthesis of Compound 32 and Reduced Product 43 from Compound 36

A mixture of ammonium phosphinate (810 mg, 9.7 mmol, 4.0 eq) and 1,1,1,3,3,3-hexamethyldisilazane (2.08 mL, 1.59 g, 9.8 mmol, 4.04 eq) was heated at 100–110° C. under nitrogen atmosphere with condenser. The resulting bis (trimethylsilyl)phosphonite (BTSP) (25) was cooled to 0° C. and 10 mL of anhydrous dichloromethane was added, followed by a solution of compound 36 (1.70 g, 2.43 mmol) and diisopropylethylamine (860 mL, 638 mg, 4.9 mmol, 2.0 eq) in 10 mL of dichloromethane. The resulting reaction mixture was stirred at room temperature overnight and then treated with THF-MeOH-TEA (5/8/1). The reaction mixture was stirred at room temperature for 2 h, concentrated, and then treated with mixture of water and ethyl acetate. The layers were separated and concentrated. The residue obtained from the aqueous phase was purified by flash chromatography on a silica gel column using 200:100:1 $CHCl_3$-MeOH-TEA as eluent to give 560 mg (31%) of final product 32 and 48 mg (6%) of the deprotected product 31 as white foams. Product 32 obtained in this way shows identical chromatographic and spectroscopic properties as the compound obtained from compound 31. The organic phase of the reaction mixture was dried ($Na_2SO_4$) and concentrated. The residue was purified by flash chromatography on a silica gel column. Elution with 3:1 to 1:1 hexanes-EtOAc provided 750 mg (54%) of the reduced product 43 as a white foam: silica gel TLC $R_f$ 0.45 (1:1 hexanes-EtOAc); $^1$H NMR ($CDCl_3$) d 0.94 (d, 3H, J=6.8 Hz), 1.38 (s, 3H), 2.37–2.54 (m, 1H), 3.15–3.26 (m, 1H), 3.59 (s, 3H), 3.60–3.78 (m, 2H), 3.79 (s, 6H), 3.96–4.07 (m, 1H), 5.87 (s, 1H), 6.82 (s, 2H), 6.86 (s, 2H), 7.20–7.50 (m, 9H), 7.87 (s, 1H), 9.45 (s, 1H); $^{13}$C NMR ($CDCl_3$) d 8.7, 12.1, 35.6, 55.3, 58.4, 61.5, 85.4, 86.5, 87.5, 88.9, 110.2, 113.3, 127.1, 128.0, 128.2, 130.2, 135.5, 135.8, 144.5, 150.7, 158.7, 164.9; HRMS (FAB) m/z 595.240 (M+Na)$^+$ ($C_{33}H_{36}N_2O_7Na$ requires 595.242). Anal. Calcd for $C_{33}H_{36}N_2O_7$·½$H_2O$: C, 68.19; H, 6.41; N, 4.82. Found: C, 68.27; H, 6.60; N, 4.63.

Example 25
Synthesis of Compounds 44 and 45

Compounds 44 and 45 were prepared by the procedure described in Example 24, from compound 37 (0.75 g, 1.1 mmol), ammonium phosphonate (0.365 g, 4.4 mmol, 4 eq), and 1,1,1,3,3,3-hexamethyldisilazane (0.72 g, 4.46 mmol, 4.05 eq). The product was purified by flash chromatography on a silica gel column using 200:5:1 $CH_2Cl_2$-MeOH-TEA as an eluent to give 175 mg (17%) of 1:1 salt with TEA of compound 44. The reduced compound was further purified by flash chromatography on a silica gel column using 3:1 and 2:1 hexanes-EtOAc as eluents to give 303 mg (49%) of reduced compound 45 as a white foam.

Compound 44: $^1$H NMR ($CDCl_3$) d 1.33 (t, 9H, J=7.4 Hz), 3.02 (q, 6H, J=7.4 Hz), 3.22 (d, 0.5H, J=4.4 Hz), 3.28 (d, 0.5 H, J=4.4 Hz), 3.61–3.66 (m, 1H), 3.76 (s, 6H), 3.02–4.15 (m, 1H), 5.31 (d, 0.5H, J=4.5 Hz), 5.62 (d, 0.5 H, J=4.5 Hz), 6.01 (d, 1H, J=17.2 Hz), 6.02, 8.48 (d, 1H, J=492 Hz), 6.81–7.43 (m, 14H), 7.69(s, 1H, ex $D_2O$); $^{13}$C NMR ($CDCl_3$) d 8.6, 12.0, 25.86, 27.5, 36.5, 36.9, 45.6, 55.2, 61.1, 84.0, 84.4, 86.6, 89.1, 89.8, 94.9, 98.6, 110.2, 113.3, 127.0, 128.0, 128.2, 130.1, 134.9, 135.4, 144.2, 150.4, 158.6, 164.3; $^{31}$p NMR ($CDCl_3$) d 21.27; $^{19}$F NMR ($CDCl_3$) d −61.84 (sep, $J_1$=18.7 Hz, $J_2$=35.0 Hz, $J_3$=55.2 Hz); MS (ES) m/z 623.2 (M−H)$^{31}$ ($C_{32}H_{33}N_2O_8FP$ requires 623.2).

Compound 45: $^1$H NMR ($CDCl_3$) d 1.02 (d, 3H, J=6.8 Hz), 1.44 (s, 3H), 2.43–2.74 (m, 1H), 3.21 (d, 0.5H, J=2.8 Hz), 3.27 (d, 0.5H, J=2.8 Hz), 3.67–3.73 (m, 1H), 3.79 (s, 6H), 4.02–4.07 (m, 1H), 4.91(d, 0.5H, J=4.0 Hz), 5.17 (d, 0.5H, J=4.0 Hz), 5.99 (d, 1H, J=17.2 Hz), 6.82–7.44 (m, 13H), 7.80 (s, 1H), 9.48 (br, 1H, ex $D_2O$); $^{13}$C NMR ($CDCl_3$) d 8.2, 12.1, 35.8, 36.2, 55.3, 61.1, 84.9, 86.6, 89.4, 90.2, 96.3, 100.0, 110.6, 113.3, 127.2, 127.8, 128.1, 130.1, 135.4, 144.3, 150.2, 158.8, 164.2; $^{19}$F NMR ($CDCl_3$) d −63.87 (sep, $J_1$=18.4 Hz, $J_2$=35.2 Hz, $J_3$=55.1 Hz); HRMS (FAB) m/z 561.2419 (M+H)$^+$ ($C_{32}H_{35}N_2O_6F$ requires 561.2401

Example 26
Synthesis of Compound 46

A mixture of compound 38 (1.19 g, 3.0 mmol), diisopropylethylamine (2.1 mL, 1.55 g, 12.0 mmol, 4.0 eq), and p-anisyl chlorodiphenyl methane (4'-methoxy tritylchloride, MMT-Cl) (2.78 g, 9.0 mmol, 3.0 eq) in 40 mL of ethyl acetate and 10 mL of THF was stirred at room temperature for 48 h. The reaction mixture was diluted with ethyl acetate and washed with water, followed by brine. The organic phase was dried ($Na_2SO_4$) and concentrated. The residue was purified by flash chromatography on a silica gel column. Elution with 3:1 to 1:3 hexanes-EtOAc provided 1.90 g (95%) of product 46 as a white foam: silica gel TLC $R_f$ 0.48 (1:1 hexanes-EtOAc); $^1$H NMR ($CDCl_3$) d 1.45 (s, 3H), 2.69–2.86 (m, 2H), 3.09–3.31 (m, 2H), 3.67 (s, 3H), 3.60–3.70 (m, 1H), 3.80 (s, 3H), 3.90–4.09 (m, 2H), 5.91 (s, 1H), 6.85 (s, 1H), 6.89 (s, 1H), 7.25–7.50 (m, 12H), 7.78 (s, 1H), 9.40 (s, 1H); $^{13}$C NMR ($CDCl_3$) d 12.3, 45.1, 55.3, 59.0, 61.6, 82.4, 86.8, 87.1, 88.4, 110.6, 113.4, 127.4, 127.7, 128.2, 128.4, 130.4, 134.7, 135.3, 143.6, 143.7, 150.6, 158.9, 164.6; HRMS (FAB) m/z 691.128 (M+Na)$^+$ ($C_{32}H_{33}N_2O_6INa$ requires 691.128). Anal. Calcd for $C_{32}H_{33}N_2O_6I$: C, 55.98; H, 5.13; N, 4.08. Found: C, 55.79; H, 5.10; N, 4.03.

Example 27
Synthesis of Compound 47

Compound 47 was prepared by the procedure described in Example 26 for compound 46, from compound 39 (2.72 g, 7.08 mmol), MMT-Cl (6.6 g, 21.2 mmol, 3 eq), diisopropylethylamine (3.72 ml, 2.75 g, 21.2 mmol, 3 eq) in 75 mL of ethyl acetate and 15 mL of THF. The compound was purified by flash chromatography on a silica gel column using $CH_2Cl_2$ and 200:1 $CH_2Cl_2$-MeOH as eluents to give 4.08 g (88%) of compound 47 as a pale yellow foam. $^1$H NMR ($CDCl_3$) d 1.53 (s, 3H), 2.78–3.16 (m, 3H), 3.30 (d, 0.5H, J=2.8 Hz), 3.36 (d, 0.5 H, J=2.8 Hz), 3.69–3.74 (m, 1H), 3.81 (s, 3H), 4.02–4.07 (m, 1H), 5.13 (d, 0.5H, J=3.0 Hz), 5.38 (d, 0.5H, J=3.2 Hz), 6.01 (d, 1H, J=18.2 Hz), 6.86–7.45 (m, 14H), 7.67 (s, 1H), 9.52 (br, 1H, ex $D_2O$); $^{13}$C NMR ($CDCl_3$) d 12.2, 45.5, 45.8, 55.3, 61.4, 82.2, 87.2, 88.9, 89.7, 95.6, 99.3, 111.1, 113.4, 127.4, 127.8, 128.2, 128.4, 130.4, 134.6, 135.2, 143.5, 143.7, 150.2, 159.0, 164.1; $^{19}$F NMR ($CDCl_3$) d −64.51 (sep, $J_1$=19.8 Hz, $J_2$=33.9 Hz, $J_3$=54.1 Hz).

Example 28
Synthesis of Compound 49

The 5'-MMT-2'-methoxyethyoxy compound 49 was prepared as described in Example 26 for compound 46, from compound 41 (472 mg, 1.07 mmol), Hunig's base (0.79 mL, 586 mg, 4.5 mmol, 4.0 eq), and p-anisyl chlorodiphenylmethane (1.32 g, 4.27 mmol, 4.0 eq) in a mixture of THF (6 mL) and ethyl acetate (4 mL). The crude product was purified by flash chromatography on a silica gel column. Gradient elution with 3:1, 2:1, 1:1, and then 1:3 hexanes-EtOAc provided 690 mg (99%) of the MMT-protected product 49 as a white foam: silica gel TLC $R_f$ 0.57 (1:2 hexanes-EtOAc); $^1$H NMR ($CDCl_3$) d 1.46 (s, 3H), 2.70–2.89 (m, 2H), 3.19–3.31 (m, 2H), 3.39 (s, 3H), 3.58–3.70 (m, 3H), 3.80 (s, 3H), 3.80–3.94 (m, 1H), 4.05–4.25 (m, 3H), 5.89 (s, 1H), 6.85 (s, 1H), 6.89 (s, 1H), 7.24–7.48 (m, 12H), 7.78 (s, 1H), 9.69 (s, 1H); $^{13}$C NMR ($CDCl_3$) d 12.3, 45.3, 55.3, 58.9, 61.6, 70.2, 71.9, 82.6, 85.6, 87.1, 89.1, 110.5, 113.4, 127.4, 128.2, 128.4, 130.5, 134.7, 135.3, 143.6, 143.7, 150.5, 158.9, 164.6; HRMS (FAB) m/z 735.155 (M+Na)$^+$ ($C_{34}H_{37}N_2O_7INa$ requires 735.154).

Example 29
Synthesis of Compound 50 and Reduced Product 54

A mixture of ammonium phosphite (996 mg, 12.0 mmol, 4.0 eq) and 1,1,1,3,3,3-hexamethyldisilazane (2.56 mL, 1.95 g, 12.1 mmol, 4.05 eq) was heated at 100–110° C. for 2 h under nitrogen atmosphere with condenser. The intermediate BTSP 25 was cooled to 0° C. and 10 mL of dichloromethane was injected. To this mixture was injected a solution of 46 (2.0 g, 2.99 mmol) and diisopropylethylamine (1.0 mL, 742 mg, 5.74 mmol, 1.92 eq) in 15 mL of dichloromethane. After the reaction mixture was stirred at room temperature overnight, a mixture of THF-MeOH-TEA (7/12/0.5 mL) was added and continue to stir for 1 h. The reaction mixture was filtered through a pad of celite and washed with dichloromethane. The solvent was evaporated and the residue was purified by flash chromatography providing 750 mg (35%) of product 50 and 1.02 g (63%) of the reduced product 54 as white foams.

Compound 50: silica gel TLC $R_f$ 0.40 (50:10:1 $CHCl_3$-MeOH-TEA); $^1$H NMR ($CDCl_3$) d 1.20–1.45 (m, 3H+9H), 1.50–1.85 (m, 2H), 2.45–2.70 (m, 1H), 3.02 (q, 6H, J=7.2 Hz), 3.10–3.25 (m, 1H), 3.42–3.60 (m, 1H), 3.49 (s, 3H), 3.70 (s, 3H), 3.90–4.01 (m, 2H), 5.85 (s, 1H), 5.90, 8.39 (d, 1H, J=498 Hz, P—H), 6.75 (s, 1H), 6.79 (s, 1H), 7.10–7.50 (m, 12H), 7.58 (s, 1H), 10.58 (bs, 1H); $^{13}$C NMR ($CDCl_3$) d 8.6, 12.0, 18.0, 26.5, 27.2, 36.8, 42.1, 45.6, 53.6, 55.2, 57.7, 61.9, 84.5, 84.9, 85.2, 86.6, 89.2, 109.7, 113.3, 127.1, 128.0, 128.5, 130.4, 135.1, 135.3, 143.9, 150.4, 158.6, 164.4; $^{13}$P NMR ($CDCl_3$) d 22.2; HRMS (FAB) m/z 629.202 (M+Na)$^+$ ($C_{32}H_{35}N_2PO_8Na$ requires 629.202).

Compound 54: silica gel TLC $R_f$ 0.38 (1:1 hexanes-EtOAc); $^1$H NMR ($CDCl_3$) d 0.94 (d, 3H, J=6.6 Hz), 1.39 (s, 3H), 2.38–2.55 (m, 1H), 3.17, 3.23 (dd, 1H, J=11.0, 3.0 Hz), 3.59 (s, 3H), 3.60–3.78 (m, 2H), 3.80 (s, 3H), 3.98–4.08 (m, 1H), 5.87 (s, 1H), 6.83 (s, 1H), 6.87 (s, 1H), 7.22–7.51 (m, 12H), 7.86 (s, 1H), 9.37 (s, 1H); $^{13}$C NMR ($CDCl_3$) d 8.6, 12.1, 35.6, 55.3, 58.4, 61.6, 85.3, 86.7, 87.5, 89.0, 110.2, 113.3, 127.3, 128.1, 128.5, 130.5, 135.0, 135.7, 143.9, 150.6, 158.8, 164.8; HRMS (FAB) m/z 565.233 (M+Na)$^+$ ($C_{32}H_{34}N_2O_6Na$ requires 565.231).

Example 30
Synthesis of Compounds 51 and 55

Compounds 51 and 55 were prepared by the procedure described in Example 29 for compounds 50 and 54, from compound 47 (2.0 g, 3.05 mmol), ammonium phosphite (1.01 g, 12.2 mmol, 4 eq), 1,1,1,3,3,3-hexamethyldisilazane (2.61 ml, 2.0 g, 12.35 mmol, 4.05 eq). The product was purified by flash chromatography providing 451 mg (26%) of compound 51 as a TEA salt and 690 mg (43%) of compound 55 as white foams.

Compound 51: $^1$H NMR ($CDCl_3$) d 1.25 (t, 9H, J=7.4 Hz), 1.25–1.30 (m, 1H), 1.38 (s, 3H), 1.54–1.80 (m, 2H), 2.96 (q, 6H, J=7.4 Hz), 3.24 (d, 0.5H, J=3.2 Hz), 3.30 (d, 0.5H, J=3.2 Hz), 3.62–3.67 (m, 1H), 3.79 (s, 3H), 4.05–4.12 (m, 1H), 5.32 (d, 0.5H, J=3.6 Hz), 5.57 (d, 0.5H, J=3.6 Hz), 5.97, 6.06 (d, 1H, J=17.2 Hz), 5.99, 8.48 (d, 1H, J=498 Hz), 6.82–7.45 (m,14H), 7.70 (s, 1H); $^{31}$P NMR ($CDCl_3$) d 21.36; HRMS (FAB) 696.3198 (M+H)$^+$ ($C_{37}H_{48}N_2O_7FP$ requires 696.3214).

Compound 55: $^1$H NMR ($CDCl_3$) d 1.02 (d, 3H, J=6.8 Hz), 1.44 (s, 3H), 2.43–2.73 (m, 1H), 3.22 (d, 0.5H, J=2.8 Hz), 3.28 (d, 0.5H, J=2.8 Hz), 3.67–3.72 (m, 1H), 4.02–4.08 (m, 1H), 4.90 (d, 0.5H, J=4.0 Hz), 5.16 (d, 0.5H, J=4.0 Hz), 5.97 (d, 1H, J=17.2 Hz), 6.83–7.45 (m, 14H), 7.78 (s, 1H), 8.42 (br, 1H, ex $D_2O$).

Example 31
Synthesis of Compound 53 and Reduced Product 57

Compounds 53 and 57 were synthesized according to the procedure described in Example 23, from ammonium phosphite (410 mg, 5.06 mmol, 4.6 eq), 1,1,1,3,3,3-hexamethyldisilazane (1.18 mL, 902 mg, 5.59 mmol, 5.08 eq), compound 49 (780 mg, 1.1 mmol), and Hunig's base (390 mL, 289 mg, 2.23 mmol, 2.0 eq) in dichloromethane. The crude product was purified by flash chromatography on a silica gel column. Elution with 200:40:1 and then 200:60:1 $CHCl_3$-MeOH-TEA provided 214 mg (26%) of H-phosphonate product 53 as a white foam. The reduced product was collected and repurified using 2:1, 1:1, and then 1:2 hexanes-EtOAc as eluent providing 380 mg (59%) of the pure reduced product 57 as a white foam.

Compound 53: silica gel TLC $R_f$ 0.40 (50:10:1 $CHCl_3$-MeOH-TEA); $^1$H NMR ($CDCl_3$) d 1.21 (t, 9H, J=7.2 Hz, TEA), 1.33 (s, 3H), 1.50–2.00 (m, 2H), 2.45–2.80 (m, 1H), 3.00 (q, 6H, J=7.2 Hz, TEA), 3.11–3.26 (m, 1H), 3.31 (s, 3H), 3.42–3.60 (m, 3H), 3.73 (s, 3H), 3.74–3.83 (m, 1H), 4.00–4.16 (m, 2H), 4.18–4.25 (m, 1H), 5.87 (s, 1H), 5.95, 8.45 (d, 1H, J=500 Hz, P—H), 6.78 (s, 1H), 6.83 (s, 1H), 7.10–7.35 (m, 8H), 7.36–7.47 (m, 4H), 7.60 (s, 1H), 11.0 (bs, 1H); $^{13}$C NMR ($CDCl_3$) d 8.5, 12.1, 37.0, 45.1, 55.2, 58.8, 62.0, 69.3, 71.8, 84.2, 86.6, 89.7, 109.6, 113.3, 127.0, 127.9, 128.5, 130.4, 135.1, 143.9, 150.6, 158.6, 164.6; $^{31}$P NMR ($CDCl_3$) d 22.2; HRMS (FAB) m/z 637.231 (M+Na)$^+$ ($C_{34}H_{39}N_2PO_9Na$ requires 673.229).

Compound 57: silica gel TLC $R_f$ 0.38 (1:2 hexanes-EtOAc); $^1$H NMR ($CDCl_3$) d 0.97 (d, 3H, J=6.8 Hz), 1.41 (s, 3H), 2.35–2.55 (m, 1H), 3.18, 3.24 (dd, 1H, J=11.0, 3.0 Hz), 3.37 (s, 3H), 3.54–3.68 (m, 3H), 3.79 (s, 3H), 3.75–3.87 (m, 1H), 3.94 (d, 1H, J=5.0 Hz), 4.03–4.16 (m, 2H), 5.84 (s, 1H), 6.83 (s, 1H), 6.87 (s, 1H), 7.20–7.37 (m, 8H), 7.39–7.50 (m, 4H), 7.86 (s, 1H), 9.50 (s, 1H); $^{13}$C NMR ($CDCl_3$) d 8.7, 12.1, 35.6, 55.3, 59.0, 61.7, 69.8, 72.1, 85.4, 86.4, 86.7, 89.8, 110.0, 113.3, 127.2, 128.0, 128.4, 130.4, 135.0, 135.7, 143.9, 150.5, 158.8, 164.6; HRMS (FAB) m/z 609.256 (M+Na)$^+$ ($C_{34}H_{38}N_2O_7Na$ requires 609.257).

Example 32
Synthesis of Compound 58

A solution of compound 55 (1.3 g, 2.45 mmol) and trifluoroacetic acid (TFA, 1 mL) in 25 mL of $CH_2Cl_2$ was stirred at room temperature for 30 minutes. The solution was washed with 5% $NaHCO_3$ solution, water and brine. The organic phase was dried ($Na_2SO_4$), concentrated and purified by flash chromatography on a silica gel column using 100:1 $CH_2Cl_2$-MeOH as an eluent to give 180 mg (30%) of compound 58 as a solid. $^1$H NMR ($CDCl_3$) d 1.12 (d, 3H, J=6.8 Hz), 1.89 (s, 3H), 2.38–2.70 (m, 1H), 3.75 (d, 0.5H, J=2.6 Hz), 3.81 (d, 0.5H, J=2.6 Hz), 3.96–4.02 (m, 1H), 4.09–4.17 (m, 1H), 4.90 (d, 0.5H, J=4.4 Hz), 5.16 (d, 0.5H, J=4.8 Hz), 5.89 (d, 1H, J=18.8 Hz), 7.65 (s, 1H); MS (ES) m/z 257.1 (M−H)$^-$ ($C_{11}H_{14}N_2O_4F$ requires 257.1); HRMS (FAB) m/z 259.1096 (M+H)$^+$ ($C_{11}H_{16}N_2O_4F$ requires 259.1094).

Example 33
Synthesis of Compound 59

Trifluoroacetic acid (1.5 mL) was added dropwise to a stirred solution of compound 57 (370 mg, 0.63 mmol) in 50 mL of chloroform at 0° C. The mixture was stirred at room temperature for 30 minutes, concentrated, and then dissolved in ethyl acetate. The solution was washed with dilute sodium bicarbonate and brine. The organic phase was dried ($Na_2SO_4$) and concentrated. The resulting residue was purified by flash chromatography on a silica gel column. Elution with 1:1, 1:3 and then 0:1 hexanes-EtOAc provided 170 mg (86%) of the deprotected and reduced product 59 as a white foam: silica gel TLC $R_f$ 0.20 (1:5 hexanes-EtOAc); $^1$H NMR ($CDCl_3$) d 1.03 (d, 3H, J=6.8 Hz), 1.83 (s, 3H), 2.20–2.40 (m, 1H), 3.10–3.28 (m, 1H), 3.35 (s, 3H), 3.50–4.15 (m, 10H), 5.81 (s, 1H), 7.89 (s, 1H), 9.77 (s, 1H); $^{13}$C NMR ($CDCl_3$) d 8.9, 12.4, 34.7, 59.0, 60.6, 69.7, 72.0, 86.3, 89.8, 109.7, 136.9, 150.4, 164.7; HRMS (FAB) m/z 315.154 $(M+H)^+$ ($C_{14}H_{23}N_2O_6$ requires 315.155).

Example 34
Synthesis of Compound 60

To a suspension of $CrO_3$ (1.0 g, 12 mmol, 4 eq) in 80 mL of $CH_2Cl_2$ at 0° C., acetic anhydride (1.3 ml, 1.2 g, 12 mmol, 4 eq) and pyridine (1.86 mL, 1.9 g, 24 mmol, 8 eq) were added. The resulting mixture was stirred at room temperature for 30 minutes until most of the $CrO_3$ was dissolved. A solution of compound 2 (2.0 g, 3.92 mmol) in 10 mL of $CH_2Cl_2$ was added to the above solution and continued to stir at room temperature for 1 h. The solution was poured into 500 mL of cold ethyl acetate, filtered through celite and concentrated. The residue was purified by flash chromatography on a silica gel column using 2:1 hexanes-EtOAc as an eluent to give 1.7 g (83%) of compound 60 as a white foam. $^1$H NMR ($CDCl_3$) d 1.06 (s, 9H), 1.60 (s, 3H), 3.61 (s, 3H), 4.02–4.06 (m, 3H), 4.26 (m, 1H), 6.28 (d, 1H, J=7.8 Hz), 7.36–7.65 (m, 11H), 10.30 (br, 1H, ex $D_2O$); $^{13}$C NMR ($CDCl_3$) d 11.9, 19.4, 26.9, 58.9, 63.4, 82.1 82.4, 83.9, 112.7, 128.1, 130.2, 131.7, 132.8, 134.8, 150.8,164.2, 207.9; HRMS (FAB) m/z 509.2096 $(M+H)^+$ ($C_{27}H_{33}N_2O_6Si$ requires 509.2108).

Example 35
Synthesis of Compound 62

A mixture of $Ph_3PCH_3Br$ (7.8 g, 22 mmol) and KOOC($CH_3$)$_3$ (2.5 g, 22 mmol) in 500 mL of anhydrous ether was stirred at room temperature under argon for 2 h. After the solution was cooled to −78° C., compound 60 (4.5 g, 8.85 mmol) in 10 mL of ether was injected into the solution and continued to stir at −78° C. for 1 h. The solution was stored in a refrigerator for two days and then at room temperature for 1 day. Saturated $NH_4Cl$ solution (100 ml) was added to quench the reaction. The aqueous phase was extracted with ether and the combined ether was dried ($Na_2SO_4$) and concentrated. The residue was purified by flash chromatography on a silica gel column using 5:1 hexanes-EtOAc as an eluent to give 3.8 g (85%) of compound 62 as a white foam. $^1$H NMR ($CDCl_3$) d 1.09 (s, 9H), 1.57 (s, 3H), 3.46 (s, 3H), 3.29–3.87 (m, 1H), 4.02–4.10 (m, 1H), 4.27–4.32 (m,1H), 4.67 (m, 1H), 5.22 (t,1H, J=2.0 Hz), 5.41 (t, 1H, J=2.0 Hz), 6.07 (d, 1H, J=5.5 Hz), 7.37–7.68 (m, 11H), 8.91 (br, 1H, ex $D_2O$); $^{13}$C NMR ($CDCl_3$) d12.0, 19.5, 27.0, 57.4, 65.8, 80.8, 84.5, 86.7, 110.8, 111.6, 127.9, 130.1, 132.5, 133.3, 135.4, 135.6, 144.1, 150.3, 163.7.

Example 36
Synthesis of Compound 31 from Compound 62

Sodium hypophosphite monohydrate ($NaPO_2H_2.H_2O$) (2.65 g, 2.5 mmol, 2.5 eq) was dissolved in 10 mL of water. To the stirred mixture were added sulfuric acid (1.05 g, 13.5 mmol), a solution of compound 62 (5.06 g, 10 mmol) in 125 mL of dioxane and benzoyl peroxide (0.24 g, 1.0 mmol) under argon. The resulting solution was heated to 80–100° C. for 27 h. Hexanes were added to the cold reaction mixture which was then extracted with $H_2O$. The aqueous phase was evaporated and the residue was triturated with methanol. The methanol solution was evaporated and the residue was purified by flash chromatography on a silica gel column using EtOAc and then 20:1 EtOAc-MeOH as eluents to give 1.15 g (44%) of compound 31 and 31i as a mixture of two isomers; HRMS (FAB) m/z 357.0819 $(M+Na)^+$ ($C_{12}H_{19}N_2O_7PNa$ requires 357.0828).

The isomeric mixture was separated by HPLC on a reverse phase column. 50 mM Ammonium formate in water and 50 mM ammonium formate in 95% methanol at pH of 2.8 were used as buffer solvents A and B of the mobile phase. The sample was run at the flow rate of 3 mL/min, and monitored at 254 nm. The large scale of the mixture was separated at the large reverse phase column. Two major peaks were collected and evaporated. The inorganic salt was removed after flash chromatography on a silica gel column as described previously for compound 31. The early migrating peak at the retention time of 5.8 minute was confirmed as the desired isomer 31. The sample shows identical H and P NMR spectra and other properties as the authentic sample 31. The late migrating peak at 7.8 minutes is another isomer 31i.

Example 37
Synthesis of Compound 67 from Compound 19

To a solution of compound 19 in 2 mL of pyridine was added acetic anhydride at room temperature. The resulting solution was stirred at room temperature overnight. The solvent was evaporated and the residue was dissolved in chloroform and washed with water, 5% $NaHCO_3$ solution and brine. The organic phase was dried ($Na_2SO_4$), concentrated and purified by flash chromatography on a silica gel column using 4:4:1 $CH_2Cl_2$-hexanes-EtOAc as an eluant to give 0.49 g (91% of compound 67 as a white foam. $^1$H NMR ($CDCl_3$) δ 1.10 (s, 9H), 1.55 (s, 3H), 2.02 (s, 3H), 2.68–3.03 (m, 1H), 3.80–3.86 (m, 1H), 4.20–4.31 (m, 4H), 5.13 (d, 0.5H, J=4.0 Hz), 5.98 (d, 1H, J=17.2 Hz), 7.35–7.69 (m, 11H), 9.90 (br, 1H, $D_2O$); $^{13}$C NMR ($CDCl_3$) δ 12.1, 19.5, 20.8, 27.1, 40.7, 41.1, 58.9, 63.0, 82.6, 90.6, 94.4, 98.1, 111.1, 127.7, 128.0, 130.1, 132.2, 132.5, 132.9, 135.3, 135.5, 150.4, 164.3, 170.6; $^{19}$F NMR ($CDCl_3$) δ −62.56 (sep, $J_1$=20.9 Hz, $J_2$=33.1 Hz, $J_3$=55.0 Hz); HRMS (FAB) m/z 555.2314 $(M+H)^+$ ($C_{29}H_{36}N_2O_6FSi$ requires 555.2327).

Example 38
Synthesis of Compound 69 from Compound 67

A solution of compound 67 (0.49 g, 0.88 mmol), triethylamine trifluoride (0.82 mL. 0.81 g, 5.0 mmol) in 10 mL of anhydrous THF was stirred at room temperature for 20 hours. Chloroform (100 mL) was added and the solution washed with water and brine. The combined organic phase was washed with brine, dried ($Na_2SO_4$) and concentrated. The residue was washed with ether three times to remove impurities. The product was dissolved in MeOH and filtered. The solvent was evaporated to give 0.22 g (80%) of compound 69 as a solid. $^1$H NMR ($CDCl_3$) δ 1.86 (s, 3H), 2.07 (s, 3H), 2.65–2.96 (m, 1H), 3.73 (d, 0.5H, J=2.8 Hz), 3.79 (d, 0.5H, J=2.8 Hz), 4.01–4.38 (m, 4H), 5.12 (d, 0.5H, J=4.2 Hz), 5.38 (d, 0.5H, J=4.4 Hz), 5.97 (d, 1H, J=18.6 Hz), 8.03 (s, 1H); $^{19}$F NMR ($CDCl_3$) δ −66.09 (sep, $J_1$ 32 19.8 Hz, $J_2$=34.4 Hz, $J_3$=55.3 Hz); HRMS (FAB) m/z 317.1151 $(M+H)^+$ ($C_{13}H_{18}N_2O_6F$ requires 317.1149).

Example 39
Solid Phase Synthesis of Oligonucleotides Containing 3'-methylene Phosphonate Monomers Solid phase synthesis was carried out using an Applied Biosystems (Perkin Elmer Corp.) DNA/RNA synthesizer 380B and controlled pore glass preloaded with 5'-O-DMT- 2'-deoxy mononucleoside-3'-succinates (Perseptive Biosystems) as the solid support.

The synthesis cycle is based on the H-phosphonate method and includes three reaction steps and several washing steps as follows:

(i) DMT cleavage with 3% dichloroacetic acid in dichloromethane or
  MMT cleavage with 3% trichloroacetic acid in dichloromethane
  Washing with acetonitrile
  Washing with acetonitrile/pyridine (1:1)
(ii) Coupling of 5'-O-DMT-2'-deoxy-3'-H-phosphonate mononucleotide using pivaloylchloride as the activation reagent or coupling 5'-O-DMT/MMT-2'-R-3'-methylene-H-phosphonate mononucleotide using NEP-Cl as the condensing reagent
  Washing with acetonitrile/pyridine (1:1)
(iii) Optional: capping of unreacted 5'-hydroxyfunctions using isopropylphosphite (16 eqv.) and 64 eqv. of 0.2 M pivaloylchloride in acetonitrile/pyridine (1:1).
  Washing with acetonitrile/pyridine (1:1)
  Washing with acetonitrile After oxidation of the H-phosphonate linkages of the backbone, the cleavage from the solid support and deprotection of the oligonucleotides was carried out using 25–28% aqueous ammonia for 1.5 h on column followed by 6 h at 55° C.

Example 40
Coupling of 3'-methylene Hydrogen Phosphonate Monomers

Coupling of 3'-methylene hydrogen phosphonate nucleotide monomers was performed using approximately 20 equivalents of the monomer (0.05 to 0.1 M solution in acetonitrile/pyridine (1:1)) in together with 100 equivalents of NEP-Cl (0.25 to 0.5 M in acetonitrile/pyridine (1:1)). The total coupling time was 5 to 30 minutes/step.

Figure 9:
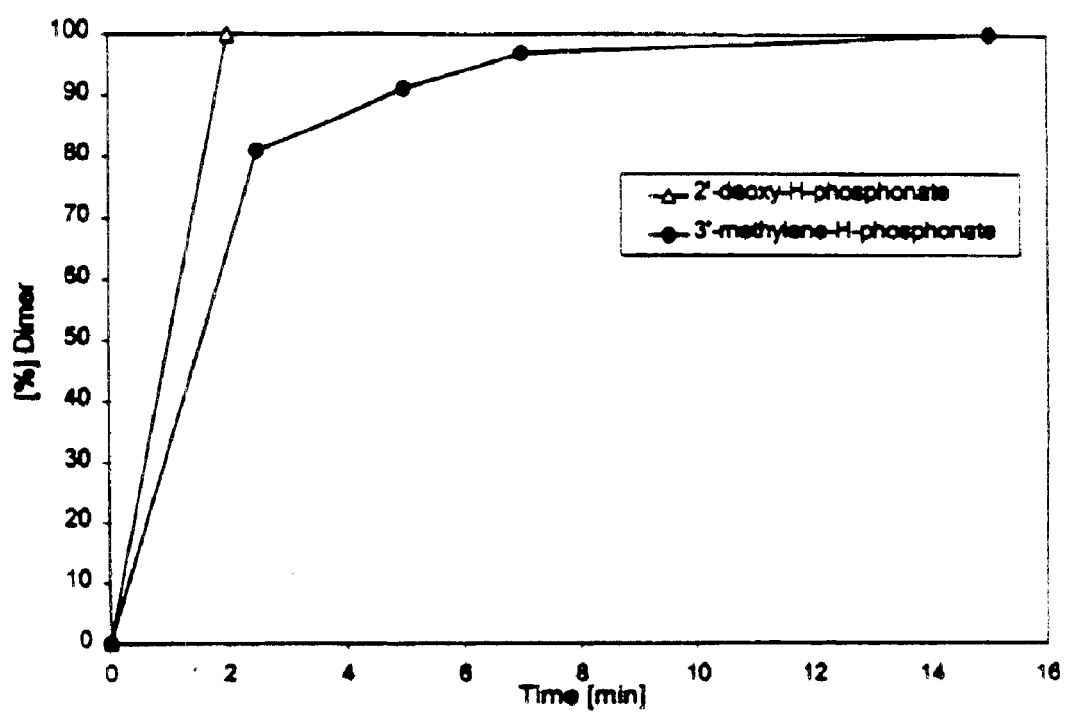
FIG. 9 is a graph showing the coupling kinetics, monitored by $^{31}P$ NMR, of $dT-OPO_2H$ and $T-CH_2—PO_2H$ using pivaloyl chloride as the condensing reagent.

Depending on the 2'-modification, 3'-methylene-H-phosphonate nucleotides can be less reactive than standard H-phosphonate nucleotides. FIG. 9 shows the results of a comparative kinetic study of the coupling reaction by $^{31}P$ NMR using pivaloyl chloride as the condensing reagent. While for a standard 2'-deoxy-3'-H-phosphonate nucleoside the coupling reaction was completed in less than 2 minutes, the 2'-O-methyl-3'-methylene-H-phosphonate monomer required about 15 minutes of reaction time.

Pivaloyl chloride is known to be one of the most active condensing reagents for the H-phosphonate coupling reaction. Froehler and Matteucci, Tet. Lett. 1986, 27, 469. Due to its reactivity, however, extended coupling times and/or increased concentrations are known to cause several unwanted side reactions such as overactivation or acylation of existing H-phosphonate internucleotide linkages. Thus, the coupling conditions had to be modified in order to achieve efficient coupling yields and to minimize possible side reactions.

Figure 10:
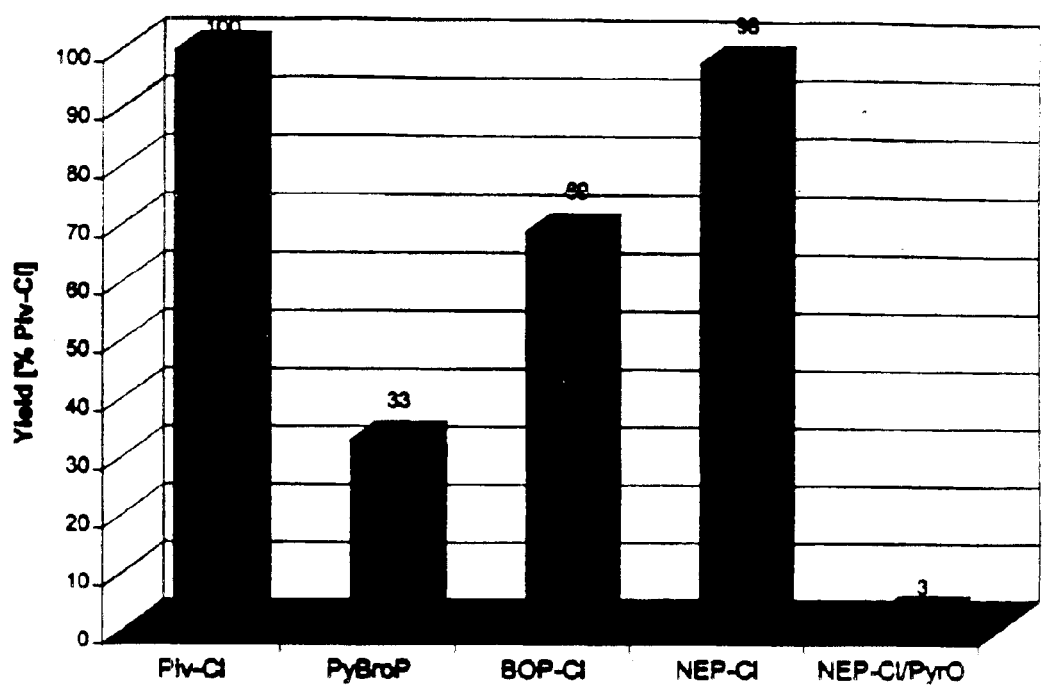
FIG. 10 is a bar graph showing the relative average stepwise coupling yields of various condensing reagents.

For synthesizing a simple polyT oligomer, various condensing reagents, in some cases in combination with a nucleophilic catalyst, have been investigated for their suitablility for solid phase synthesis. The results of this study are summarized in FIG. 10 which shows the average stepwise coupling yields obtained with the different condensing reagents in comparison to pivaloyl chloride as a standard. 2-Chloro-5,5-dimethyl-2-oxo-1,3,2-dioxaphosphinane (NEP-Cl) was the preferred condensing reagent. Moreover, NEP-Cl is known to be a milder and more selective condensing agent than pivaloyl chloride and was hence chosen for further studies.

Figure 11:
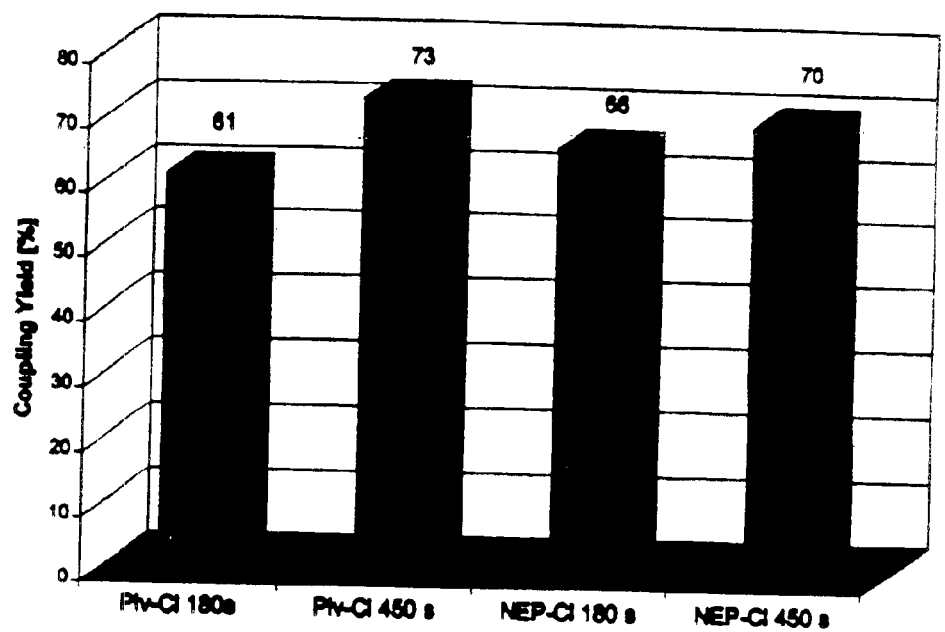
FIG. 11 is a bar graph showing the average stepwise coupling yields of 2'-methoxy-3'-methylene-H-phosphonate monomers, obtained with pivaloyl chloride and NEP-Cl as condensing reagents and different coupling times (shown in seconds (s)).

In another model study, pivaloyl chloride and NEP-Cl were compared for their ability to initiate the coupling reaction of a 3'-methylene-H-phosphonate monomer (FIG. 11). These results indicate that NEP-Cl is approximately as efficient as pivaloyl chloride while offering the ability to increase reagent concentration and coupling time without risk of increasing the side reactions mentioned above.

Figure 12:
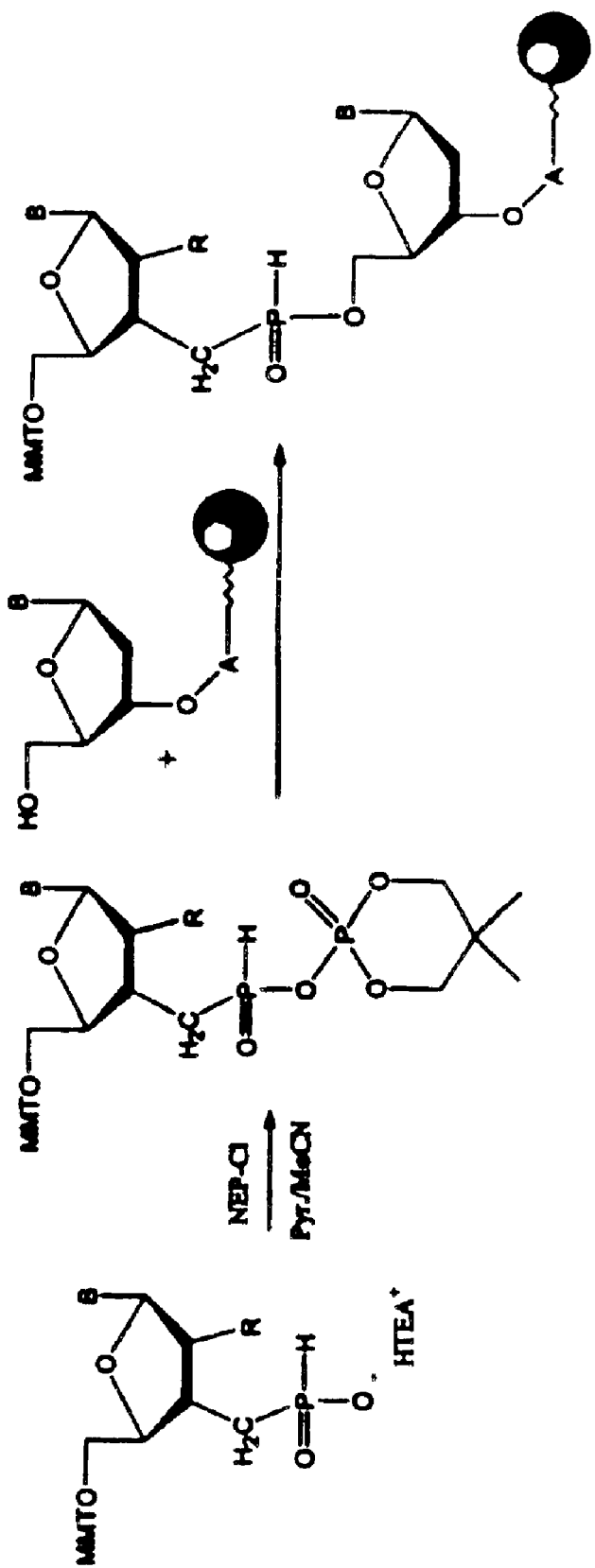
FIG. 12 is a schematic showing the coupling reaction of 3'-methylene-H-phosphonate monomers using NEP-Cl as the condensing reagent.

Using extended coupling times and increased concentrations of monomer and activator, high coupling yields were obtained. Also, no significant side reactions or adverse effect on product purity was observed under these conditions. NEP-Cl was the preferred condensing reagent for the coupling of 3'-methylene-H-phosphonate nucleotides. FIG. 12 illustrates the coupling reaction using NEP-Cl as the condensing agent.

Example 41
Oxidation Procedures for the Synthesis of Oligomers Containing a Uniform Backbone of Phosphodiester Linkages Oligonucleotides containing 3'-methylenephosphonate monomers and a uniform phosphodiester backbone were derived from oxidizing H-phosphonate oligomers on the solid support using a solution of 0.2 M (1S)-(+)-(camphorylsulfonyl)-oxaziridine (CSO) and 0.5–0.7 M N,O-bis(trimethylsilyl)-acetamide (BSA) in acetonitrile/pyridine (1:1). Depending on the number of 3'-methylene-H-phosphonate internucleoside linkages, the reaction time ranged from 2 to 12 hours.

Figure 13:
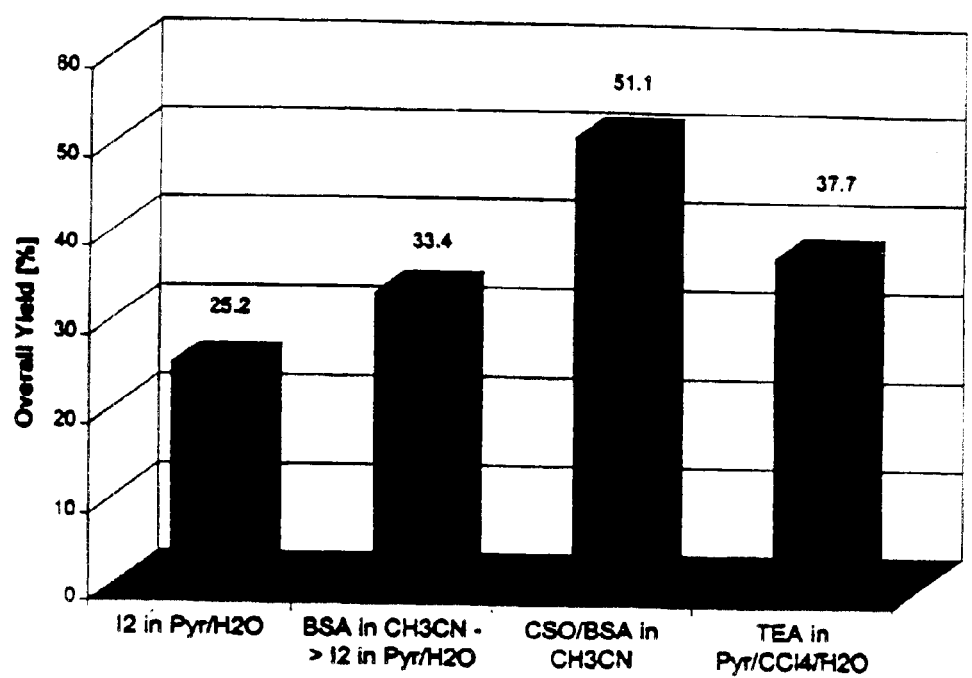
FIG. 13 is a bar graph showing the effect of various oxidation reagents on the overall yield of the synthesis of a thymidine 19 mer having three 3'-methylenephosphonate linkages.

3'-Methylene-H-phosphonate internucleoside linkages are very difficult to oxidize. In order to evaluate appropriate oxidation conditions, a $T_{19}$mer (SEQ ID NO: 1) bearing three 2'-O-methyl-3'-methylenephosphonate linkages was synthesized and oxidized using various oxidation reagents. The CGE analysis of the crude products showed that the standard oxidation procedures for H-phosphonate synthesis, which are based iodine as the oxidation reagent, are not suitable for efficiently oxidizing oligonucleotides with multiple 3'-methylene-H-phosphonate internucleoside linkages. The presence of hydrolyzed compounds indicated that even prolonged reaction times of several hours or presilylation with BSA did not result in sufficient oxidation. In contrast, the above described oxidation procedure was more efficient for the oxidation of 3'-methylene-H-phosphonate linkages. The results of this oxidation study are shown in FIG. 13.

Figure 14:
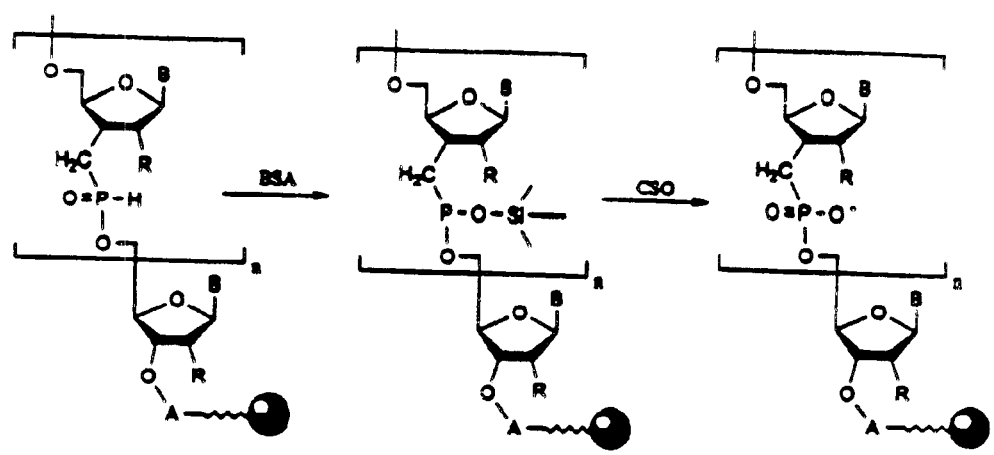
FIG. 14 is a schematic showing the oxidation of 3'-methylenephosphonate linkages using BSA/CSO as the oxidation reagent.

FIG. 14 illustrates the oxidation reaction with this novel oxidation procedure.

Example 42
Oligonucleotide Purification

After deprotection and cleavage of the 5'-ODMT-oligomers from the solid support they were purified by RP-HPLC using DeltaPak $C_{18}$ Colums and 0.1 M NH$_4$OAc buffer in a water/acetonitrile eluent system. After purification, the oligonucleotides were detritylated with acetic acid and desalted by RP-HPLC.

Example 43
Biophysical Properties of 3'-methylenephosphonate Oligonucleotides

Figure 15:
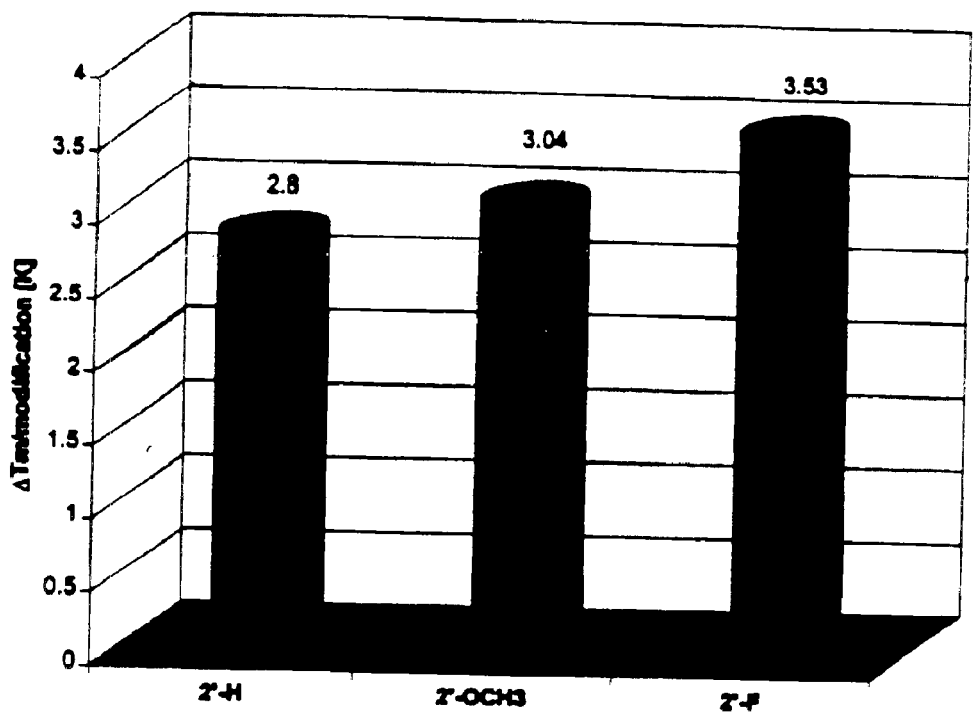
FIG. 15 is a bar graph showing the average effect of 2'-modified-3'-methylenephosphonate linkages on the melting temperature of oligonucleotides hybridized to complementary RNA relative to 2'-deoxy-3'-phosphorothioate linkages.

3'-Methylenephosphonate oligonucleotides exhibit an increased affinity towards complementary DNA or RNA strands. The average effects of various 2'-modified 3'-methylenephosphonate linkages on the affinity of oligonucleotides for complementary RNA is depicted in FIG. 15.

Dependent on the 2'-modification, an increase of 2.8 to 3.5 K per modification relative to 2'-deoxy-phosphorothioate oligonucleotides was observed.

In vitro nuclease resistance studies using snake venom phosphodiesterase as a hydrolytic enzyme which mainly shows 3'-exonuclease activity indicate that 3'-methylenephosphonate internucleoside linkages are not substrates for nucleases. Thus, oligonucleotides bearing 3'-methylenephosphonate linkages are nuclease resistant. When compared to an oligomer containing a 2'-methoxyethoxy substituent, oligonucleotides containing 3'-methylene-phosphonate linkages are protected against degradation from the 3'-end. Any degradation observed can be attributed to endonuclease activity of the enzyme which causes hydrolysis of the phosphodiester linkages present in the strand.

Example 44

Efficiency of Various Condensing Reagents Compared to Pivaloyl Chloride

Model Sequence: 5' $U_M$*TT TTT TTT TTT T (SEQ ID NO: 2)
U=5-methyluridine
T=deoxythymidine
*=3'-methylenephosphonate linkage
$_M$=2'-O-methyl nucleotide Solid phase synthesis of the n−1 oligomer (dT12 mer) was carried out on a 2 μmole scale using Piv-Cl as the condensing reagent and a solution of 0.1 M iodine in pyridine/water (49:1) for oxidation of the support-bound oligomer. Subsequently the resin was split in equal portions and the last coupling was performed using 2'-O-methyl-thymidine-3'-methylene-H-phosphonate and one of the following coupling conditions:

1. 0.2 M Piv-Cl in pyridine/acetonitrile (1:1), total coupling time: 3 min
2. 0.2 M Piv-Cl in pyridine/acetonitrile (1:1), total coupling time: 7.5 min
3. 0.25 M NEP-Cl in pyridine/acetonitrile (1:1), total coupling time: 3 min
4. 0.25 M NEP-Cl in pyridine/acetonitrile (1:1), total coupling time: 7.5 min After a final oxidation step with 0.1 M iodine in pyridine/water (49:1), the crude oligonucleotides were analyzed by electrospray mass spectrometry and capillary gel electrophoresis.

Example 45

Comparison of Various Condensing Reagents for the Coupling of 3'-methylene-H-phosphonate Monomers Model Sequence: 5' $U_M$*TT TTT TTT TTT T (SEQ ID NO: 2)
U=5-methyluridine
T=deoxythymidine
*=3'-methylenephosphonate linkage
$_M$=2'-O-methyl nucleotide Solid phase synthesis of the n−1 oligomer (dT12 mer) was carried out on a 2 μmole scale using Piv-Cl as the condensing reagent and a solution of 0.1 M iodine in pyridine/water (49:1) for oxidation of the support-bound oligomer. Subsequently the resin was split in equal portions and the last coupling was performed using 2'-O-methyl-thymidine-3'-methylene-H-phosphonate and one of the following coupling conditions:

1. 0.2 M Piv-Cl in pyridine/acetonitrile (1:1), total coupling time: 3 min
2. 0.2 M Piv-Cl in pyridine/acetonitrile (1:1), total coupling time: 7.5 min
3. 0.25 M NEP-Cl in pyridine/acetonitrile (1:1), total coupling time: 3 min
4. 0.25 M NEP-Cl in pyridine/acetonitrile (1:1), total coupling time: 7.5 min After a final oxidation step with 0.1 M iodine in pyridine/water (49:1), the crude oligonucleotides were analyzed by electrospray mass spectrometry and capillary gel electrophoresis.

Example 46

Comparison of Various Oxidizing Reagents for their Efficiency in Oxidizing 3'-methylenephosphonate Internucleotide Linkages ISIS 32327 Sequence: 5' TTT TTT TTT TTT TTT $U_M$*$U_M$*$U_M$* $U_M$ (SEQ ID NO: 3)
U=5-methyluridine
T=deoxythymidine
*=3'-methylenephosphonate linkage
$_M$=2'-O-methyl nucleotide The solid phase synthesis of a 19mer oligonucleotide (ISIS 32327), containing three 2'-O-methyl-3'-methylenephosphonate units and a uniform PO-backbone, was performed on a 2 μmole scale using 5'-O-DMT-2'-methoxy-5-methyluridine-3'-succinyl CPG as the solid support. The synthesis cycle is described in Example 39. After completion of synthesis, the solid support was dried in vacuum, divided in equal portions, and the support-bound oligomers were oxidized using the following conditions:

1. 0.2 M iodine in pyridine/water (49:1), reaction time =120 min
2. 0.5 M BSA in acetonitrile, reaction time=60 min followed by 0.2 M iodine in pyridine/water (49:1), reaction time=60 min
3. 0.2 M CSO and 0.5 M BSA in acetonitrile, reaction time=120 min
4. 0.1 M TEA in pyridine/carbontetrachloride/water (9:5:1), reaction time=120 min After oxidation, the resin was washed with acetonitrile/pyridine (1:1) and acetonitrile. Deprotection and cleavage from the solid support was performed with 25–28% aqueous ammonia. The crude products were analyzed by capillary gel electrophoresis and electrospray mass spectrometry. Analysis of the combined purified products gave a relative molecular mass of 5831.9 (calculated mass: 5830.7).

Example 47

Synthesis of a Pentamer Containing One 2'-O-methyl-3'-methylenephosphonate Monomer and a Uniform Phosphodiester (P=O) Backbone ISIS 32315 Sequence: 5' GA$U_M$* CT
U=5-methyluridine
T=deoxythymidine
*=3'-methylenephosphonate linkage
$_M$=2'-O-methyl nucleotide The solid phase synthesis of an oligonucleotide (pentamer) (ISIS 32315), containing one 2'-O-methyl-3'-methylenephosphonate unit and a uniform P=O backbone, was performed on a 2 μmole scale using 5'-O-DMT-2'-deoxythymidine-3'-succinyl CPG as the solid support. The synthesis cycle is described in Example 39. After completion of synthesis, the oligomer was oxidized using 0.2 M iodine in pyridine/water (98:2) for 2 h and washed with acetonitrile/pyridine (1:1) and acetonitrile. Deprotection and cleavage from the solid support was performed with 25–28% aqueous ammonia. Analysis of the purified product by electrospray mass spectrometry gave a relative molecular mass of 1505.8 (calculated mass: 1506.1).

Example 48
Synthesis of a Decamer Containing One 2'-O-methyl-3'-methylenephosphonate Monomer and a Uniform Phosphodiester (P=O) Backbone ISIS 32314 Sequence: 5' GCG TAU$_M$* ACG C (SEQ ID NO: 4)
U=5-methyluridine
T=deoxythymidine
*=3'-methylenephosphonate linkage
$_M$=2'-O-methyl nucleotide The solid phase synthesis of a 10mer oligonucleotide (ISIS 32314), containing one 2'-O-methyl-3' methylenephosphonate monomer and a uniform P=O backbone, was performed on a 2 μmole scale using 5'-O-DMT-2'-deoxycytidin-3'-succinyl CPG as the solid support. The synthesis cycle is described in Example 39. After completion of synthesis, the oligomer was oxidized using 0.2 M iodine in pyridine/water (98:2) for 2 h and washed with acetonitrile/pyridine (1:1) and acetonitrile. Deprotection and cleavage from the solid support was performed with 25–28% aqueous ammonia. Analysis of the purified product by electrospray mass spectrometry gave a relative molecular mass of 3056.0 (calculated mass: 3056.1).

Example 49
Synthesis of a 15mer Containing One 2'-O-methyl-3'-methylenephosphonate Monomer and a Uniform Phosphodiester (P=O) Backbone Sequence: 5' TTT U*$_M$TC TCT CTC TCT (SEQ ID NO: 5)
U=5-methyluridine
T=deoxythymidine
*=3'-methylenephosphonate linkage
$_M$=2'-O-methyl nucleotide The solid phase synthesis of a 15mer oligonucleotide, containing one 2'-O-methyl-3' methylenephosphonate monomer and a uniform P=O backbone, was performed on a 2 μmole scale using 5'-O-DMT-2'-deoxythymidine-3'-succinyl CPG as the solid support. The synthesis cycle is described in Example 39. After completion of synthesis, the oligomer was oxidized using a solution of 0.2 M CSO and 0.5 M BSA in pyridine/acetonitrile (1:1) for 3 h and washed with acetonitrile/pyridine (1:1) and acetonitrile. Deprotection and cleavage from the solid support was performed with 25–28% aqueous ammonia. Analysis of the purified product by electrospray mass spectrometry gave a relative molecular mass of 3936.0 (calculated mass: 3936.7).

Example 50
Synthesis of a 18mer Containing Four 2'-O-methyl-3'-methylenephosphonate Monomers and a Uniform Phosphodiester (P=O) Backbone ISIS 32316 Sequence: 5' CTC GTA CU$_M$*U$_M$* U$_M$*U$_M$*C CGG TCC (SEQ ID NO: 6)
U=5-methyluridine
T=deoxythymidine
*=3'-methylenephosphonate linkage
$_M$=2'-O-methyl The solid phase synthesis of a 18mer oligonucleotide (ISIS 32316), containing four 2'-O-methyl-3'-methylenephosphonate monomers and a uniform P=O backbone, was performed on a 2 μmole scale using 5'-O-DMT-2'-deoxycytidine-3'-succinyl CPG as the solid support. The synthesis cycle is described in Example 39. After completion of synthesis, the oligomer was oxidized using a solution of 0.2 M CSO and 0.5 M BSA in pyridine/acetonitrile (1:1) for 3 h and washed with acetonitrile/pyridine (1:1) and acetonitrile. Deprotection and cleavage from the solid support 25 was performed with 25–28% aqueous ammonia. Analysis of the purified product by electrospray mass spectrometry gave a relative molecular mass of 5504.9 (calculated mass: 5504.8).

Example 51
Synthesis of a 16 mer Containing Four 2'-O-methyl-3'-methylenephosphonate Monomers and a Uniform Phosphodiester (P=O) Backbone ISIS 32313 Sequence: 5' U$_M$*CC AGG U$_M$*GU$_M$* CCG CAU$_M$* C (SEQ ID NO: 7)
U=5-methyluridine
T=deoxythymidine
*=3'-methylenephosphonate linkage
$_M$=2'-O-methyl The solid phase synthesis of a 16 mer oligonucleotide (ISIS 32313), containing four 2'-O-methyl-3'-methylenephosphonate monomers and a uniform P=O backbone, was performed on a 2 μmole scale using 5'-O-DMT-2'-deoxycytidine-3'-succinyl CPG as the solid support. The synthesis cycle is described in Example 39. After completion of synthesis, the oligomer was oxidized using a solution of 0.2 M CSO and 0.5 M BSA in pyridine/acetonitrile (1:1) for 12 h and washed with acetonitrile/pyridine (1:1) and acetonitrile. Deprotection and cleavage from the solid support was performed with 25–28% aqueous ammonia. Analysis of the purified product by electrospray mass spectrometry gave a relative molecular mass of 4946.1 (calculated mass: 4945.4).

Example 52
Synthesis of a 13 mer Containing One 2'-O-methyl-3'-methylenethiophosphonate Monomer Sequence: 5' TU*$_M$T TTT TTT TTT T (SEQ ID NO: 8)
U=5-methyluridine
T=deoxythymidine
*=3'-methylenethiophosphonate linkage
$_M$=2'-O-methyl nucleotide The solid phase synthesis of a 13 mer oligonucleotide containing one 2'-O-methyl-3'-methylenethiophosphonate monomer was performed on a 2 μmole scale using 5'-O-DMT-2'-deoxythymidine-3'-succinyl CPG as the solid support. The synthesis cycle is described in Example 39. After coupling of nucleotide 11, oxidation was performed using 0.1 M triethylamine in pyridine/carbontetrachloride/water (9:5:1) for 2 h. After coupling of the 3'-methylene-H-phosphonate monomer, oxidation was carried out using 10% S$_8$ in carbondisulfide/pyridine/triethylamine (35:35:1). After coupling of the final monomer, another P=O oxidation step was carried out using 0.1 M triethylamine in pyridine/carbontetrachloride/water (9:5:1) for 2 h. Deprotection and cleavage from the solid support was performed with 25–28% aqueous ammonia. Analysis of the purified product by electrospray mass spectrometry gave a relative molecular mass of 3936.0 (calculated mass: 3936.7).

Example 53

Synthesis of a 10 mer Containing One 2'-fluoro-3'-methylenephosphonate Monomer and a Uniform Phosphodiester (P=O) Backbone ISIS 32358 Sequence: 5' GCG TAU*$_F$ACG C (SEQ ID NO: 9)
U=5-methyluridine
T=deoxythymidine
*=3'-methylenephosphonate linkage
$_F$=2'-fluoro The solid phase synthesis of a 10 mer oligonucleotide (ISIS 32358), containing one 2'-flouro-3'-methylenephosphonate monomer and a uniform P=O backbone, was performed on a 2 μmole scale using 5'-O-DMT-2'-deoxycytidine-3'-succinyl CPG as the solid support. The synthesis cycle is described in Example 39. After completion of synthesis, the oxidation step was performed using a solution of 0.2 M CSO and 0.7 M BSA in pyridine/acetonitrile (1:1) for 12 h and washed with acetonitrile/pyridine (1:1) and acetonitrile. Deprotection and cleavage from the solid support was performed with 25–28% aqueous ammonia. Analysis of the purified product by electrospray mass spectrometry gave a relative molecular mass of 3043.56 (calculated mass: 3044.0).

Example 54

Synthesis of a 16 mer Containing Four 2'-fluoro-3'-methylenephosphonate Monomers and a Uniform Phosphodiester (P=O) Backbone ISIS 32357 Sequence: 5' U$_F$*CC AGG U$_F$*GU$_F$* CCG CAU$_F$* C (SEQ ID NO: 10)
U=5-methyluridine
*=3'-methylenephosphonate linkage
$_F$=2'-fluoro The solid phase synthesis of a 16 mer oligonucleotide (ISIS 32357), containing four 2'-flouro-3'-methylenephosphonate monomers and a uniform P=O backbone, was performed on a 2 μmole scale using 5'-O-DMT-2'-deoxycytidine-3'-succinyl CPG as the solid support. The synthesis cycle is described in Example 39. After completion of synthesis, oxidation was carried out using a solution of 0.2 M CSO and 0.7 M BSA in pyridine/acetonitrile (1:1) for 12 h and washed with acetonitrile/pyridine (1:1) and acetonitrile. Deprotection and cleavage from the solid support was performed with 25–28% aqueous ammonia. Analysis of the purified product by electrospray mass spectrometry gave a relative molecular mass of 4896.9 (calculated mass: 4897.2).

Example 55

Synthesis of a 18 mer Containing Four 2'-fluoro-3'-methylenephosphonate Monomers and a Uniform Phosphodiester (P=O) Backbone ISIS 32353 Sequence: 5' CTC GTA CU$_F$*U$_F$* U$_F$*U$_F$*C CGG TCC (SEQ ID NO: 11)
U=5-methyluridine
T=deoxythymidine
*=3'-methylenephosphonate linkage
$_F$=2'-fluoro The solid phase synthesis of a 16 mer oligonucleotide (ISIS 32353), containing four 2'-flouro-3'-methylenephosphonate monomers and a uniform P=O backbone, was performed on a 2 μmole scale using 5'-O-DMT-2'-deoxycytidine-3'-succinyl CPG as the solid support. The synthesis cycle is described in Example 39. After completion of synthesis, the oligomer was oxidized using a solution of 0.2 M CSO and 0.7 M BSA in pyridine/acetonitrile (1:1) for 12 h and washed with acetonitrile/pyridine (1:1) and acetonitrile. Deprotection and cleavage from the solid support was performed with 25–28% aqueous ammonia. Analysis of the purified product by electrospray mass spectrometry gave a relative molecular mass of 5455.2 (calculated mass: 5456.6).

Example 56

Synthesis of a 16 mer Containing Ten 2'-fluoro-3'-methylenephosphonate Monomers and a Uniform Phosphodiester (P=O) Backbone ISIS 32359 Sequence: 5' GCG U$_F$*U$_F$*U$_F$* U$_F$*U$_F$*U$_F$* U$_F$*U$_F$*U$_F$* U$_F$*GC G (SEQ ID NO: 12)
U=5-methyluridine
T=deoxythymidine
*=3'-methylene-phosphonate linkage
$_F$=2'-fluoro The solid phase synthesis of a 16 mer oligonucleotide (ISIS 32359), containing ten 2'-flouro-3'-methylenephosphonate monomers and a uniform P=O backbone, was performed on a 2 μmole scale using 5'-O-DMT-2'-deoxyguanosine-3'-succinyl CPG as the solid support. The synthesis cycle is described in Example 39. After completion of synthesis, the oligomer was oxidized using a solution of 0.2 M CSO and 0.7 M BSA in pyridine/acetonitrile (1:1) for 12 h and washed with acetonitrile/pyridine (1:1) and acetonitrile. Deprotection and cleavage from the solid support was performed with 25–28% aqueous ammonia. Analysis of the crude product by electrospray mass spectrometry gave a relative molecular mass of 5338.6 (calculated mass: 5337.8).

What is claimed is:

1. An oligomer of formula II:

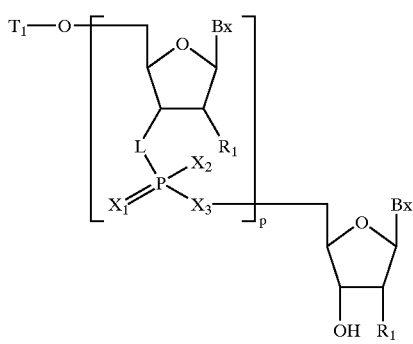

wherein:
- $B_x$ is a protected or unprotected heterocyclic base moiety;
- $T_1$ is an oligonucleotide, oligonucleoside, nucleoside, nucleotide, H or a hydroxyl protecting group;
- each $X_1$ and $X_3$ is, independently, O, S or NH;
- each $X_2$ is, independantly, OH, SH or $NH_2$;
- each L is, independantly, $C(Y_1)(Y_2)$ or O, provided that at least one L is $C(Y_1)(Y_2)$;
- each $R_1$, independently, has one of formulas:

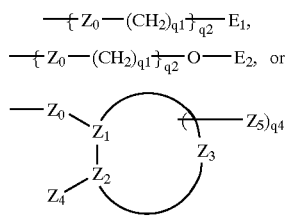

wherein:
- $Z_0$ is, independently, O, S or NH;
- $E_2$ is $N(Q_1)(Q_2)$ or $N=C(Q_1)(Q_2)$;
- $E_2$ is $C_1-C_{10}$ alkyl;
- each $Q_1$ and $Q_2$ is, independently, H, $C_1-C_{10}$ alkyl, substituted alkyl, dialkylaminoalkyl, a nitrogen protecting group, a tethered or untethered conjugate group, a linker to a solid support;
- or $Q_1$ and $Q_2$, together, are joined in a nitrogen protecting group or a ring structure that can include at least one additional heteroatom selected from N and O;
- each $q^1$ is, independently, from 1 to 10;
- $q^2$ is from 1 to 10;
- $q^3$
- $q^4$ is zero, 1 or 2;
- $q^5$
- each $M_1$ is, independently, H, $C_1-C_8$ alkyl, $C_1-C_8$ haloalkyl, $C(=NH)N(H)M_2$, $C(=O)N(H)M_2$ or $OC(=O)N(H)M_2$;
- $M_2$ is H or $C_1-C_8$ alkyl;
- $Z_1$, $Z_2$ and $Z_3$ comprise a ring system having from about 4 to about 7 carbon atoms or having from about 3 to about 6 carbon atoms and 1 or 2 heteroatoms wherein said heteroatoms are selected from oxygen, nitrogen and sulfur and wherein said ring system is aliphatic, unsaturated aliphatic, aromatic, or saturated or unsaturated heterocyclic; and
- $Z_4$ is $OM_1$, $SM_1$, or $N(M_1)_2$;
- $Z_5$ is alkyl or haloalkyl having 1 to about 10 carbon atoms, alkenyl having 2 to about 10 carbon atoms, alkynyl having 2 to about 10 carbon atoms, aryl having 6 to about 14 carbon atoms, $N(Q_1)(Q_2)$, $OQ_1$, halo, $SQ_1$ or CN;
- p is 0 or an integer from 1 to 50; and
- each of $Y_1$ and $Y_2$ is, independently, H, alkyl, substituted alkyl, aryl, substituted aryl, heterocyclyl, cyano, carboxyl, ester or a cyclic moiety;
- wherein said substituted alkyl groups are substituted with one or more of alkyl, alkenyl, alkynyl, aryl, hydroxyl, alkoxy, alcohol, benzyl, phenyl, nitro, thiol, thioalkoxy, thioalkyl, trifluoromethyl, halo, nitrile, trifluoromethoxy or azido, and said substituted aryl groups are substituted with one or more of hydroxyl, alkoxy, alcohol, benzyl, phenyl, nitro, thiol, thioalkoxy, halogen, alkyl, aryl, alkenyl, or alkynyl.

2. The oligomer of claim 1 wherein at least one L is a methylene group.

3. The oligomer of claim 1 wherein said hydroxyl protecting group is trityl, monomethoxytrityl, dimethoxytrityl, trimethoxytrityl, 9-phenylxanthin-9-yl, t-butyldiphenylsilyl or t-butyldimethylsilyl.

4. The oligomer of claim 1 wherein at least one $R_1$ is $OCH_2CH_2OCH_3$.

* * * * *

UNITED STATES PATENT AND TRADEMARK OFFICE
CERTIFICATE OF CORRECTION

| | | |
|---|---|---|
| PATENT NO. | : 6,974,865 B2 | Page 1 of 1 |
| APPLICATION NO. | : 10/322242 | |
| DATED | : December 13, 2005 | |
| INVENTOR(S) | : Phillip Dan Cook et al. | |

It is certified that error appears in the above-identified patent and that said Letters Patent is hereby corrected as shown below:

Title page,
Item [63], Related U.S. Application Data, delete "Continuation of application No. 09/349,033, filed on Jul. 7, 1999, now Pat. No. 6,639,061, and a continuation of application No. 10/153,320, filed on May 22, 2002, which is a continuation of application No. 09/058,470, filed on Apr. 10, 1998, now abandoned, which is a division of application No. 08/763,354, filed on Dec. 11, 1996, now Pat. No. 5,965,721, which is a continuation of application No. 08/150,079, filed on Apr. 7, 1994, now Pat. No. 5,610,289" and insert -- Continuation of application No. 09/349,033, filed on Jul. 7, 1999, now Pat. No. 6,639,061, and a continuation of application No. 10/153,320, filed on May 22, 2002, which is a continuation of application No. 09/058,470, filed on Apr. 10, 1998, now abandoned, which is a division of application No. 08/763,354, filed on Dec. 11, 1996, now Pat. No. 5,965,721, which is a division of application No. 08/150,079, filed on Apr. 7, 1994, now Pat. No. 5,610,289 --;

Column 59,
Lines 33 and 34, delete "indepenedantly" and insert -- independently --;
Line 50, delete "$E_2$" and insert -- $E_1$ --;

Column 60,
Line 14, delete "$q^3$";
Line 16, delete "$q^5$".

Signed and Sealed this

Eleventh Day of July, 2006

JON W. DUDAS
*Director of the United States Patent and Trademark Office*